United States Patent [19]

Burgess et al.

[11] Patent Number: 5,498,831
[45] Date of Patent: Mar. 12, 1996

[54] PEA ADP-GLUCOSE PYROPHOSPHORYLASE SUBUNIT GENES AND THEIR USES

[75] Inventors: Diane G. Burgess, Berkeley; Hugo K. Dooner, Walnut Creek, both of Calif.

[73] Assignee: DNA Plant Technology Corporation, Oakland, Calif.

[21] Appl. No.: 97,829

[22] Filed: Jul. 23, 1993

[51] Int. Cl.[6] .............................. A01H 1/04; A01H 4/00; A01H 5/00; C07H 21/04
[52] U.S. Cl. ...................... 800/205; 800/200; 800/250; 800/255; 800/DIG. 23; 435/172.1; 435/172.3; 435/240.4; 435/240.49; 435/100; 435/194; 536/23.2; 536/23.6; 536/24.5
[58] Field of Search ................................. 800/200, 205, 800/250, 255, DIG. 23; 435/172.1, 172.3, 100, 194, 240.4, 240.49; 536/23.2, 23.6, 24.5; 935/18

[56] References Cited

U.S. PATENT DOCUMENTS

| | | | |
|---|---|---|---|
| 5,231,020 | 7/1993 | Jorgenson et al. | 435/172.3 |
| 5,286,635 | 2/1994 | Hanson et al. | 435/172.3 |

FOREIGN PATENT DOCUMENTS

| | | |
|---|---|---|
| 368506 | 10/1989 | European Pat. Off. . |
| WO91/19806 | 6/1991 | WIPO . |
| WO92/11382 | 12/1991 | WIPO . |
| WO93/09237 | 11/1992 | WIPO . |
| 9411520 | 5/1994 | WIPO . |

OTHER PUBLICATIONS

Anderson, J. M., Larsen, R., Laudencia, D., Kim, W. T., Morrow, D., Okita, T. W. and Preiss, J., "Molecular characterization of the gene encoding a rice endosperm-specific ADP-glucose pyrophophorylase subunit and its developmental pattern of transcription," *Gene* 97:199–205 (1991).
Villand, P., Aalen, R., Olsen, O., Lüthi, E., Lönneborg, A. and Kleczkowski, L. A., "PCR amplification and sequences of cDNA clones for the small and large subunits of ADP–glucose pyrophosphorylase from barley tissues," *Plant Molecular Biology* 19:381–389 (1992).
Preiss, J., Cress, D., Hutny, J., Morell, M., Bloom, M., Okita, T., and Anderson, J., Ch. 6 "Regulation of starch synthesis: biochemical and genetic studies". In: *ACS Symposium Series 389 on Biocatalysis in Agricultural Biotechnology*, American Chemical Society, Washington, D.C. (1989).
Bae, J. M., Giroux, M., and Hannah, L. "Cloning and characterization of the *brittle*-2 gene of maize," *Maydica* 35:317–322 (1990).
Plaxton, W. C. and Preiss, J. "Purification and properties of nonproteolytic degraded ADP–glucose pyrophosphorylase from maize endosperm," *Plant Physiol.* 83:105–112 (1987).
Morell, M., Bloom, M., and Preiss, J. "Affinity labeling of the allosteric activator site(s) of spinach leaf ADP–glucose pyrophosphorylase," *J. Biol. Chem.* 263:633–637 (1988).
Spilatro, S. R. and Preiss, J. "Regulation of starch synthesis in the bundle sheath and mesophyll of Zea *mays,*" *Plant Physiol.* 83:621–627 (1987).
Okita, T. W., Nakata, P. A., Anderson, J. M., Sowokinos, J., Morell, M., and Preiss, J. "The subunit structure of potato tuber ADP–glucose pyrophosphorylase," *Plant Physiol.* 93:785–790 (1990).
Nakamura, Y. and Kawaguchi, K. "Multiple forms of ADP–glucose pyrophosphorylase of rice endosperm," *Phys. Plant.* 84:336–342 (1992).
Bhave, M. R., Lawrence, S., Barton, C., and Hannah, L. C. "Identification and molecular characterization of *Shrunken*-2 cDNA clones of maize," *Plant Cell* 2:581–588 (1990).
Nakata, P. A., Greene, T. W., Anderson, J. M., Smith–White, B. J., Okita, T. W., and Preiss, J. "Comparison of the primary sequences of two potato tuber ADP–glucose pyrophosphorylase subunits," *Plant Mol. Biol.* 17:1089–1093 (1991).
Stark, D. M., Timmerman, K. P., Barry, G. F., Preiss, J., and Kishore, G. M., "Regulation of the amount of starch in plant tissues by ADP–glucose pyrophosphorylase," *Science* 258:287–292 (1992).
Kleczkowski, L. A., Villand, P., Luthi, E., Olsen, O–A, and Preiss, J., "Insensitivity of barley endosperm ADP–glucose pyrophosphorylase to 3–phosphoglycerate and orthophosphate regulation," *Plant Physiol.* 101:179–186 (1993).
Müller–Röber, B., Sonnewald, U., and Willmitzer, L. "Inhibition of the ADP–glucose pyrophosphorylase in transgenic potatoes leads to sugar–storing tubers and influences tuber formation and expression of tuber storage protein genes," *EMBO J.* 11:1229–1238 (1992).
Shaw, Janine R., Hannah, L. Curtis, "Geonomic Nucleotide Sequence of a Wild–Type Shrunken–2 Allele of Zea mays," *Plant Physiol.* 98:1214–1216 (1992).
Olive, Mark R., Ellis, R. John, Schuch, Wolfgang W., "Isolation and nucleotide sequences of cDNA clones encoding ADP–glucose pyrophosphorylase polypeptides from wheat leaf and endosperm," *Plant Molecular Biology* 12:525–538 (1989).
Villand, Per, Olsen, Odd–Arne, Kilian, Andrzej, Kleczkowski, Leszek A., "ADP–Glucose Pyrophosphorylase Large Subunit cDNA from Barley Endosperm," *Plant Physiol.* 100:1617–1618 (1992).
Hylton et al. 1992. Plant Physiol. 99:1626–1634.
Anderson et al. 1989. The Journal of Biological Chemistry. 264(21):12238–12242.
Smith et al. 1991. Biochemical Society Transactions. 19(3):547–550.
Anderson et al. 1990. In The Molec. and Cell. Biol. of the Potato. Vayda et al., eds. CAB Int. Wallingford, U.K. Ch. 12:159–180.
Smith et al. 1989. Plant Physiol. 89:1279–1284.

*Primary Examiner*—David T. Fox
*Assistant Examiner*—Erich E. Veitenheimer
*Attorney, Agent, or Firm*—Townsend and Townsend and Crew

[57] ABSTRACT

Polynucleotides encoding Pea ADP-glucose pyrophosphorylase subunits are provided that are useful for changing the phenotype of higher plants, especially the garden pea (*Pisum sativum* L.) and other legumes, in regard to starch and sucrose biosynthesis. In particular, the invention relates to affecting the sucrose and starch content of edible plants.

23 Claims, 23 Drawing Sheets

Figure 1-1

Sh2 pea cDNA sequence

```
GTCACATTCT TCTCTTTGTT TCTCTAGATT CTATATTTTA GTTGTGACCT TTCACTACTA    60
GCATTGTTTC TCTCTTATTC TCTTGGTCTG AGTTTGAACA AACTCAAAAA AAGCTTAGTT   120
TTTGAGGTT ACTACA ATG GCT TCT GGT TGT GTG AGC TTG AAA ACC AAC        169
               Met Ala Ser Gly Cys Val Ser Leu Lys Thr Asn
                 1               5                      10

ACC CAT TTT CCA AAT TCT AAA AAA GGT TCT TTT GGG GAA AGA ATC         217
Thr His Phe Pro Asn Ser Lys Lys Gly Ser Phe Gly Glu Arg Ile
               15                      20                25

AAA GGA AGC TTG AAA AAC AGT TCA TGG GTC ACT ACC CAG AAG AAG ATC     265
Lys Gly Ser Leu Lys Asn Ser Ser Trp Val Thr Thr Gln Lys Lys Ile
              30                      35                      40

AAA CCT GCT TCT TTT TCT GCT ATT CTT ACT TCA GAT GAC CCC AAA GGT     313
Lys Pro Ala Ser Phe Ser Ala Ile Leu Thr Ser Asp Asp Pro Lys Gly
              45                      50                      55

TCC CTG AAT TTG CAA GTG CCT TCA TTT CTG AGA CTA AGA GCT GAT CCA     361
Ser Leu Asn Leu Gln Val Pro Ser Phe Leu Arg Leu Arg Ala Asp Pro
              60                      65                      70                75
```

Figure 1-2

| | | | | | | | | | | | | | | | | |
|---|---|---|---|---|---|---|---|---|---|---|---|---|---|---|---|---|
| AAA | AAT | GTG | ATT | TCC | ATT | GTG | TTG | GGA | GGG | CCT | GGA | ACA | CAT | CTC | | 409 |
| Lys | Asn | Val | Ile | Ser | Ile | Val | Leu | Gly | Gly | Pro | Gly | Thr | His | Leu | | |
| | | | | 80 | | | | | 85 | | | | | 90 | | |
| TAT | CCT | CTT | ACC | AAA | CGA | GCT | GCA | ACA | CCT | GCG | GTT | CCT | GTT | GGA | GGA | 457 |
| Tyr | Pro | Leu | Thr | Lys | Arg | Ala | Ala | Thr | Pro | Ala | Val | Pro | Val | Gly | Gly | |
| | | | 95 | | | | | 100 | | | | 105 | | | | |
| TGC | TAT | AGG | CTT | ATA | GAC | ATT | CCA | ATG | AGC | AAC | TGC | ATC | AAT | AGT | GGC | 505 |
| Cys | Tyr | Arg | Leu | Ile | Asp | Ile | Pro | Met | Ser | Asn | Cys | Ile | Asn | Ser | Gly | |
| | | 110 | | | | | 115 | | | | | 120 | | | | |
| ATC | AAC | AAG | ATA | TTT | GTG | CTG | ACT | CAG | TTC | AAC | TCT | GCT | TCA | CTA | AAT | 553 |
| Ile | Asn | Lys | Ile | Phe | Val | Leu | Thr | Gln | Phe | Asn | Ser | Ala | Ser | Leu | Asn | |
| | 125 | | | | | 130 | | | | | 135 | | | | | |
| CGT | CAC | ATC | GCT | CGC | ACC | TAT | TTC | GGA | AAT | GGT | GTC | AAC | TTT | GGA | GAT | 601 |
| Arg | His | Ile | Ala | Arg | Thr | Tyr | Phe | Gly | Asn | Gly | Val | Asn | Phe | Gly | Asp | |
| 140 | | | | | 145 | | | | | 150 | | | | | 155 | |
| GGA | TTT | GTG | GAG | GTT | CGT | CTG | GCG | GCG | ACT | CAA | CCA | GGA | GAA | GCT | GGG | 649 |
| Gly | Phe | Val | Glu | Val | Arg | Leu | Ala | Ala | Thr | Gln | Pro | Gly | Glu | Ala | Gly | |
| | | | | 160 | | | | | 165 | | | | | 170 | | |
| AAG | AAG | TGG | TTT | CAA | GGA | ACT | GCA | GAT | GCT | GTG | AGA | CAA | TTT | ACC | TGG | 697 |
| Lys | Lys | Trp | Phe | Gln | Gly | Thr | Ala | Asp | Ala | Val | Arg | Gln | Phe | Thr | Trp | |
| | | | 175 | | | | | 180 | | | | | 185 | | | |

Figure 1-3

```
ATA TTT GAG GAT GCC AAG AAT ATA AAC GTC GAG AAT GTA TTG ATC TTG    745
Ile Phe Glu Asp Ala Lys Asn Ile Asn Val Glu Asn Val Leu Ile Leu
    190                 195                 200

GCG GGA GAT CAT TTA TAT CGA ATG GAT TAC ATG GAC CTA TTG CAG AGT    793
Ala Gly Asp His Leu Tyr Arg Met Asp Tyr Met Asp Leu Leu Gln Ser
    205                 210                 215

CAC GTT GAT AGA AAT GCC GAT ATT ACA GTT TCG TGT GCT GCC GTT GGT    841
His Val Asp Arg Asn Ala Asp Ile Thr Val Ser Cys Ala Ala Val Gly
    220                 225                 230                 235

GAC AAC CGC GCA TCT GAT TAT GGA TTG GTC AAG GTA GAC GAC AGA GGC    889
Asp Asn Arg Ala Ser Asp Tyr Gly Leu Val Lys Val Asp Asp Arg Gly
            240                 245                 250

AAC ATC ATA CAA TTT TCA GAA AAA CCG AAA GGC GCT GAT CTG AAA GCA    937
Asn Ile Ile Gln Phe Ser Glu Lys Pro Lys Gly Ala Asp Leu Lys Ala
            255                 260                 265

ATG CAA GTA GAT ACT TCT CGT CTT GGG TTG TCG CCA CAA GAT GCA TTG    985
Met Gln Val Asp Thr Ser Arg Leu Gly Leu Ser Pro Gln Asp Ala Leu
    270                 275                 280

AAG TCG CCA TAT ATT GCA TCT ATG GGA GTT TAT GTG TTC AAG AAA GAT   1033
Lys Ser Pro Tyr Ile Ala Ser Met Gly Val Tyr Val Phe Lys Lys Asp
    285                 290                 295
```

Figure 1-4

```
GTT TTA CTC AAG CTT CTG AAA TGG AGG TAT CCT ACT TCT AAT GAC TTC    1081
Val Leu Leu Lys Leu Leu Lys Trp Arg Tyr Pro Thr Ser Asn Asp Phe
300             305                 310                 315

GGA TCC GAA ATC ATT CCT TCC GCT ATA AGA GAA CAC AAT GTC CAA GCA    1129
Gly Ser Glu Ile Ile Pro Ser Ala Ile Arg Glu His Asn Val Gln Ala
                320                 325                 330

TAC TTT TTC GGA GAC TAC TGG GAA GAT ATT GGA ACG ATA AAA TCC TTC    1177
Tyr Phe Phe Gly Asp Tyr Trp Glu Asp Ile Gly Thr Ile Lys Ser Phe
            335                 340                 345

TAC GAT GCT AAC CTC GCT CTT ACT GAA GAG AGT CCA AAG TTC GAG TTT    1225
Tyr Asp Ala Asn Leu Ala Leu Thr Glu Glu Ser Pro Lys Phe Glu Phe
        350                 355                 360

TAT GAT CCA AAA ACA CCG ATT TTC ACA TCT CCT GGA TTC CTA CCA CCA    1273
Tyr Asp Pro Lys Thr Pro Ile Phe Thr Ser Pro Gly Phe Leu Pro Pro
    365                 370                 375

ACA AAG ATT GAC AAC TCT CGG GTT GTG GAT GCC ATT ATC TCC CAT GGA    1321
Thr Lys Ile Asp Asn Ser Arg Val Val Asp Ala Ile Ile Ser His Gly
380                 385                 390                 395

TGT TTC CTG AGA GAT TGT ACA ATC CAA CAC TCC ATT GTA GGT GAA AGG    1369
Cys Phe Leu Arg Asp Cys Thr Ile Gln His Ser Ile Val Gly Glu Arg
            400                 405                 410
```

Figure 1-5

```
TCG CGT TTA GAT TAT GGC GTT GAG CTT CAG GAC ACT GTA ATG ATG GGA    1417
Ser Arg Leu Asp Tyr Gly Val Glu Leu Gln Asp Thr Val Met Met Gly
        415                 420                 425

GCT GAC TAT TAC CAA ACT GAA TCC GAA ATC GCT TCC CTA CTT GCA GAA    1465
Ala Asp Tyr Tyr Gln Thr Glu Ser Glu Ile Ala Ser Leu Leu Ala Glu
        430                 435                 440

GGG AAG GTC CCG ATT GGC ATC GGA AGG AAT ACC AAA GTT ATG GGA    1513
Gly Lys Val Pro Ile Gly Ile Gly Arg Asn Thr Lys Ile Lys Asn Cys
        445                 450                 455

ATT ATT GAC AAG AAT GCA AAA ATC GGG AAA GAA GTT GTC ATC GCG AAC    1561
Ile Ile Asp Lys Asn Ala Lys Ile Gly Lys Glu Val Val Ile Ala Asn
        460                 465                 470                 475

AAA GAA GGC GTT CAA GAT AGA TCG AAA GCA ACG ATA GAA GGA    1609
Lys Glu Gly Val Gln Asp Arg Ser Lys Ala Thr Ile Glu Asp Gly
        480                 485                 490

CGA TCA GGA ATC ACC ATC ATA ATG GAG AAA GCA ACG ATA GAA GAC GGA    1657
Arg Ser Gly Ile Thr Ile Ile Met Glu Lys Ala Thr Ile Glu Asp Gly
        495                 500                 505

ACT GTC ATA TAAACAATGG TTAGTAGTTA TTTCACGAGC TGGTTTCCGT A    1707
Thr Val Ile
        510
```

Figure 1-6

```
AAGCGCCGGA AGAAGCATTG CAAGGAACAC TCCCTCCCAT CTTTTGGGAT TGGTACAAAA   1767
TGTTATGTTG AATAGAGAAA GCTGCATGTG TAAAATAGGA GAGCTCTTTC ACTAGATGTA   1827
GAAATAGAAA TGAATAAATG ATGAAAGTGA AGATGCAGAA AAGTTAAATA AATGGAAGGG   1887
TTGAGTGTGT GAAGGTATCA AGTTTCTATA TCCTCTCCCT TGAAACTGCA AAGGACATGT   1947
TTTAAATTAT TGTATCACTT AATTATTGTT TTGAATGGGTG GTAATAAGCA TTATAATCAC   2007
TTATTTGCTT CAAAAAAAAA AAAAA                                         2032
```

Figure 2-1

Bt2A pea sequence

```
TTTTTTTTTT GTTTGTCTTT CATTGCAGCA GAGCTTGTCT TTGAGACCGG ACACTGTCAG    60

TTCATACCTC CAAAAGCCAT ATG GCG TCA ATG GCT GCG ATC GGT GTT CTC       110
                      Met Ala Ser Met Ala Ala Ile Gly Val Leu
                        1               5                  10

AAA GTG CCG CCT TCC TCC TCC TCC TCC TCT TCT TCA TCT TCT TCT TCA     158
Lys Val Pro Pro Ser Ser Ser Ser Ser Ser Ser Ser Ser Ser Ser Ser
                 15                  20                  25

TCC AAA GCC ATT GCA CGC AAC CTC TCA TTC ACT TCA TCA CAG CTC TGT     206
Ser Lys Ala Ile Ala Arg Asn Leu Ser Phe Thr Ser Ser Gln Leu Cys
             30                  35                  40

GGT GAT AAG ATT TTC ACT GTT TCA GGA ACA AGA AGA AGT TCT GGT AGA     254
Gly Asp Lys Ile Phe Thr Val Ser Gly Thr Arg Arg Ser Ser Gly Arg
         45                  50                  55

AAC CCT TTC ATT GTT TCT CCC AAG GCT GTT TCT GAT TCC AAA AAC TCT     302
Asn Pro Phe Ile Val Ser Pro Lys Ala Val Ser Asp Ser Lys Asn Ser
     60                  65                  70

CAA ACT TGT CTT GAT CCA GAT GCT AGC CGA AGT GTT CTT GGC ATT ATA     350
Gln Thr Cys Leu Asp Pro Asp Ala Ser Arg Ser Val Leu Gly Ile Ile
 75                  80                  85                  90
```

Figure 2-2

```
CTT GGA GGT GCT GGG ACG CGT CTT TAT CCG TTG ACA AAG CGG    398
Leu Gly Gly Ala Gly Thr Arg Leu Tyr Pro Leu Thr Lys Arg
            95                     100                105

GCG AAA CCA GCT GTT CCT CTT GGA GCA AAC TAT CCG TTG ATT GAC ATC    446
Ala Lys Pro Ala Val Pro Leu Gly Ala Asn Tyr Pro Leu Ile Asp Ile
                110                 115                 120

CCT GTT AGC AAC TGC CTA AAT AGC ATA TCA AAG ATC TAT GTC CTC    494
Pro Val Ser Asn Cys Leu Asn Ser Ile Ser Lys Ile Tyr Val Leu
        125                 130                 135

ACA CAA TTC AAT TCG GCG TCC TTG AAT CGA CAC TTG TCC CGT GCG TAT    542
Thr Gln Phe Asn Ser Ala Ser Leu Asn Arg His Leu Ser Arg Ala Tyr
        140                 145                 150

GCG AGC AAC TTG GGT GGC TAC AAA AAT GAA GGT TTC GTT GAG GTT CTT    590
Ala Ser Asn Leu Gly Gly Tyr Lys Asn Glu Gly Phe Val Glu Val Leu
            160                 165                 170

GCC CAG CAG AGT CCT GAG AAT CCA AAT TGG TTC CAG GGC ACT GCG    638
Ala Gln Gln Ser Pro Glu Asn Pro Asn Trp Phe Gln Gly Thr Ala
            175                 180                 185

GAT GCG GTG AGG CAA TAT TTA TGG CTT TTT GAA GAG CAC AAT GTT TTG    686
Asp Ala Val Arg Gln Tyr Leu Trp Leu Phe Glu Glu His Asn Val Leu
            190                 195                 200
```

Figure 2-3

```
GAA TAC TTG GTT CTG GCG GGT GAC CAT TTG TAT CGA ATG GAT TAT GAG      734
Glu Tyr Leu Val Leu Ala Gly Asp His Leu Tyr Arg Met Asp Tyr Glu
205                             210                      215

AGA TTT ATA CAA GCA CAC AGG GAA AGT GAT GCT GAT ATC ACT GTT GCG      782
Arg Phe Ile Gln Ala His Arg Glu Ser Asp Ala Asp Ile Thr Val Ala
        220                     225              230

TCA TTG CCA ATG GAT GAA GCG CGT GCC ACT GCA TTC GGT CTA ATG AAA      830
Ser Leu Pro Met Asp Glu Ala Arg Ala Thr Ala Phe Gly Leu Met Lys
235                     240             245                 250

ATT GAT GAA GGG CGT ATA GTT GAG TTT TCA GAG AAG CCG AAA GGA          878
Ile Asp Glu Gly Arg Ile Val Glu Phe Ser Glu Lys Pro Lys Gly
        255                     260              265

GAA CAG TTG AAA GCT ATG AAG GTT GAT TAC ATT ACG ATT TTG GGT CTC GAC  926
Glu Gln Leu Lys Ala Met Lys Val Asp Tyr Ile Thr Ile Leu Gly Leu Asp
        270                     275              280

GAC GAG AGA TTG GCT AAG GAA ATG CCT TAC ATT GCT AGC ATG GGT ATA TAT  974
Asp Glu Arg Leu Ala Lys Glu Met Pro Tyr Ile Ala Ser Met Gly Ile Tyr
        285                     290              295

GTT GTC AGC AAA CAT GTG ATG CTA GAT CTG CTC CGC GAC AAG TTT CCT      1022
Val Val Ser Lys His Val Met Leu Asp Leu Leu Arg Asp Lys Phe Pro
300                  305                     310
```

Figure 2-4

```
GGT GCA AAC GAC TTT GGT AGC GAA GTT ATT CCT GGT GCG ACC GAG CTT      1070
Gly Ala Asn Asp Phe Gly Ser Glu Val Ile Pro Gly Ala Thr Glu Leu
315                 320                 325                 330

GGA TTG AGA GTG CAA GCT TAT TTA TAC GAT TAC TGG GAA GAC ATT          1118
Gly Leu Arg Val Gln Ala Tyr Leu Tyr Asp Tyr Trp Glu Asp Ile
            335                 340                 345

GGT ACG ATT GAG GCT TTC TAT AAT GCA AAT CTG GGA ATC ACC             1166
Gly Thr Ile Glu Ala Phe Tyr Asn Ala Asn Leu Gly Ile Thr Lys Lys
        350                 355                 360

CCT GTG CCA GAT TTT AGT TTC TAT GAC CGT TCA TCT CCA ATC TAC ACC      1214
Pro Val Pro Asp Phe Ser Phe Tyr Asp Arg Ser Ser Pro Ile Tyr Thr
365                 370                 375

CAA CCT CGA TAT TTG CCT CCC TCT AAG ATG CTT GAT GCT GAT              1262
Gln Pro Arg Tyr Leu Pro Pro Ser Lys Met Leu Asp Ala Asp
380                 385                 390

GAT AGT GTT ATT GGT GAA TGT GTA ATT AAG AAT TGC AAA ATC             1310
Asp Ser Val Ile Gly Glu Gly Cys Val Ile Lys Asn Cys Lys Ile His
395                 400                 405                 410

CAT TCT GTC GTT GGA CTG CGA TCT TGC ATA TCA GAA GGT GCA ATC ATT    1358
His Ser Val Val Gly Leu Arg Ser Cys Ile Ser Glu Gly Ala Ile Ile
        415                 420                 425
```

Figure 2-5

```
GAG GAC ACG TTG TTA ATG GGA GCA GAT TAT GAG ACG GAT GCT GAT      1406
Glu Asp Thr Leu Leu Met Gly Ala Asp Tyr Glu Thr Asp Ala Asp
                430                 435                 440

AGG AGG TTT TTG GCT GCT AAA GGC GGT GTT CCA ATC GGT ATT GGC AAG  1454
Arg Arg Phe Leu Ala Ala Lys Gly Gly Val Pro Ile Gly Ile Gly Lys
            445                 450                 455

AAT TCT CAT ATT AAA AGG GCA ATC ATT GAC AAG AAT GCT AGA ATT GGT  1502
Asn Ser His Ile Lys Arg Ala Ile Ile Asp Lys Asn Ala Arg Ile Gly
        460                 465                 470

GAC GAT GTC AAG ATT ATT AAC AGC GAC AAT GTG CAA GAA GCT GCA AGG  1550
Asp Asp Val Lys Ile Ile Asn Ser Asp Asn Val Gln Glu Ala Ala Arg
    475                 480                 485                 490

GAA ACG GAA GGT TAT TTC ATA AAA AGT GGT TAT ATT GTC ACA GTA ATC AAG  1598
Glu Thr Glu Gly Tyr Phe Ile Lys Ser Gly Tyr Ile Val Thr Val Ile Lys
495                 500                 505

GAT GCA TTA ATT CCA AGT GGA ACT GTC ATC TAAGAGCACT CTCTATTA      1646
Asp Ala Leu Ile Pro Ser Gly Thr Val Ile
            510                 515

CTGTTGCCTC ATGCAGCTGT GCAATGCAAC AACCCATTTT CACCGCTAGA AGGTGGTAAA  1706

AGAGCAGTTC CGCTTCCTCG TTGGTTTTCT GGTGCAATGT TATATTTGGT TCGCGAGTAT  1766
```

Figure 2-6

```
ATAGAGTAGA GGACCCTTTC TGAAGTCGCG ATGTAAATTT AATTTTATTC AGTCAAATAA   1826
ATGCTTCTTT GGTCTGCAGT GTCTGTGATG CATGTTCTTT TGCAGTTTAT CAAAGGTGTG   1886
GAATGATATC CACAGAAAAC AATGAAAAGT GATACAATAA AAGCCAGACA CTTAGCTTCT   1946
ATTGACGC                                                            1954
```

Figure 3-1

Bt2B pea cDNA sequence

```
CATTCACACA CTCTTTGTTC TAAACCACAC AAGAACAAAC ATAGTAACAT AAACACATAA                           60

AAACAAACAA CAGTTTCTTC A ATG TCT ATT GTT ACT TCA AGT GTT ATC                                111
                       Met Ser Ile Val Thr Ser Ser Val Ile
                       1               5               10

AAC GTT CCA CGT TCT TCT TCA TCA AAG AAC CTC TCA TTC TCA TCA                                159
Asn Val Pro Arg Ser Ser Ser Ser Lys Asn Leu Ser Phe Ser Ser
                15              20              25

TCA CAA CTC TCC GGT GAC AAG ATT CTT ACA GTT TCA GGT AAG GGT GCA                            207
Ser Gln Leu Ser Gly Asp Lys Ile Leu Thr Val Ser Gly Lys Gly Ala
            30              35              40

CCA AGA GGA AGA TGC ACC CGC AAG CAT GTG ATT GTT ACT CCT AAA GCT                            255
Pro Arg Gly Arg Cys Thr Arg Lys His Val Ile Val Thr Pro Lys Ala
            45              50              55

GTT TCT GAT TCA CAG AAC TCT CAA ACT TGC CTT GAT CCT GAT GCT AGC                            303
Val Ser Asp Ser Gln Asn Ser Gln Thr Cys Leu Asp Pro Asp Ala Ser
            60              65              70

AGA AGT GTG CTT GGA ATT ATA CTT ATT GGA GGT GGT GCT GGT ACT CGT CTT                        351
Arg Ser Val Leu Gly Ile Ile Leu Ile Gly Gly Gly Ala Gly Thr Arg Leu
75              80              85              90
```

Figure 3-2

```
TAT CCA ACC AAG AGA GCA AAA CCT GCT GTT CCT CTT GGA GCT           399
Tyr Pro Thr Lys Arg Ala Lys Pro Ala Val Pro Leu Gly Ala
        95                 100                 105

AAC TAT AGA CTC ATT GAT CCT GTT AGC AAT TGC TTG AAT AGC AAC       447
Asn Tyr Arg Leu Ile Asp Pro Val Ser Asn Cys Leu Asn Ser Asn
            110                 115                 120

ATT TCT AAG TAT GTT CTT ACT CAA TTC AAT TCC GCC TCA CTC AAT       495
Ile Ser Lys Tyr Val Leu Thr Gln Phe Asn Ser Ala Ser Leu Asn
        125                 130                 135

CGA CAT CTT TCT CGC GCT TAT GCG AGT AAT TTG GGT TAC AAA AAT       543
Arg His Leu Ser Arg Ala Tyr Ala Ser Asn Leu Gly Tyr Lys Asn
    140                 145                 150

GAG GGT TTT GTT GAA GTT CTT GCT CAG CAA AGT CCT GAG AAT CCT       591
Glu Gly Phe Val Glu Val Leu Ala Gln Gln Ser Pro Glu Asn Pro
    155                 160                 165                 170

AAT TGG TTT CAG GGT ACT GCA GAT GCT GTG AGG CAA TAT TTA TGG CTT   639
Asn Trp Phe Gln Gly Thr Ala Asp Ala Val Arg Gln Tyr Leu Trp Leu
        175                 180                 185

TTT GAA GAG CAT AAT GTT TTG GAG TAC TTA ATT CTG GCG GGT GAC CAT   687
Phe Glu Glu His Asn Val Leu Glu Tyr Leu Ile Leu Ala Gly Asp His
            190                 195                 200
```

Figure 3-3

```
TTG TAT CGA ATG GAT TAT GAG AAA TTT ATC CAA GCA CAT AGG GAA TCT      735
Leu Tyr Arg Met Asp Tyr Glu Lys Phe Ile Gln Ala His Arg Glu Ser
        205                 210                 215

GAT GCT GAT ATC ACC GTG GCT GCG TTG CCA ATG GAT GAA AAG CGT GCA      783
Asp Ala Asp Ile Thr Val Ala Ala Leu Pro Met Asp Glu Lys Arg Ala
        220                 225                 230

ACT GCT TTC GGT TTG ATG AAG ATC GAT GAA GAG GGG CGT ATA ATT GAG      831
Thr Ala Phe Gly Leu Met Lys Ile Asp Glu Glu Gly Arg Ile Ile Glu
        235                 240                 245             250

TTT GCA GAA AAG CCG AAA GGA GAA CAG TTG AAA GCT ATG AAG GTT GAT      879
Phe Ala Glu Lys Pro Lys Gly Glu Gln Leu Lys Ala Met Lys Val Asp
                255                 260                 265

ACT ACG ATT TTA GGT GAT CTT GAC GAA CAG AGA GCG AAA GAA ATG CCT TTT  927
Thr Thr Ile Leu Gly Asp Leu Asp Glu Gln Arg Ala Lys Glu Met Pro Phe
                270                 275                 280

ATT GCT AGC ATG GGT ATA TAT GTT GAT GAT AGC AAA AAT GTG CTA GAC      975
Ile Ala Ser Met Gly Ile Tyr Val Asp Asp Ser Lys Asn Val Leu Asp
        285                 290                 295

CTT CTC CGC GAC AAG TTT CCC GGT GCA AAT GAC TTT GGG AGT GAA GTG      1023
Leu Leu Arg Asp Lys Phe Pro Gly Ala Asn Asp Phe Gly Ser Glu Val
        300                 305                 310
```

Figure 3-4

| | | | | | | | | | | | | | | | | |
|---|---|---|---|---|---|---|---|---|---|---|---|---|---|---|---|---|
| ATT | CCT | GGT | GCT | ACT | TCT | GTT | GGA | ATG | AGA | GTG | CAA | GCT | TAC | TTA | TAT | 1071 |
| Ile | Pro | Gly | Ala | Thr | Ser | Val | Gly | Met | Arg | Val | Gln | Ala | Tyr | Leu | Tyr | |
| 315 | | | | | 320 | | | | | 325 | | | | | 330 | |
| GAT | GGC | TAC | TGG | GAA | GAC | ATT | GGT | ACC | ATT | GAG | GCT | TTC | TAT | AAT | GCA | 1119 |
| Asp | Gly | Tyr | Trp | Glu | Asp | Ile | Gly | Thr | Ile | Glu | Ala | Phe | Tyr | Asn | Ala | |
| | | | | 335 | | | | | 340 | | | | | 345 | | |
| AAT | CTT | GGA | ATC | ACC | AAA | AAG | CCT | GTG | CCT | GAT | TTC | AGT | TTC | TAT | GAT | 1167 |
| Asn | Leu | Gly | Ile | Thr | Lys | Lys | Pro | Val | Pro | Asp | Phe | Ser | Phe | Tyr | Asp | |
| | | 350 | | | | | 355 | | | | | 360 | | | | |
| CGT | TCA | TCT | CCG | ATT | TAC | ACC | CAA | CCG | CGA | TAC | TTG | CCT | CCA | TCT | AAG | 1215 |
| Arg | Ser | Ser | Pro | Ile | Tyr | Thr | Gln | Pro | Arg | Tyr | Leu | Pro | Pro | Ser | Lys | |
| | | 365 | | | | | 370 | | | | | 375 | | | | |
| ATG | CTT | GAT | GCT | GAT | ATT | ACT | GAT | AGT | GTT | ATC | GGA | GAA | GGA | TGT | GTG | 1263 |
| Met | Leu | Asp | Ala | Asp | Ile | Thr | Asp | Ser | Val | Ile | Gly | Glu | Gly | Cys | Val | |
| 380 | | | | | 385 | | | | | 390 | | | | | | |
| ATT | AAG | AAC | TGC | AAG | ATT | ATT | TTC | CAC | TCT | GTG | GTC | GGG | CTG | CGA | TCT | 1311 |
| Ile | Lys | Asn | Cys | Lys | Ile | Ile | Phe | His | Ser | Val | Val | Gly | Leu | Arg | Ser | |
| 395 | | | | | 400 | | | | | 405 | | | | | 410 | |
| ATA | TCA | GAA | GGT | GCA | ATT | ATT | GAA | GAC | ACT | TTG | TTA | ATG | GGG | GCA | GAT | 1359 |
| Ile | Ser | Glu | Gly | Ala | Ile | Ile | Glu | Asp | Thr | Leu | Leu | Met | Gly | Ala | Asp | |
| | | | | 415 | | | | | 420 | | | | | 425 | | |

Figure 3-5

| TAT | TAC | GAG | ACA | GAA | GCT | GAT | AAA | AGG | TTT | TTG | GCT | AAA | GGC | AGT | 1407 |
|---|---|---|---|---|---|---|---|---|---|---|---|---|---|---|---|
| Tyr | Tyr | Glu | Thr | Glu | Ala | Asp | Lys | Arg | Phe | Leu | Ala | Lys | Gly | Ser | |
| | | | 430 | | | | | 435 | | | | | 440 | | |

| GTT | CCA | ATT | GGT | ATC | GGC | AAA | AAC | TCG | CAT | ATC | AAA | AGA | GCA | ATT | GTT | 1455 |
|---|---|---|---|---|---|---|---|---|---|---|---|---|---|---|---|---|
| Val | Pro | Ile | Gly | Ile | Gly | Lys | Asn | Ser | His | Ile | Lys | Arg | Ala | Ile | Val | |
| | | | | 445 | | | | | 450 | | | | | 455 | | |

| GAC | AAG | AAC | GCG | AGA | ATC | GGA | GAA | AAC | GTC | AAG | ATA | ATT | AAC | AGT | GAC | 1503 |
|---|---|---|---|---|---|---|---|---|---|---|---|---|---|---|---|---|
| Asp | Lys | Asn | Ala | Arg | Ile | Gly | Glu | Asn | Val | Lys | Ile | Ile | Asn | Ser | Asp | |
| | 460 | | | | | 465 | | | | | 470 | | | | | |

| AAT | GTT | CAA | GAA | GCT | GCT | AGG | GAA | ACA | GAA | GGC | TAT | TTC | ATC | AAA | AGC | 1551 |
|---|---|---|---|---|---|---|---|---|---|---|---|---|---|---|---|---|
| Asn | Val | Gln | Glu | Ala | Ala | Arg | Glu | Thr | Glu | Gly | Tyr | Phe | Ile | Lys | Ser | |
| 475 | | | | | 480 | | | | | 485 | | | | | 490 | |

| GGG | ATC | GTC | ACA | ATA | ATC | AAG | GAT | GCC | TTG | ATT | CCT | AGT | GGA | ACT | GTC | 1599 |
|---|---|---|---|---|---|---|---|---|---|---|---|---|---|---|---|---|
| Gly | Ile | Val | Thr | Ile | Ile | Lys | Asp | Ala | Leu | Ile | Pro | Ser | Gly | Thr | Val | |
| | | 495 | | | | | 500 | | | | | 505 | | | | |

| ATA | TAGAAGACTG | AAACTCATCT | TTTGTTTCAT | AATGGTGAGT | GAGACTTTGA | 1652 |
|---|---|---|---|---|---|---|
| Ile | | | | | | |

Figure 3-6

```
AGTTCATGTT GCATGATATA TTTATTTTTC GATAAAGGCT TGTAAATAAT AGCTGAAGAG  1712
AGAACCTTCT TGTGTTTTGG AAACTAGTAC TGGTAAAGTT TGTTGATCAA TTGAATAAAA  1772
GTCGTTTTAT TTTCCACCTC TAAAAAAAAA AAAAAAAAAA AA                    1814
```

Figure 4-1

Panel A: Nucleotide sequence of the 5' end of pSS1 (SEQ ID NO:7)

```
GATCAAACCT GCTTCTTTTT CTGCTATTCT TACTTCAGAT GACCCCAAAG GTTCCCTGGT    60
AAACTCAGTT TCATTCTGGG TTTCACTTTT TGCTTCCAAT TCTGAAAAAA AGAAAGACTT   120
TTTTTCCTC CCATTATATG ACATAACTTT TTTATGTTAA TTATTTTGCT ACATTGTTT    180
GGTATATGAT TATGATTATG ATTATGATTT TGAGTGTATG TTTTGAAATT CAGAATTTGC   240
AAGTGCCTTC ATTTCTGAGA CTAAGAGCTG ATCCAAAAAA TGTGATTTCC AT          292
```

Panel B: Nucleotide sequence of the Pst I deletion of pSS1 (SEQ ID NO:8)

```
CTGCAGATGC TGTGAGACAA TTTACCTGGA TATTTGAGGT AGACAAACGA TTTTCGTTGT    60
TGTTGTTGTA TATACATTTT GATAAATAAT AGATTCGTTT GTTCTCATTT TTGAGCTTGT   120
CAATAAGTAA TAGATTGTTT GTGGTAGGAT GCCAAGAATA TAAACGTCGA GAATGTATTG   180
ATCTTGGCGG GAGATCATTT ATATCGAATG GATTACATGG ACCTATTGCA GGTATACTGT   240
GAATGTTTTG TAGAGTAGAT TGTTTTTCAT TTCATGTTCT AGAGTTTTCT GATTCATCTA   300
TATAACAAAT TAACAGAGTC ACGTTGATAG AAA                                333
```

Figure 4-2

Panel C: Nucleotide sequence of the BamHI deletion of pSS1 (SEQ ID NO:9)

```
GGATCCGAAA TCATTCCTTC CGCTATAAGA GAACACAATG TCCAAGTAAG AGGAATTCTG    60
ATAAATATAT CTGCTTACAA ATGTTTTTTT TCATTTCACA AGATTTTTAT CTGCCATCTA   120
TNTTTTTGC  AGGCATACTT TTTCGGAGAC TACTGGGAAG ATATTGGAAC GATAAAATCC   180
TTCTACGATG CTAACCTCGC TCTTACTGAA GAGGTAGGTT CAAGAATTTT TCTAGTGTTC   240
TTGTTCAGTT TTAGTTGATT GAAACTAAAT CTGCTATATG TTACTCTCTC GCAGAGTCCA   300
AAGTTCGAGT TTTATGATC                                                319
```

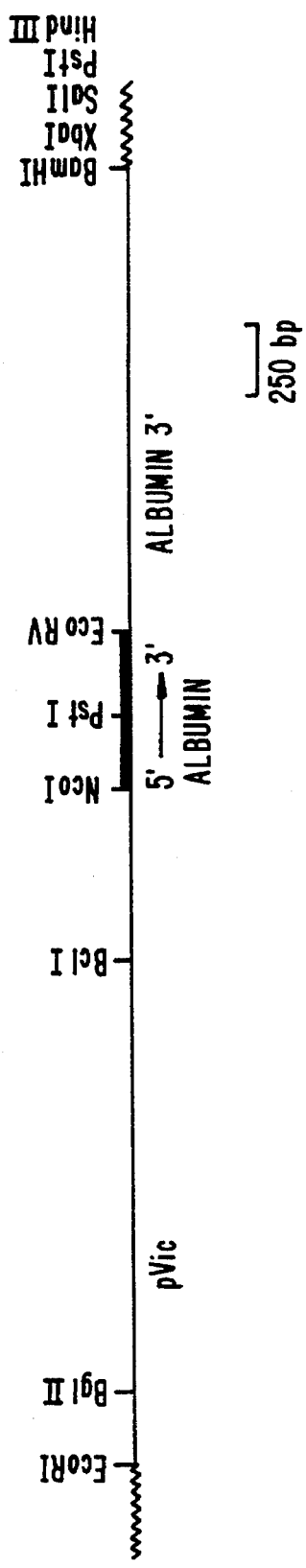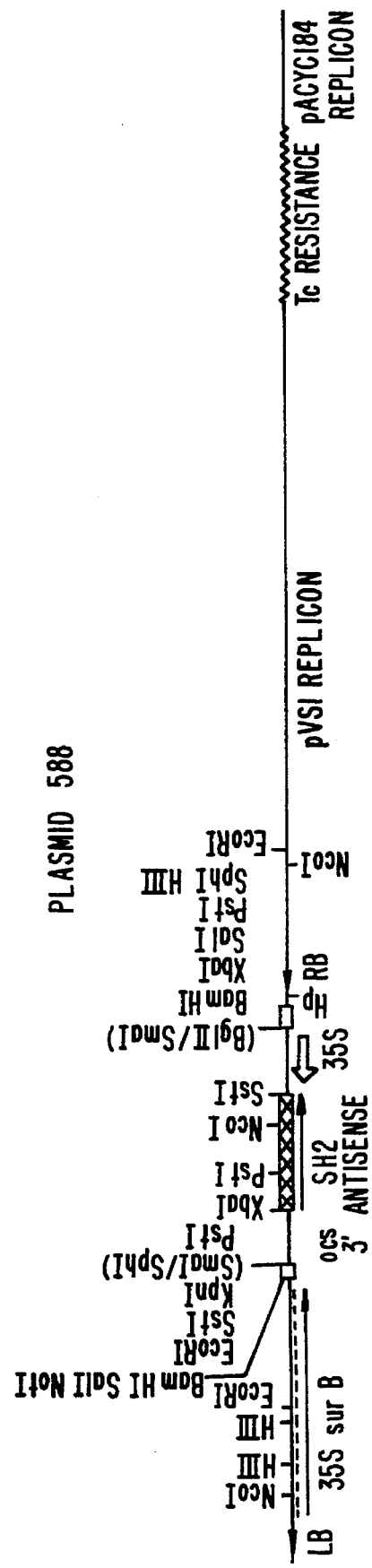
FIG. 7.
FIG. 8.

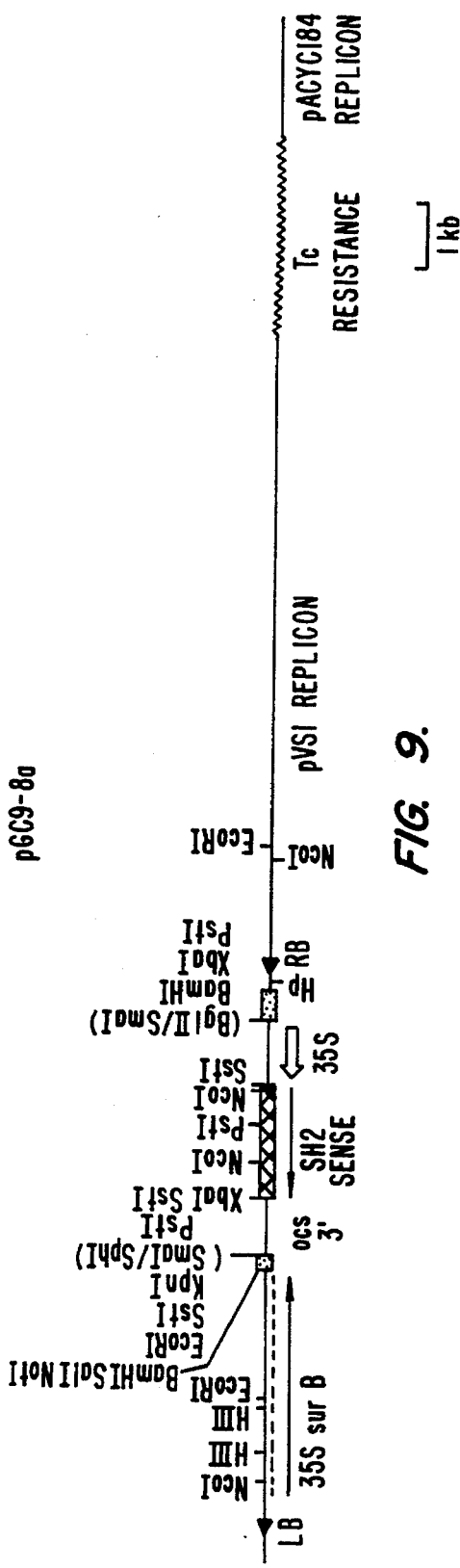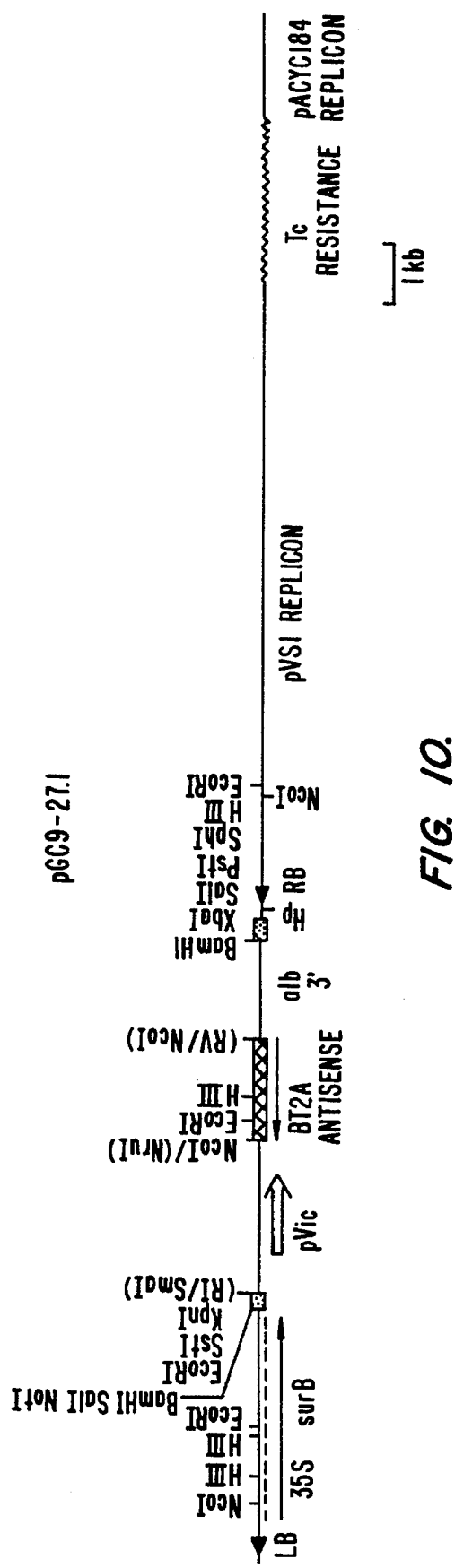

PEA ADP-GLUCOSE PYROPHOSPHORYLASE SUBUNIT GENES AND THEIR USES

FIELD OF THE INVENTION

The present invention relates generally to methods for genetically altering higher plant materials and changing their phenotype in regard to starch and sucrose biosynthesis. More particularly it relates to affecting the sucrose and starch content of edible plants, especially peas. The garden pea (Pisum sativum L.) is a commercially important food crop and the seeds of the garden pea ("peas")are widely consumed. Sweetness (e.g., sucrose content) in peas is generally prized by consumers, who perceive sweeter peas as having a better flavor.

As with any valuable plant species, breeders have long used conventional cross-breeding techniques to improve existing varieties and create new cultivars. While improvements have been achieved, cross-breeding techniques are laborious and slow because of the time required to breed and grow successive plant generations. Furthermore, certain phenotypes may be impossible to obtain by conventional techniques. Thus, it would be desirable to utilize recombinant DNA technology to produce new pea varieties and cultivars in a controlled and predictable manner. Pea varieties producing sweeter, better tasting peas would be especially desirable.

Sweetness in crops, including peas, could conceivably be enhanced by manipulating expression of enzymes that affect sucrose and/or starch metabolism. Sugar and starch biochemistry are interrelated in plants (see, e.g., Preiss, J. (1991) *Oxford Surveys of Plant Molecular & Cell Biology* 7: 59–114, which is incorporated herein by reference). For example, in starch storage organs of some plants, it is believed that sucrose is broken down in the cytoplasm into fructose plus UDP-glucose by sucrose synthase. UDP-glucose is then converted into glucose-1-phosphate by UDP-glucose pyrophosphorylase. Once in the amyloplasts of storage organs, glucose-1-phosphate is converted to ADP-glucose by ADP-glucose pyrophosphorylase (ADPG-PPase). ADP-glucose is then utilized by starch synthase to add a glucopyranosyl residue to the non-reducing end of a glucan primer. An isoform of starch granule-bound enzyme has been implicated in the synthesis of amylose, the unbranched form of starch. Amylopectin, the branched form of starch, is formed by the combined actions of starch synthase and starch branching enzyme. Other reactions and pathways may be utilized by different organs in a plant (e.g., photosynthetic organs), or by different plant species. By changing the levels or activity of a component in a starch synthesis pathway (e.g., an enzyme or substrate) it may be possible to affect the levels of sugar or starch in the plant or plant organ. If such an approach was successful in pea plants, one result might be sweeter peas.

Enzymes that might be candidates for such intervention include sucrose synthase, starch-branching and starch-debranching enzymes, inorganic pyrophosphatase, sucrose phosphate synthase, cell-wall-bound invertase, vacuolar acid invertase, and ADP-glucose pyrophosphorylase (ADPG-PPase).

ADPG-PPase plays a pivotal role in controlling the rate of starch synthesis in both the chloroplasts of photosynthetic organs and the amyloplasts of storage organs. ADPG-PPase transcripts are abundant in starch-storing organs and ADPG-PPase activity has been reported in embryos, endosperm, cotyledons, fruits, tubers, roots, leaves, mesocarp, and etiolated seedlings. A description of ADPG-PPase can be found in Anderson, J. M., et al. (1990) in W. C. Park and M. E. Vayda (Eds.) *Molecular and Cellular Biology of the Potato*, C.A.B. International, Wallingford, UK, pp. 159–180, which is incorporated herein by reference.

ADPG-PPase has been purified from a number of plants (Preiss, J. (1991) *Oxford Surveys of Plant Molecular & Cell Biology* 7: 59–1141 & other refs.) and is a heterotetrameric enzyme composed of two different but evolutionarily-related subunits. In maize endosperm the two subunits are encoded by the BT2 and SH2 loci and this terminology is extended to the evolutionarily homologous genes of other plants. Thus, in pea plants, the ADPG-PPase heterotetramer is believed to consist of two BT2 polypeptides and two SH2 polypeptides.

BACKGROUND ART

ADPG-PPase has been studied in plants and has been purified (to varying degrees) from spinach, maize, potato, rice, wheat, pea and barley (See, e.g., Anderson, J. M. et al. (1990), supra; Kleczkowski, L. A., et al. *Plant Physiol.* 101: 179–186).

Complete or partial cDNAs for ADPG-PPase subunits have been cloned from wheat, corn, potato, rice, spinach and barley (See, e.g., Bhave, M. R. et al. (1990) *The Plant Cell* 2: 531–538; Bae, J. M. et al. (1990) *Maydics* 3:317–322; and Nakata, P. A. et al. (1991) *Plant Molecular Biology* 17:1089– 1093).

In potato tubers, antisense inhibition of ADPG-PPase reduces starch levels compared to wild-type (Müller-Röber, B., et al. (1992) *EMBO J.* 11: 1229–1238). In corn endosperm culture, antisense inhibition of ADPG-PPase reduces ADPG-PPase activity (W093/09237). Over-expression of an *E. Coli* ADPG-PPase regulatory mutant in transgenic tobacco calli, tomato leaves, and potato tubers results in increased starch production (Kishore, G. M. (1991) International patent application number PCT/US91/04036; Stark et al., *Science*, 258:287–292 (1992)).

In pea, ADPG-PPase has been localized to the chloroplast in leaves (Preiss, J. (1991) *Oxford Surveys of Plant Molecular & Cell Biology* 7: 59–114) and in pea seeds ADPG-PPase activity has been shown to coincide with starch synthesis during seed development (Turner, J. F. (1969) *Aust. J. Biol. Sci.*, 22:1145–1151).

The mutant rb locus confers on pea embryos a reduction in starch and an increase in sugars (Kooistra, E. (1962) *Euphytica* 11: 357–373), and is also associated with ten-fold reduced levels of ADPG-PPase activity (Smith, A. M., et al. (1989) *Plant Physiol.* 89: 1279–1284).

BRIEF DESCRIPTION OF THE FIGURES

FIG. 1 shows the nucleotide sequence and deduced amino acid sequence for the SH2 cDNA clone 108-2. (Seq. I.D. Nos. 1 and 2).

FIG. 2 shows the nucleotide sequence and deduced amino acid sequence for the BT2A cDNA clone. (Seq. I.D. Nos. 3 and 4).

FIG. 3 shows the nucleotide sequence and deduced amino acid sequence for the BT2B cDNA clone. (Seq. I.D. Nos. 5 and 6).

FIG. 4 shows regions of the SH2 φ1 genomic clone. Panel A corresponds to Seq. I.D. No. 7; Panel B corresponds to Seq. I.D. No. 8; Panel C corresponds to Seq. I.D. No. 9.

FIG. 7 shows the plasmid pVicA.
FIG. 8 shows plasmid 588.
FIG. 9 shows plasmid pGC9-8a.
FIG. 10 shows plasmid pGC9-27.1

SUMMARY OF THE INVENTION

Figure 5:
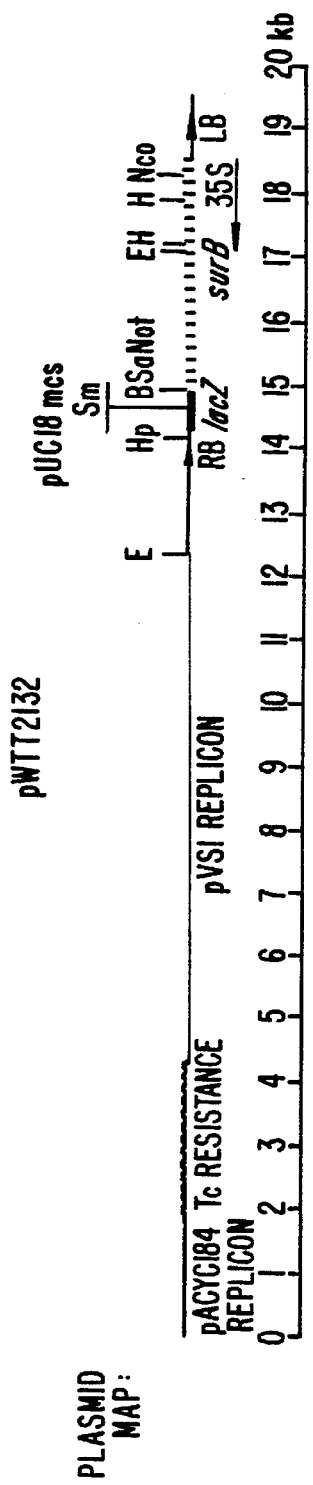
FIG. 5 shows the plasmid pWTT2132.

The present invention provides polynucleotides useful for affecting the sucrose and starch content of edible plants, especially the garden pea (*Pisum sativum* L.). These polynucleotides are useful for reducing ADP-glucose pyrophosphorylase (ADPG-PPase) expression in pea plants and other plants. The polynucleotides comprise isolated sequences encoding pea ADPG-PPase subunits SH2 and BT2 or parts thereof. Nucleic acid characteristics of clones encoding the two subunits, including the nucleotide and predicted amino acid sequences, are given in FIGS. 1–4 (Seq. I.D. Nos. 1, 3, 5, 7, 8, and 9).

The invention also provides DNA constructs comprising pea ADPG-PPase subunit nucleotide sequences. When introduced into a plant cell, these constructs are useful for sense and antisense suppression of ADPG-PPase SH2 and BT2 expression. Accordingly, the invention also provides plants, e.g., pea plants, comprising one or more of these constructs. By suppressing (or reducing) the expression of either ADPG-PPase subunit, or of both subunits, the sucrose content of a plant or plant part can be increased resulting in, e.g., sweeter peas.

The invention also provides DNA constructs encoding essentially full-length pea ADPG-PPase subunit polypeptides. When transformed into a plant cell, these constructs are useful for overexpressing ADPG-PPase in plant cells, resulting in increased levels of starch in a plant. Accordingly, the invention also provides for plants comprising these constructs

DETAILED DESCRIPTION OF THE INVENTION

The present invention is based on isolation and characterization of genes encoding pea ADPG-PPase subunits SH2 and BT2. Thus, the invention provides isolated polynucleotides having the sequences of pea ADPG-PPase subunits (i.e., the sequences provided in FIGS. 1–4 [Seq. I.D. Nos. 1, 3, 5, 7, 8, 9], complementary strands, homologous sequences from pea plants, and substantially identical sequences). "Isolated polynucleotides" refers to polynucleotides (e.g., RNA and DNA molecules) that are produced by recombinant DNA methods, chemically synthesized, or otherwise substantially separated from other DNAs and RNAs with which the polynucleotide is naturally associated (e.g., specific chromosomal sequences). Isolated polynucleotides include recombinant polynucleotides (i.e., a polynucleotide comprising at least two sequences not naturally associated, e.g., a sequence of eukaryotic origin and a sequence of prokaryotic origin, or two contiguous DNA sequences not naturally contiguous in the chromosome). The invention also encompasses genes encoding pea ADPG-PPase subunits SH2 and BT2 (e.g., including polymorphisms found in various varieties of garden pea and cognate genes in pea species other than garden pea, e.g., *Pisum arvense*, field pea). A "cognate" gene is an evolutionarily homologous gene that is closely related to the subject gene (i.e., it encodes a polypeptide homologous in sequence and function to the polypeptide encoded by the subject gene).

The invention also provides DNA constructs comprising all or part of the ADPG-PPase subunit sequences. A "construct" is a polynucleotide comprising nucleic acid sequences not normally associated in nature, such as a prokaryotic sequence and a eukaryotic sequence. Typically, a "construct" comprises a vector (e.g., of plasmid, viral, and/or episomal origin) and a sequence to be transcribed (i.e., a pea ADPG-PPase sequence).

In one embodiment, DNA constructs comprising all or part of the pea ADPG-PPase subunit DNA sequences are used to reduce or increase the levels of pea ADPG-PPase activity in some or all cells of a plant, especially a pea plant.

In one aspect of this embodiment, the invention provides DNA constructs for antisense expression ("antisense constructs"), as well as plants and plant cells comprising such constructs.

In another aspect of this embodiment, the invention provides DNA constructs for sense suppression ("sense suppression constructs"), as well as plants and plant cells comprising such constructs.

In a third aspect of this embodiment, the invention provides DNA constructs for expression of at least one pea ADPG-PPase subunit polypeptide ("overexpression constructs"), as well as plants and plant cells comprising such constructs.

In preferred embodiments, the invention provides pea plants comprising antisense constructs, where ADPG-PPase expression is reduced in at least one cell; pea plants comprising sense suppression constructs, where ADPG-PPase expression is reduced in at least one cell; and pea plants comprising overexpression constructs, where ADPG-PPase activity is increased in at least one cell. In most preferred embodiments, the invention provides pea plants comprising sense or antisense constructs comprising all or part of the sequence of a ADPG-PPase SH2 or BT2A subunit gene.

The polynucleotides of the present invention can be formed from a variety of different polynucleotides (e.g., genomic or cDNA, RNA, synthetic oligonucleotides and polynucleotides) as well as by a variety of different techniques.

The antisense suppression, sense suppression, and overexpression constructs of the present invention will share similar elements, which are well known in the art of plant molecular biology. For example, in each construct the DNA sequence of interest will preferably be operably linked (i.e., positioned to ensure the functioning of) to a promoter which allows the DNA to be transcribed (into an RNA transcript) and will comprise a vector which includes, e.g., a replication system.

Promoters (and other regulatory elements) may be heterologous (i.e., not naturally operably linked to a pea ADPG-PPase subunit gene). Promoters useful for expression in plants are known in the art and can be inducible, constitutive, tissue specific, derived from eukaryotes, procaryotes or viruses, or have various combinations of these characteristics. For example, and not limitation, useful promoters include the phytohemagglutinin (PHA) promoter; the pea vicilin promoter; constitutive promoters such as cauliflower mosaic virus promoter; regulated promoters such as ones associated with the ribulose-1,5-bisphosphate carboxylase genes, the chlorophyll binding protein genes, or the glycine-rich root protein genes; and SH2 gene promoters from the pea or other plants.

One useful promoter will be the pea ADPG-PPase SH2 subunit gene promoter. This promoter can be cloned according to methods that will be apparent to one of skill in the art. According to one protocol, for example, genomic DNA prepared from pea nuclei is partially digested with Sau3AI and then partially filled-in with dGTP and dATP. This DNA is ligated to lambda FixII (Stratagene) which has been digested with XhoI and partially filled-in with dCTP and dTTP. The ligation is packaged using Gigapack II (Stratagene) and plated on a suitable *E. coli* host strain (e.g., SRB(P2); Stratagene). Recombinant phage carrying the SH2 gene and its promoter are detected using the pea SH2 cDNA as a hybridization probe. Phage DNA isolated from positively-hybridizing plaques are digested with suitable restriction enzymes and hybridized with riboprobes prepared from the 5' end of the SH2 cDNA (e.g., clone 108-2). Approximately 2 kb of DNA upstream from the SH2 transcriptional unit and including the SH2 translational start site is subcloned into Bluescript (Stratagene). The ATG translational start site is mutagenized using the primer AGAAGCCATGGTAGTAACC (Seq. I.D. No. 10) to create an NcoI site. Digestion at this NcoI site enables the 5' upstream polynucleotide (the SH2 promoter) to be linked to pea ADPG-PPase subunit cDNA clones which have also been mutagenized at their translational start site to create NcoI sites (see, e.g., construct 472, pGC9-17NcoMuta and pGC9-8a descriptions).

In choosing a promoter it may be desirable to use a tissue-specific or developmentally regulated promoter that allows suppression or overexpression of ADPG-PPase in certain tissues without affecting ADPG-PPase expression in other tissues. For instance, promoters utilized in ADPG-PPase overexpression will preferably be tissue-specific. Overexpression in the wrong tissue, such as leaves, could be deleterious. Promoters from storage protein genes may be suitable choices, especially for overexpression in already starchy crops. These include patatin (potato tubers) (Rocha-Sosa, M., et al. (1989) *EMBO J.* 8: 23–29), convicilin, vicilin, and legumin (pea cotyledons) (Rerie, W. G., et al. (1991) *Mol. Gen. Genet.* 259: 148–157; Newbigin, E. J., et al. (1990) *Planta* 180: 461–470; Higgins, T. J. V., et al. (1988) *Plant Mol. Biol.* 11: 683–695), zein (maize endosperm) (Schernthaner, J. P., et al. (1988) *EMBO J.* 7: 1249–1255), phaseolin (bean cotyledon) (Sengupta-Gopalan, C., et al. (1985) *Proc. Natl. Acad. Sci. U.S.A.* 82: 3320–3324), phytohemagglutinin (bean cotyledon) (Voelker, T. et al. (1987) *EMBO J.* 6:3571–3577), β-conglycinin and glycinin (soybean cotyledon)(Chen, Z-L, et al. (1988) *EMBO J.* 7: 297– 302), glutelin (rice endosperm), hordein (barley endosperm) (Marris, C., et al. (1988) *Plant Mol. Biol.* 10: 359–366), glutenin and gliadin (wheat endosperm) (Colot, V., et al. (1987) *EMBO J.* 6: 3559–3564), and sporamin (sweet potato tuberous root) (Hattori, T., et al. (1990) *Plant Mol. Biol.* 14: 595–604). Differential screening techniques can be used to isolate promoters expressed at specific (developmental) times, such as during fruit development.

Selection of an appropriate vector is relatively simple, as the constraints are minimal. The minimal traits of the vector are that the desired nucleic acid sequence be introduced in a relatively intact state. Thus, any vector which will produce a plant carrying the introduced DNA sequence should be sufficient. Also, any vector which will introduce a substantially intact RNA which can ultimately be converted into a stably maintained DNA sequence should be acceptable.

Thus, suitable vectors include the Ti plasmid vectors, shuttle vectors designed merely to maximally yield high numbers of copies, episomal vectors containing minimal sequences necessary for ultimate replication once transformation has occurred, transposon vectors, homologous recombination vectors, mini-chromosome vectors, and viral vectors, including the possibility of RNA forms of the gene sequences. The selection of vectors and methods to construct them are commonly known to persons of ordinary skill in the art and are described in general technical references (e.g., Sambrook et al. *Molecular Cloning, A Laboratory Manual, Second Edition,* Cold Spring Harbor Laboratory Press, 1989, Vols. 1–3 [hereafter called "Sambrook"], which is incorporated herein by reference).

However, any additional attached vector sequences which will confer resistance to degradation of the nucleic acid fragment to be introduced, which assist in the process of genomic integration or which provide a means to easily select for transformed cells or plants are advantageous and greatly decrease the difficulty of selecting useable transgenotes (the term "transgenote" refers to the immediate product of the transformation process and to resultant whole transgenic plants). Commonly, expression vectors will contain selection markers, e.g., tetracycline resistance, hygromycin resistance, or chlorsulfuron resistance, to permit detection and/or selection of those cells transformed with the desired DNA sequences (see, e.g., U.S. Pat. No. 4,704,362, which is incorporated herein by reference).

Useful vectors may be capable of stable extrachromosomal maintenance in an appropriate cellular host or may be integrated into a host genome. The vectors may include sequences which allow for insertion into a host, such as transposon sequences, lysogenic viral sequences, retroviral sequences, or the like. In any case, useful vectors are typically replicable in the host organisms either as episomes or as an integral part of the host chromosomal DNA.

Useful vectors will usually contain sequences that allow replication in, e.g., a prokaryotic host useful for cloning the DNA sequences of the present invention. The most commonly used prokaryotic hosts are strains of *Escherichia coli,* although other prokaryotes, such as *Bacillus subtilis* or Pseudomonas may also be used, as is well known in the art. Useful vectors may also contain other sequence elements useful for cloning (e.g., useful restriction sites) or expression (e.g., enhancer sequences).

When the purpose of the construct is to provide for overexpression of an ADPG-PPase subunit, polynucleotides of the present invention will be cloned in the sense orientation into expression vectors so that they are expressed as essentially full length polypeptides (i.e., the RNA transcripts can be translated). Useful expression vectors are well known in the art and are readily available. Expression vectors typically include polyadenylation sites and translation regulatory sequences (e.g., translation start sites) and may also include introns and splice sites, enhancer sequences (which can be inducible, tissue specific or constitutive), and 5' and 3' regulatory and flanking sequences. Since ADPG-PPase is a plastid-localized enzyme, overexpression of this enzyme requires a plastid transit sequence for proper sub-localization. Retention of the endogenous ADPG-PPase transit sequence is preferred, especially for overexpression in amyloplast-containing organs. However, in some cases it may be desirable to use transit sequences from maize granule-bound starch synthase (waxy) (Klösgen, R. B., et al. (1991) *Gen. Genet.* 225: 297– 304), or from chloroplast-targeted proteins such as the small subunit of ribulose bisphosphate carboxylase. Methods for overexpressing proteins are well known and are described in, e.g., Sambrook.

Antisense polynucleotides (e.g., RNA transcripts) complementary to all or part of a sequence shown in FIGS.

1–4 (Seq. I.D. Nos. 1, 3, 5, 7, 8, and 9) may be produced using antisense constructs. Such antisense RNA transcripts may include nucleotide substitutions, additions, deletions, or transpositions, so long as specific hybridization to the relevant target sequence corresponding to a sequence provided in FIGS. 1–4 (Seq. I.D. Nos. 1, 3, 5, 7, 8, and 9) is retained as a functional property of the polynucleotide. For general methods relating to antisense polynucleotides, see *Antisense RNA and DNA*, (1988), D. A. Melton, Ed., Cold Spring Harbor Laboratory, Cold Spring Harbor, N.Y., which is incorporated herein by reference). The use of antisense suppression in plants is described generally in van der Krol et al., (1990) Mol. Gen. Genet. 220:204–212, which is incorporated herein by reference.

When a DNA construct encoding a sense transcript having substantial identity to a pea ADPG-PPase subunit gene is expressed in a plant cell, plants can be selected in which expression of that gene is suppressed. Such sense transcripts will have a sequence identical or substantially identical to a sequence provided in FIGS. 1–4 (Seq. I.D. Nos. 1, 3, 5, 7, 8, and 9) with the usual substitution of T (thymine) in the DNA sequence with U (uracil) in the RNA transcript. The use of sense constructs that produce sense transcripts for sense suppression is described in various references, including Napoli et al. (1990) *Plant Cell*, 2:279–289, van der Krol et al. (1990) *Plant Cell*, 2: 291–99, U.S. Pat. No. 5,034,323, copending U.S. patent application Ser. No. 07/501,076, Smith et al. (1990), *Mol. Gen. Genet.* 224:477–481; Elkind et al. (1990), *Proc. Natl. Acad. Sci.* 87:9057–9061; Goring et al. (1991), *Proc. Natl. Acad. Sci.* 88:1770–1774; and Nasrallah et al. (1992), International Workshop on Molecular Control of Flower Development and Reproduction, Amsterdam, the disclosures of which are incorporated herein by reference.

It should be noted that to achieve sense suppression in plants the introduced (i.e., exogenous) transcript need not be "full-length" (e.g., see Zhong et al. (1992), *Plant Cell* 4:1575–1588). The introduced transcript will usually be at least 50 bases in length, more often at least 100 bases, even more often at least 200 bases and may be 500 or more bases in length. The length of the exogenous sense transcript can also be expressed as a percentage of the length of the endogenous transcript. The exogenous transcript will typically be at least about 5% as long as the endogenous transcript, more often at least about 10% as long, still more often at least about 20% as long, even more often at least about 50% as long. Successful sense suppression also does not require that the introduced transcript comprise a sequence identical to that of the target (i.e., endogenous) gene. Rather, an introduced transcript with substantial identity (or substantial similarity) to the endogenous gene is sufficient. Typically, the introduced transcript will have at least 60% nucleotide identity, more often at least 80% identity, still more often at least 85% identity, even more often at least 90% identity, still more often at least 95% identity, and most often at least 98% identity.

The percentage identity between two nucleotide sequences is a useful measure of their sequence similarity. Percentage sequence (or nucleotide) identity is typically calculated by determining the optimal alignment between two sequences and comparing the two sequences. For example an exogenous transcript used for sense suppression can be described as having a certain percentage of identity or similarity compared to a reference sequence (e.g., the corresponding endogenous sequence).

Optimal alignment of sequences may be conducted using the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci.* (*U.S.A.*) 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by inspection. The best alignment (i.e., resulting in the highest percentage of identity) generated by the various methods is selected. Typically these algorithms compare the two sequences over a "comparison window" (usually at least 18 nucleotides in length) to identify and compare local regions of sequence similarity, thus allowing for small additions or deletions (i.e., gaps). Additions and deletions are typically 20 percent or less of the length of the sequence relative to the reference sequence, which does not comprise additions or deletions (e.g., the pea SH2 cDNA sequence [Seq. I.D. No. 1] or a region thereof). It is sometimes desirable to describe sequence identity between two sequences in reference to a particular length or region (e.g., two sequences may be described as having at least 95% identity over a length of at least 500 basepairs).

The percentage of sequence identity is calculated by comparing two optimally aligned sequences over the region of comparison, determining the number of positions at which the identical nucleic acid base (e.g., A, T, C, G, or U) occurs in both sequences to yield the number of matched positions, and determining the number (or percentage) of matched positions as compared to the total number of bases in the reference sequence or region of comparison.

It should also be noted that it should be possible to suppress expression of both ADPG-PPase subunit polypeptides using a single sense suppression construct, by joining multiple sequences together to coordinately repress the subunit genes.

To achieve sense suppression, antisense suppression, or overexpression, it is necessary to introduce the appropriate construct into at least some cells of the target plant (e.g., by transformation). The transformation of plants in accordance with the invention may be carried out in essentially any of the various ways known to those skilled in the art of plant molecular biology. See, in general, *Methods in Enzymology* Vol. 153 ("Recombinant DNA Part D") 1987, Wu and Grossman Eds., Academic Press, incorporated herein by reference. As used herein, the term transformation means alteration of the genotype (including episomal genes) of a host plant by the introduction of a nucleic acid sequence. The nucleic acid sequence need not necessarily originate from a different source, but it will, at some point, have been external to the cell into which it is to be introduced.

Foreign nucleic acid (i.e., comprising the constructs provided by the invention) may be introduced into plant cells by microinjection, by using polyethylene glycol (Paszkowski et al., (1984) *EMBO J.* 3:2717–22), by electroporation (Fromm et al., (1985) *Proc. Natl Acad. Sci. U.S.A.* 82:5824), by high velocity ballistic penetration by small particles with the nucleic acid either within the matrix of small beads or particles, or on the surface (Klein et al., (1987) *Nature* 327:70–73), by using Cauliflower mosaic virus (CaMV) as a vector for introducing the foreign nucleic acid into plant cells (Hohn et al , 1982, "Molecular Biology of Plant Tumors," Academic Press, New York, pp 549– 560; Howell, U.S. Pat. No. 4,407,956), and by various other means known in the art.

A preferred method of introducing the nucleic acid segments into plant cells is to infect a plant cell, an explant, a meristem or a seed with Agrobacterium, in particular *Agrobacterium tumefaciens* or *Agrobacterium rhizogenes* transformed with the segment. While the wild-type *Agrobacterium rhizogenes* may be used, the *Agrobacterium tumefaciens* should be "disarmed," i.e., have its tumor-inducing activity removed, prior to use. Preferred *Agrobacterium tumefaciens* strains include LBA4404, as described by Hoekema et al. (1983) Nature, 303:179–180, and EHA101 as described by Hood et al. (1986) J. Bacteriol., 168:1291–1301. A preferred *Agrobacterium rhizogenes* strain is 15834, as described by Birot et al. (1987) Plant Physiol. Biochem., 25:323–325. Under appropriate conditions known in the art, the transformed plant cells are grown to form shoots, roots, and develop further into plants. The nucleic acid segments-can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., (1984) "Inheritance of Functional Foreign Genes in Plants," *Science*, 233:496–498; Fraley et al., (1983) *Proc. Natl. Acad. Sci. U.S.A.* 80:4803).

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without its transferring ability being affected. By removing the tumor-causing genes so that they no longer interfere, the modified Ti plasmid can then be used as a vector for the transfer of the gene constructs of the invention into an appropriate plant cell, such being a "disabled Ti vector".

There are presently at least three different ways to transform plant cells with Agrobacterium:

(1) co-cultivation of Agrobacterium with cultured isolated protoplasts, (2) transformation of cells or tissues with Agrobacterium, or (3) transformation of seeds, apices or meristems with Agrobacterium.

Method (1) requires an established culture system that allows culturing protoplasts and plant regeneration from cultured protoplasts. Method (2) requires (a) that the plant cells or tissues can be transformed by Agrobacterium and (b) that the transformed cells-or tissues can be induced to regenerate into whole plants. Method (3) requires regeneration or micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may be used in this invention.

Normally, regeneration will be involved in obtaining a whole plant from the transformation process. As noted, supra, the term "transgenote" refers to the immediate product of the transformation process and to resultant whole transgenic plants. The term "regeneration" as used herein, means growing a whole plant from a plant cell, a group of plant cells, a plant part or a plant piece (e.g., from a protoplast, callus, or tissue part).

Plant regeneration from cultural protoplasts is described in Evans et al., "Protoplast Isolation and Culture," *Handbook of Plant cell Cultures* 1:124–176 (MacMillan Publishing Co. New York 1983); M. R. Davey, "Recent Developments in the Culture and Regeneration of Plant Protoplasts," *Protoplasts*, (1983)—Lecture Proceedings, pp.12–29, (Birkhauser, Basal 1983); P. J. Dale, "Protoplast Culture and Plant Regeneration of Cereals and Other Recalcitrant Crops," *Protoplasts* (1983)—Lecture Proceedings, pp. 31–41, (Birkhauser, Basel 1983); and H. Binding, "Regeneration of Plants," *Plant Protoplasts* pp.21– 73, (CRC Press, Boca Raton 1985).

In a most preferred embodiment, transformation is carried out in pea plants according to the method of copending U.S. Pat. No. 5,286,635, the disclosure of which is herein incorporated by reference. According to this method, whole pea plants expressing the exogenous DNA sequence may be produced by rooting the shoot and subsequently planting the rooted shoot in soil. The pea plant material is transformed by incubation with Agrobacterium cells carrying the exogenous DNA sequence which typically includes a selectable plant marker gene as well as one or more genes to be expressed. Shoots are regenerated from the pea plant material and selected, typically by growth on a selection and regeneration medium which inhibits growth in the absence of the marker.

Parts obtained from the regenerated plant, such as flowers, pods, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences. Progeny and variants, and mutants of the regenerated plants are also included within the scope of this invention.

A "pod", as used herein, is an expanded ovary composed of one carpel (the seeds are attached to the carpel) A "seed", as used herein, consists of an embryo contained within a maternally-derived seed coat (the testa). During early stages of seed development in pea, the seed also contains a triploid endosperm An "embryo", as used herein, is made up of one (monocots) or two (dicots) cotyledons which make up the bulk of the embryo, a plumule, a radicle, a basal cell, and a suspensor cell. A "cotyledon", as used herein, is the first embryo seed leaf Identification, selection or confirmation of transgenotes will typically be based on an assay or assays. Transgenotes (e.g., transformed plants) can be screened by biochemical, molecular biological, and other assays. Various assays may be used to determine whether a particular plant, plant part, or transgenote cell shows an increase (i.e., overexpression) or reduction (i.e., suppression) of ADPG-PPase gene expression and/or enzyme activity or an increase or decrease in sugar or starch content. Typically the change in expression or activity of the transgenote will be compared to levels found in wild-type (e.g., untransformed) plants of the same type. Preferably, the effect of the introduced construct (transgene) on the level of expression or activity of the endogenous gene will be established from a comparison of sibling plants with and without the construct. SH2 and BT2 mRNA levels can be measured e.g., by Northern blotting, primer extension, ribonuclease protection, quantitative or semi-quantitative PCR (polymerase chain reaction), and other methods well known in the art (see, e.g., Sambrook). Protein (i.e., ADPG-PPase tetramer, and SH2 and BT2 polypeptide) can be measured in a number of ways including immunological methods (e.g., by ELISA or Western blotting). ADPG-PPase activity can be measured in various assays as described in Smith, A. M. (1990) in P. J. Lea (Ed.) Methods in Plant Biochemistry, Vol. 3. Academic Press, New York, pp. 93–102, which is incorporated herein by reference. Sugar content of a plant cell or tissue can be measured in a variety of ways including those described in Jones et al. (1977) *Plant Physiol.* 60: 379–383; Nelson et al. (1944) *J. Biol. Chem.* 153: 375–380; Van Handel (1968) *Anal. Biochem.* 22: 280–283; Kilburn et al. (1969) *Anal. Biochem.* 27: 555; MacRae et al. (1971) *Planta* 96: 101–108; and Haissig et al. (1979) *Physiol. Plant.* 47: 151–157. Following gelatinization and enzymatic hydrolysis to glucose (e.g., according to MacRae et al. (1971) *Planta* 96: 101–108, and Haissig et al. (1979) *Physiol. Plant.* 47: 151–157), starch can be assayed using the methods described, supra, for sugar.

Sucrose levels are preferably determined as set forth in the Examples below. Glucose and fructose levels are preferably determined using a spectrophotometric assay similar to the one described in the Examples below under "Starch Assays", except that glucose-6-phosphate dehydrogenase is initially omitted from the reaction. Following a 30 minute incubation at room temperature, the reaction is divided into three tubes. Tube 1 serves as the blank, of use when measuring low levels of glucose and fructose, such as those found in pea embryos, since the background absorbance at 340 nm can be significant. To Tube 2 is added 5 U/ml of *Leuconostoc mesenteroides* glucose-6-phosphate dehydrogenase and to tube 3 is added 5 U/ml of *Leuconostoc mesenteroides* glucose-6-phosphate dehydrogenase and 0.015 mg/ml of yeast phosphoglucose isomerase. Glucose levels are read from tube 2 and fructose levels are read as the increase in absorbance in tube 3 compared to tube 2.

ADPG-PPase activity assays are preferably based on coupling the formation of glucose-1-phosphate from ADP-glucose to NADH formation. ADPG-PPase assays are performed in 75 mMHEPES (pH 7.75), 5 mMMgCl$_2$, 1 mM 3-phosphoglycerate, 0.1 mg/ml BSA, 0.01 mM glucose-1,6-bisphosphate, 1.5 mMADP-glucose, 0.4 mM NAD+, 2 U/ml phosphoglucomutase, 2 U/ml glucose-6-phosphate dehydrogenase, and 10 to 100 µl per ml of extract. Following a one minute incubation at 28° C. ADPG-PPase assays are initiated by the addition of 10 µl of 75 mM sodium pyrophosphate to 500 µl of assay solution. Coupled reduction of NAD+ to NADH is followed spectrophotometrically at 340 nm against a blank cuvette lacking sodium pyrophosphate. The assay depends on the addition of pyrophosphate, ADP-glucose, and extract, and is linear with time and volume of crude extract assayed.

To circumvent the instability of ADPG-PPase in crude extracts in the above assay, small aliquots of the crude extract are first frozen at −80° C. ADPG-PPase activity in pods can be stabilized by extracting in the presence of the allosteric inhibitor, phosphate, 10% ethylene glycol, and the proteinase inhibitor, PMSF.

To measure ADPG-PPase activity in pea seeds, pea seeds are preferably coarsely ground in a Bosch coffee grinder, pulverized using a mortar and pestle, and then homogenized in extraction buffer (0.1M MOPS, pH 7.2; 5 mM MgCl$_2$; 1 mM EDTA; 5 mM DTT) using a dounce homogenizer. The extract is cleared by centrifuging at 27,000 g for ten minutes. 100 µl aliquots of the cleared supernatant are quick-frozen and stored at −70° C. Long-term storage at −70° C. results in only a 10% reduction in ADPG-PPase activity.

Protein concentrations of crude extracts used for ADPG-PPase activity assays are preferably determined using the Bio-Rad protein assay with bovine gamma globulin as the protein standard.

In order to determine the range of sugar and starch levels in peas, e.g., Sugar Snap peas, seeds are preferably collected at varying times post-anthesis and assayed for sugar and starch levels. Two seeds are assayed independently at each time point. Sucrose levels peak around 16 days post-anthesis-(dpa), and then rapidly decrease with increasing development. The results may also be plotted in terms of embryo weight. Glucose and fructose levels plotted against days post-anthesis and hexose levels (glucose plus fructose) plotted against embryo weight show that both glucose and fructose levels rapidly decrease during seed development. Sucrose is by far the major sugar present in seeds, and glucose levels are similar to but slightly higher than fructose levels.

Once a transgenic plant is produced having a desired characteristic, it will be useful to propagate the plant and, in some cases, to cross to inbred lines to produce useful hybrids.

In vegetatively propagated crops, the mature transgenic plants are propagated by the taking of cuttings or by tissue culture techniques to produce multiple identical plants for trialling, such as testing for production characteristics. Selection of desirable transgenotes is made and new varieties are obtained thereby, and propagated vegetatively for commercial sale.

In seed propagated crops, the mature transgenic plants may be self crossed to produce a homozygous inbred plant. The inbred plant produces seed containing the gene for the newly introduced trait. These seeds can be grown to produce plants that would produce the selected phenotype.

Various plants will be suitable targets for increasing sweetness or other phenotypic changes produced by transformation with the pea ADPG-PPase subunit genes. In particular, the sugar and starch content of various varieties of peas and other leguminous plants can be affected.

The phenotype of both the field pea (inedible) and the garden pea (edible) can be affected according to the instant invention, with edible garden peas being preferred. The edible garden peas include both edible pod cultivars (e.g., sugar pea and snap pea types) and inedible pod cultivars (e.g., freezing types). Examples of pea species that will be useful include *Pisum sativum, Pisum arvense,* and others listed in Gritton, E. T. et al. (1986) in J. Bassett (ed.) *Breeding Vegetable Crops,* AVI Publishing Co., Westport, pp. 283–319, which is incorporated herein by reference. Useful pea varieties and cultivars include sugar pea types such as Oregon Sugar Pod II, Snowbird, Dwarf Grey Sugar, Mammoth Melting Sugar, Dwarf White Sugar, DeGrace, Grijze Roodblond, Record, Rembrandt, Little Sweetie; snap pea types such as Sugar Snap, Sugar Daddy, Sugar Pop, Super Sugar Mel, Snappy, Bush Snapper, Early Snap, Sugar Bon, Sugar Anne; inedible-pod types-such as Madria Variety, Puget, Stivo, Alaska, Maestro, Century, Improved Laxton's Progress, Spring, Patriot, Olympia, Triplet, Sparkle, Lincoln, Alpine, Banquet, Green Arrow, Perfection Dark Seeded, Polaris, Little Marvel, Progress 9, Venus, Mars, Rondo, Alderman (Tall Telephone), Early Frosty, Greater Progress and other pea varieties and cultivars listed in standard references (e.g. Isaacson, R. T. (1993) Source List of Plants and Seeds, Anderson Horticultural Library, U. Minnesota p.185, which is incorporated herein by reference).

Many pea varieties or cultivars are expected to be genotypically very similar, especially if of the same type or class of pea (e.g., snap pea type). For instance, Sugar Snap and Sugar Daddy, being different cultivars, may have some polymorphic variations in DNA sequence. However, no differences in these two cultivars have been detected to date with ribonuclease protection or genomic Southern assays.

Other leguminous plants that will be useful targets for transformation by the pea ADPG-PPase subunit genes include edible soybeans, (i.e., of the genus Glycine, e.g., *Glycine max*); species of the genus Vigna, such as the cowpea (*V. unguiculata,* including *Vigna unguiculata* ssp. unguiculata); mung beans *Phaseolus aureus;* grams beans; rice beans; adzuki beans; chick pea or garbanzo (*Cicer arietinum*); the broad bean (*Vicia faba*); the tepary bean (*P. acutifolius*); Phaseolus beans, of the vulgaris (common bean), coccineus (scarlet runner) and lunatus (lima bean) species; peanut, including the cultivated species, *Arachis hypogaea;* the lentil plant (*Lens esculenta*); alfalfa (Medicago); clover (Trifolium); and Prosopis. Still other useful legumes include *Canavalia ensiformis* (jack bean); *Canavalia gladiata* (sword bean); *Lablab purpureus* (hyacinth bean); *Cyamopsis tetragonoloba* (cluster bean); *Lathyrus sativus* (chickling pea); *Dolichos biflorus* (horsegram); *cajanus cajan* (pigeon pea). Additional legumes can be found in standard references, e.g., Salunke, D. K. and B. B. Desai (1984) Post-harvest Biotechnology of Vegetables, Vol. I, CRC Press, Boca Raton, F1; and Handbook of Agriculture, published Sept. 1987 by Shri Thakur Das, Undersecretary, Indian Council of Agricultural Research, New Delhi, both of which are incorporated herein by reference.

The sugar and starch content of plants other than peas and other legumes may also be affected according to the instant invention, e.g., by expressing the genes of the invention in such other plants to enhance starch production. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon (e.g., *L. esculentum*), Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, and Datura.

The inbreds according to this invention can be used to develop new hybrids. In this method a selected inbred line is crossed with another inbred line to produce the hybrid. Methods for breeding and crossing plants are well known and are described, e.g., in Gritton, E. T. (1986) in J. Bassett (Ed.) *Breeding Vegetable Crops,* AVI Publishing Co., Westport, pp. 283–319.

BT2 and SH2 clones also find use as hybridization probes, e.g., to isolate their endogenous promoters. The BT2 promoter may be useful as a relatively constitutive promoter and the SH2 promoter may be useful as a sink-specific promoter.

RNA from peas transformed with BT2- and SH2-containing sense and antisense constructs can be assayed using BT2 and SH2 as hybridization probes. Cotyledons, leaves and pods-from transgenic plants can be assayed to determine the efficacy of antisense and sense suppression on ADPG-PPase RNA levels.

BT2 and SH2 clones can also be used as RFLP markers in breeding programs. Hybridization with BT2 and SH2 can be used either to follow segregation of the corresponding genes or to follow-segregation of linked traits.

BT2 and SH2 can be used as hybridization probes to follow BT2 and SH2 transcript levels during development, in different tissues, and during post-harvest storage.

The following experimental section is offered by way of example and not by limitation.

EXAMPLES

I. Cloning and Characterization of ADPG-PPase Subunit cDNAs

A. Preparation and screening of C. DNA Libraries i. RNA isolation

RNA was isolated from embryos of Sugar Snap pea at a stage 21–28 days post-anthesis ("dpa"). Sugar Snap peas used here and elsewhere in the Examples were grown from seed obtained from W. Atlee Burpee & Co., 300 Park Avenue, Warminster, Pa. 18974. Isolation was carried out according to Dunsmuir, P., et al. (1987). In S. Gelvin and R. Schilperoot (Eds.) *Plant Molecular Biology. Manual,* vol 9., Plenum, New York, pp. 45–59. The RNA was subjected to chromatography on oligo(dT)-cellulose (Maniatis, T., et al. (1982) Cold Spring Harbor Laboratories, New York) to isolate poly(A)+ RNA.

ii. Preparation of cDNA libraries

A cDNA library was made from the poly(A)+ RNA. First and second strand synthesis was performed using an Amersham cDNA synthesis kit. Oligo(dT) was used to prime synthesis of first strand cDNA off of 5 μg of poly(A)+ RNA. For methylation of internal EcoRI sites, double-stranded cDNA was brought up in 20 μl of EcoRI methylase buffer (50 mM Tris-Cl, pH 7.5; 1 mM EDTA; 5 mM DTT). 2 μl of 100 μM S-adenosyl-methionine (in 10 mM sodium acetate, pH 5.2) was added and methylation was begun by the addition of 40 U of EcoRI methylase (BioLabs). After a 30 minute incubation at 37° C. the enzyme was inactivated by a 15 minute heat treatment at 65° C. CDNA ends were blunt-ended by the addition of 2.5 μl of 0.1M $MgCl_2$, 2.5 μl of 0.2 mM each of dGTP, dATP, dCTP, and dTTP, and 5 U of DNA polymerase I (Pharmacia). After 10 minutes at room temperature, the - reaction was stopped by the addition of 2 μl of 0.25M EDTA and the reaction was deproteinized by extraction with phenol/chloroform followed by ethanol precipitation. The ethanol pellet was brought up in 25 μl STE (10 mM Tris-Cl, pH 7.5; 0.1M NaCl; 1 mM EDTA) and dNTPs and short cDNAs were removed by spinning through a Sephacryl $400 spin column (Promega). The flow-through was ethanol-precipitated and the pellet was brought up in 24 μl of water. Addition of phosphorylated EcoRI linkers d(CG-GAATTCCG) (Seq. I.D. No. 11), (Stratagene) was accomplished by adding 10 μl (5 μg) of linkers, 5 μl of 10 mMATP, 4 μl of 10x ligase buffer (0.5M Tris-Cl, pH 7.5; 0.1M $MgCl_2$; 0.1M DTT), and 7 μl (14 U) of T4 DNA ligase (Promega). After an overnight incubation at 15° C., the ligase was inactivated by a 15 minute incubation at 65° C. Excess linkers were then removed by addition of an equal volume of EcoRI restriction buffer (180 mM Tris-Cl, pH 7.5; 100 mM NaCl; 20 mM $MgCl_2$) and 80 U of EcoRI (Promega). After a 2 hour incubation at 37° C. the enzyme was inactivated by a 15 minute heat treatment at 65° C. The sample was ethanol precipitated, brought up in 20 μl TE (10 mM Tris-Cl, pH 8.0; 1 mM EDTA)-and size-fractionated on a 1.2% agarose gel in TAE (0.04M Tris-acetate; 0.002M EDTA). DNA greater than 600 bp was recovered by binding to an NA-45 DEAE membrane (Schleicher and Schuell) according to the instructions of the manufacturers, except that the N-butanol extraction step was omitted. The ethanol-precipitated pellet was brought up in 15 μl STE and put through a Sephacryl S400 spin column. The flow-through was ethanol precipitated and brought up in water. 30 ng of cDNA was then ligated to 1 μg of dephosphorylated EcoRI λgt10 arms (Promega) in a 10 μl reaction containing ligase buffer, 1 mM ATP, and 2 U of T4 DNA ligase (Promega). After an overnight incubation at 15° C. the DNA was packaged using Gigapack II Gold (Stratagene).

iii. Oligonucleotide Synthesis

The degenerate oligonucleotide [TTT(A/G)AT (G/A/T/C)GT(G/A/T/C)CC(A/G)A(T/C)(A/G)TC(T/C)TCCCA(A/G)TA (G/A/T/C)CC](Seq. I.D. No. 12) was synthesized on an Applied Biosystems 381 DNA synthesizer using β-cyanoethyl synthesis and purified over an Oligonucleotide Purification Cartridge (Applied Biosystems) as per instructions of the manufacturer. Oligonucleotides used in PCR were prepared in a similar fashion.

iv. Hybridization Conditions

C600 or C600 hfl strains of *E. coli* (in 10 mM $MgSO_4$) were infected for 15 minutes at 37° C. with packaged recombinant λgt10 phage and plated on LB plates (1% tryptone; 0.5% yeast extract; 0.5% NaCl; 0.1% glucose; 1.5% agar; pH 7) with NZY top agarose (0.5% NaCl; 0.2% $MgSO_4.7H_2O$; 0.5% yeast extract; 1% NZamine; 0.7% agarose). Phage were replica-plated on to Millipore 0.45 μM HA filters, lysed on Whatman paper soaked with denaturing solution (0.5M NaOH; 1.5M NaCl), neutralized with 1.5M NaCl/0.5M Tris-Cl, pH 7.5, soaked in 2 x SSC (1 x SSC = 0.15M NaCl; 0.015M sodium citrate, pH 7.0), and UV cross-linked. Filters were hybridized either with the degenerate oligonucleotide or with pea SH2, BT2A, or BT2B probes.

For hybridization with the degenerate oligonucleotide, filters were pre-hybridized and hybridized at 42° C. in 20% formamide hybridization solution [20% formamide; 6 x SSC; 5 x Denhardt's (50 x = 1% Ficoll, 1% polyvinylpyrrolidone, 1% BSA); 100 μg/ml salmon sperm DNA; 10% dextran sulphate; 1% SDS; 0.05M sodium phosphate, pH 6.8] and washed at 37° C. in 2 x SSC. The oligonucleotide used for hybridization was end-labeled with T4 polynucleotide kinase (Maxam, A. M. et al. (1980) *Methods in Enzymology* 65: 499–560).

v. Library Screening

The 30 nt-long degenerate oligonucleotide was made to a conserved region of ADPG-PPase based on the amino acid sequences for a rice seed BT2-like cDNA clone and an *E. coli* genomic clone (Preiss, J., et al., 1987, in Bruening, G., Harada, J., Kosuge, T., and Hollaender, A., (Eds.) *Tailoring Genes for Crop Improvement: An Agricultural Perspective*, Plenum Press, New York, pp. 133–152), and the unpublished nucleotide sequence of a maize endosperm SH2 cDNA clone (provided by Curt Hannah, Univ. of Florida). Evidence that this degenerate oligonucleotide could hybridize to pea ADPG-PPase transcripts was obtained by hybridizing the oligonucleotide to pea RNA. The 2.15 kb transcript that strongly hybridized to this oligonucleotide was unambiguously larger in size than 18S rRNA.

The degenerate oligonucleotide was used as a hybridization probe. The cDNA library screened was made from 21–28 dpa Sugar Snap embryos. Out of $3.4 \times 10^4$ cDNA clones screened on duplicate filters, 26 hybridizing clones were detected on both filters. Twenty-two of these clones proved positive on rescreening and seventeen of these clones were plaque-purified. Out of 13 clones that were partially characterized, 8 had BT2-like inserts and 5 had SH2-like inserts. Four of the BT2-like clones were partially sequenced and they all had BT2A inserts; five of the SH2-like clones were sequenced and they all had SH2 inserts.

To ensure that the degenerate oligonucleotide was not missing any additional classes of ADPG-PPase cDNAs, the Sugar Snap embryo cDNA library was rescreened at low stringency in duplicate with pea BT2A and SH2 probes. For hybridization with BT2A, BT2B, and SH2, filters were hybridized at 42° C. in 50% formamide hybridization buffer [50% formamide; 5 x SSC; 0.02M phosphate, pH 6.8; 1 x Denhardt's; 1% SDS; 100 μg/ml salmon sperm DNA; 10% dextran sulphate]. Low stringency washes were done at 50° C. in 1.5 x SSC/1% SDS and high stringency washes were done at 65° C. in 0.1 x SSC. The hybridization probes used were BT2A (710 bp HincII-HindIII coding region riboprobe), BT2B (330 bp coding/3'non-translated region HincII-EcoRI riboprobe), and SH2 (370 bp HindIII-HincII riboprobe). Nine positive clones hybridized with the SH2 probe and eight hybridized with the BT2A probe. No cross-hybridization was seen between SH2- and BT2A-hybridizing clones. When the filters were re-washed under high stringency conditions, all the SH2-hybridizing clones remained bound, but one of the BT2A-hybridizing clones washed off. This one clone hybridized to BT2B under high stringency conditions, and upon sequencing, turned out to have a BT2B insert. Thus, besides BT2A, BT2B, and SH2, no other major classes of ADPG-PPase transcripts are likely to be present in pea embryo.

The degenerate oligonucleotide was also used as a hybridization probe in a separate screen of 10,000 recombinant clones in a pea pod cDNA library; one positive clone was identified with an insert belonging to the BT2B class.

All of the BT2A clones isolated from the embryo cDNA libraries end at an internal EcoRI site approximately 180 nts from the end of the coding region. The missing 3' end of the transcript was obtained using the RACE protocol (Frohman, M. A., 1990, in M. A. Innis, D. H. Galfand, J. J. Sninsky, and T. J. White (Eds.) *PCR Protocols: A Guide to Methods and Applications*, Academic Press, San Diego, pp. 28–38). Using this procedure, two amplified fragments were obtained, 400 and 600 bp in length, differing only in the extent of 3'-non-coding sequence. Both amplified fragments begin at the same internal EcoRI site and encode the missing amino acids. Similarly, on Northerns the BT2A probe hybridizes to two RNAs differing in size by about 200 nts.

vi. Subcloning

DNA was prepared from plaque-purified clones by the method of Malik et al. (Malik, A. N., et al. (1990) *Nucleic Acids Res.* 18: 4031–4032). Inserts were isolated by electrophoresis on to NA-45 DEAE membrane (Schleicher and Schuell) and subcloned into Bluescript phagemids with the KS polylinker (Stratagene). Inserts subcloned into Bluescript (+) were given the notation A+ (e.g., $108_2$ A+) when their 5' ends were adjacent to the T7 promoter and B+ when their 5' ends were adjacent to the T3 promoter, e.g., 108-2(B+). Similarly, inserts subcloned into Bluescript (−) were given the notation A− when their 5' ends were adjacent to the T7 promoter and B− when their 5' ends were adjacent to the T3 promoter, e.g., (104 B−).

$108-2(B+)$ and $104(B-)$ were used, as described in the Examples below, in constructs for plant transformations.

B. Sequence Determination cDNA fragments to be sequenced were subcloned into the phagemid vector, Bluescript (Stratagene). Sequencing was done in both directions using commercially-supplied primers (Stratagene) and sequencing kits (Stratagene and USB) and using the dideoxy chain-termination method of Sanger et al. (1977) *Proc. Natl. Acad. Sci. U.S.A.* 74: 5463– 5467). Internal regions were sequenced using deletion derivatives.

The sequences of the cDNA clones are given in FIGS. 1–3. The SH2 cDNA clone 108-2 has been completely sequenced in both directions. According to primer extension results, 23 bp of sequence is missing from the 5' end of this clone. Four other SH2 cDNA clones have also been partially sequenced (11, 111-2, 111-3, and 111-5). Two different polyadenylation sites were identified from these sequences.

The BT2A cDNA clone 104 has been completely sequenced in both directions. According to primer extension results, 14 bp of sequence is missing from the 5' end of this clone. Five other BT2A cDNA clones have also been partially sequenced (Sweetie, 24Cl, 102, 104-2, and 104-3). All these clones end at an internal EcoRI site approximately 180 nucleotides from the 3' end of the coding region. The 3' end of BT2A was isolated using the RACE protocol (Frohman, M. A., 1990, Supra. Two sizes of fragments were amplified (0.4 and 0.6 kb). Sequencing was done on multiple independent inserts to detect any mutations that might have been generated during PCR amplification.

The BT2B cDNA clone from the embryo cDNA library has been completely sequenced in both directions. According to primer extension results, 12 bp of sequence is missing from the 5' end of this clone. One other BT2B cDNA clone (pod) has also been partially sequenced.

II. Isolation and Characterization of SH2 Genomic Clones

A. Preparation of Genomic Library

A partial Sau3AI Sugar Snap pea genomic DNA library was prepared in λDASH (Stratagene) following standard procedures (Maniatis, T., et al. (1982) Cold Spring Harbor Laboratories, New York).

B. SH2 genomic clone 600,000 independent recombinant phage were screened with a 32P-labeled riboprobe prepared from SH2 cDNA. One positive clone was detected. This clone, SH2 φ1, begins at nucleotide (nt) 262 of the SH2 sequence (see FIG. 4, panels A–C).

Phage DNA was prepared and the gene was mapped to a 5.5 kb SalI fragment. This fragment was cloned into the SalI site of Bluescript(+) to give pSS1, which was subsequently used for further mapping and sequencing. DNA sequence analysis across the 5' end confirmed that it is the SH2 genomic equivalent and begins within the 5' coding region 123 bp downstream of the ATG at the translational initiation site.

Three regions of the SH2 φ1 genomic clone have been sequenced from the subclone pSS1. Approximately 330 nts have been sequenced from the 5' end, including a 175 nt intron sequence (see FIG. 4, panel A). The second region sequenced (region B) starts at the PstI site of the SH2 sequence (nt 669) (see FIG. 4, panel B). Approximately 330 nts have been sequenced from this site, including two introns. The third region sequenced (region C) starts at the BamHI site of the SH2 sequence (nt 1082) (see FIG. 4, panel C). Approximately 320 nts have been sequenced from this site, including two introns. Except for the presence of 5 introns, no differences were found between the cDNA and genomic sequences.

III. Construction of Sense and Antisense Vectors

A. Precursor Vectors i. pWTT2132

The plasmid pWTT2132 (FIG. 5) contains DNA from the following sources:

a. *Escherichia coli* DNA in the pACYC184-derived part of the plasmid vector (Chang, A. C. Y. et al. (1979) *J. Bacteriol.* 134: 1141–1156), the lacZ α fragment of the β-galactosidase gene (Yanisch-Perron, C., et al. (1985) *Gene* 33: 103–119), and the tetracycline resistance (tetR) gene.

b. *Pseudomonas aeruginosa* DNA in the pVS1-derived part of the plasmid vector (Itoh, Y., et al.(1984) *Plasmid* 11: 206–220).

c. *Nicotiana tabacum* (tobacco) DNA in the coding sequence and the polyadenylation signals of the surB gene encoding chlorsulfuron (ALS) resistance (Lee, K. Y., et al.(1988) *EMBO J.* 7: 1241–1248).

d. Petunia var. Mitchell DNA in the cab22L leader region (Harpster, M. H., et al. (1988) *Mol. Gen. Genet.* 212: 182–190).

e. *Agrobacterium tumefaciens* octopine strain DNA in the left and right border regions of the T-DNA (van den Elzen, P., et al. (1985) *Plant Mol. Biol.* 5: 149– 154).

f. Cauliflower mosaic virus DNA in the 35S promoter that is directing expression of the surB gene (Lee, K. Y., et al. (1988) *EMBO J.* 7: 1241–1248) .

ii. JJ3572

Figure 6:
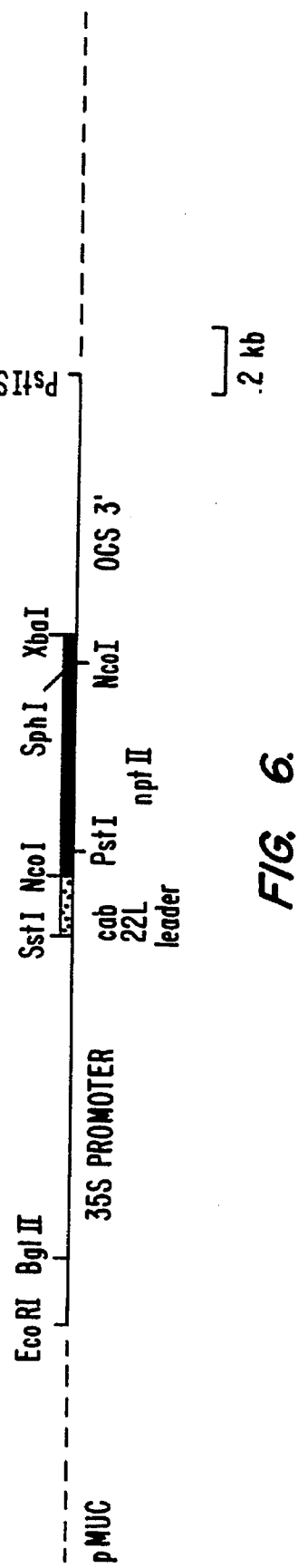
FIG. 6 shows the plasmid JJ3572.

The plasmid JJ3572 (FIG. 6) has a neophosphotransferase II (nptII) gene (Beck et al. (1982) *Gene* 19:327– 336) fused between a CaMV 35S promoter-cab22L leader and an ocs 3' end (Harpster, M. H., et al. (1988) *Mol. Gen. Genet.* 212: 182–190). The nptII gene, obtained as a BamHI AsuII blunt-ended fragment from pKM109.9 (Reiss, B., et al. (1984) *EMBO J.* 3: 3317–3322), was cloned into NcoI BamHI blunt-ended 2104 (Harpster, M. H., et al. (1988) *Mol. Gen. Genet.* 212: 182–190), replacing the ChiA gene. The resulting plasmid, 2122, has an nptII gene fused between a CaMV 35S promoter and a nos 3' end. In a three-way ligation, the nptII-nos terminator region of 2122 was fused as an NcoI (partial) HindIII fragment to the EcoRI NcoI fragment of p35S(J):Cab22L-CH (Harpster, M. H., et al. (1988) *Mol. Gen. Genet.* 212: 182–190), which contains a CaMV35S promoter and a cab22L leader, and to pMUC (Jones, J. D. G., et al. (1985) *EMBO J.* 4: 2411–2418), opened up in its polylinker region by cutting with HindIII and EcoRI. The resulting clone, 2601, contains the nptII gene fused between the 35S promoter-cab 22L leader and a nos terminator. In the final step, the nos terminator region of 2601 was replaced with the ocs terminator region of 3431 (Svab, Z., et al. (1990) *Plant Mol. Biol.* 14: 197–205) by ligating together the appropriate HindIII XbaI fragments from each plasmid to give JJ3572.

iii. pVicA

The pea vicilin promoter, CW36 (Higgins, T. J. V., et al. (1988) *Plant Mol. Biol.* 11: 683–695) and the pea albumin gene, TJ6, were obtained from T. J. Higgins, CSIRO. The albumin gene was digested with EcoRI and NcoI and fused to a purified 2.8 kb EcoRI-NcoI fragment containing the vicilin promoter to form pVicA (FIG. 7).

B. 35S-driven SH2

In one set of constructs, a CaMV 35S promoter was used to drive expression of sense and antisense versions of SH2.

i. 588 - 1.8 kb SH2 antisense in pWTT2132

SH2 cDNA clone 108-2(B+) was digested with SstI and XbaI, and the 1.8 kb SH2 fragment released was cloned into SstI XbaI-cut JJ3572. This places 1.8 kb of SH2 in antisense orientation between the 35S promoter and the ocs terminator. The resulting clone was 320.

The clone 320 was digested with BglII and SphI, and the 3.6 kb fragment that was released was blunt-ended and ligated into SmaI-cut pWTT2132. The final construct, 588, carries within its T-DNA borders a 35S-driven surB gene and a 35S-driven SH2 antisense gene with an ocs terminator (FIG. 8). In this construct, these two genes lie in inverse orientation with respect to each other.

ii. pGC9-8a - 1.7 kb SH2 sense in pWTT2132

SH2 cDNA clone 108-2-(B+) was digested with EcoRI and the 2 kb insert released was ligated into the EcoRI site of pUCl18 (Vieira, J. et al. (1987) *Methods in Enzymology* 153: 3–11). The resulting clone, 338, was then digested with PstI, which cuts once within the polylinker and once within SH2, and religated. This first step had the effect of removing 1.3 kb of 3' terminal SH2 sequence. Single-stranded DNA was made from this clone (clone 455) in *Escherichia coli* strain BW313, which misincorporates uracil residues into its DNA. Oligo-directed mutagenesis was then performed to create an NcoI site at the translational initiation start site (See, e.g., Zoller, M. J. and Smith, M. (1982) *Nucleic Acids Res.* 10: 6487–6500). The primer AGAAGCCATGGTAG-TAACC was first phosphorylated with T4 polynucleotide kinase and then annealed to single-stranded DNA in 40 μl of annealing buffer (0.1875M KCl; 0.0125M Tris-Cl, pH 7.5) containing 50 pmol of kinased primer and 1 pmol of single-stranded DNA. Annealing was sequentially performed at 55° C. for 30 minutes, at 37° C. for 15 minutes, and at room temperature for 15 minutes. Closed circular DNA was then synthesized by the addition of 4.5 μl of 10 x fill-in buffer (1x=0.0625M KCl; 0.0275M Tris-Cl, pH 7.5; 2 mM DTT; 0.015M $MgCl_2$; 0.2 mM ATP; and 0.1 mM each of dGTP, dATP, dTTP, and dCTP), 5 U of *E.coli* DNA polymerase (Klenow fragment), and 0.3 U of T4 DNA ligase. After an overnight incubation at room temperature, 10 μl of double-stranded DNA was used to transform *Escherichia coli* strain JM83. Construct 472 was selected from the transformants as having an NcoI site at the translational initiation site. Sequencing through this region confirmed that nucleotide 137 of the SH2 sequence had been mutagenized to a C, thereby creating an NcoI site. The 1.3 kb PstI fragment removed in a previous step was next ligated back by cloning the 1.3 kb PstI fragment from 331 into the PstI site of 472, where 331 is the 108-2(-B+) EcoRI insert-ligated into EcoRI-cut pUCl19 (Vieira, J. and Messing, J. (1987), *Methods in Enzymology* 153: 3–11). The resulting plasmid, pGC9-1, was then digested with SstI, which cuts once in the 3' non-translated region and once in the polylinker region. This removed the last 220 bp of the SH2 3' non-translated region, which includes an internal polyadenylation site. The resulting clone, pGC9-2, was partially digested with NcoI, which cuts twice within the SH2 sequence, and fully digested with XbaI, which cuts in the polylinker region. The 1.7 kb NcoI XbaI partial, which includes 20 bp of pUCl19 polylinker sequence (SstI to XbaI), was then ligated into NcoI XbaI-digested JJ3572. This places 1.7 kb of SH2 in sense orientation between the 35S promoter-Cab leader and the ocs terminator. The resulting clone, pGC9-6b, was then cut with SphI and BglII, and the 3.5 kb fragment that was released was blunt-ended and ligated into SmaI-cut pWTT2132. The final construct, pGC9-8a, carries within its T-DNA borders a 35S-driven surB gene and a 35S-driven SH2 sense gene with an ocs terminator (FIG. 9). In this construct these two genes lie in inverse orientation with respect to each other.

C. Vicilin-driven BT2A: pGC9-27.1(antisense)

The seed storage vicilin promoter from pea (obtained from T. J. V. Higgins) (Higgins, T. J. V., et al. (1988) *Plant Mol. Biol.* 11: 683–695) was used to drive expression of antisense BT2A. Vicilin RNA is one of the earliest and most abundant seed storage transcripts made in pea (Higgins, T. J. V. (1984) *Ann. Rev. Plant Physiol.* 35: 191–221). The pea vicilin promoter used has been shown to retain its developmental- and tissue-specificity when fused to an albumin gene and transformed into tobacco.

The antisense construct pGC9-27.1 has the entire BT2A coding region plus part of the 3'non-translated region fused between a 2.5 kb vicilin promoter/5'non-translated region and an albumin 3'non-translated region.

BT2A cDNA clone 104(B−) is missing the 3' end of BT2A. The missing 3' end, which was obtained by PCR amplification (Frohman, M. A., 1990, supra), is present in the clone 106, in which the larger 500 bp amplification product was cloned as an EcoRI BglII fragment into EcoRI BamHI-cut Bluescript(+). The entire BT2A sequence was then generated by cloning a 0.5 kb SstI EcoRI fragment from 106 into 104(B−) that had been partially digested with EcoRI (to cut the 3' site) and fully digested with SstI, which cuts in the polylinker. The resulting clone, 501, was digested with EcoRI and HindIII, and the 1.1 kb EcoRI HindIII fragment was subcloned into EcoRI HindIII-cut pUCl18 (Vieira, J. et al. (1987) *Methods in Enzymology* 153: 3–11). This produced plasmid pGC9-17, which was next altered by oligonucleotide mutagenesis to create an NcoI site at the second translational start site (Zoller, M. J. and Smith, M. (1982) supra). (BT2A has two potential in-frame ATG translational initiation sites separated by 6 bp, with the sequence context surrounding the second ATG being more favorable). The primer CGCAGCCATGGACGCCATA (Seq. I.D. No. 13) was used to mutagenize "A" at position 89 to a "C". Transformant pGC9-17NcoMuta was selected as having an NcoI site at the translational initiation site. Sequencing through the mutagenized region showed that no other alterations took place. The rest of BT2A was then inserted by fusing the 0.95 kb HindIII-fragment from 501 into HindIII-linearized pGC9-17NcoMuta to give pGC9-18.

pGC9-18 was digested with NcoI, blunt-ended, digested with NruI, and the 1.6 kb NcoI NruI fragment that was released was ligated into pVicA that had been cut with NcoI, blunt-ended, and cut with EcoRV. PGC9-24 was selected as having the 1.6 kb BT2A fragment cloned in antisense orientation between the vicilin promoter and the albumin terminator. This translational fusion was then partially digested with EcoRI, blunt-ended, digested with PstI, and the 5.4 kb partial EcoRI-PstI fragment was ligated to SmaI PstI-cut pWTT2132. The final construct, pGC9-27.1, carries within its T-DNA borders a 35S-driven surB gene and a vicilin-driven BT2A antisense gene with an albumin terminator (FIG. 10). In this construct these two genes are transcribed in direct orientation with respect to one another.

IV. Bacterial Transformation

For purposes of constructing plasmids described in the Examples, E. coli bacteria competent for transformation were made by the protocol of R. Hallewell (Chiron Corp.). One ml of an overnight culture was added to 100 mls of pre-warmed LB medium (1% tryptone; 0.5% yeast extract; 0.5% NaCl; 0.1% glucose; pH 7) and the culture was shaken at 37° C. until an OD550 of approximately 0.48 was reached. The culture was then chilled and centrifuged in a refrigerated benchtop centrifuge for ten minutes at 2500 rpm. The bacterial pellet was resuspended in 15 mls of transformation buffer I (30 mM potassium acetate, 50 mMMnCl2, 100 mM RbCl, 10 mM CaCl$_2$, 15% (w/v) glycerol, brought to pH 5.8 with 0.2 M acetic acid) and incubated on ice for 2 hours. The bacteria were then re-pelleted, resuspended in 2 mls of transformation buffer II (10 mM sodium MOPS, infra, pH 7.0:75 mM CaCl$_2$, 10 mM RbCl, 15% glycerol), aliquoted into 100 µl volumes, and stored at −70° C. The E. coli strains used in construction of each plasmid are listed in Table I.

Bacterial transformations were initiated by mixing DNA (in a 1 to 10 µl volume) with 100 µl of competent bacterial cells. Following a 20 minute incubation on ice, the competent cells were heat-shocked at 37° C. for 2 minutes, returned to ice for 1 minute, and diluted with 600 µl of pre-vortexed LB medium. The transformed cells were then incubated for 1 hour at 37° C. before being spread on selective nutrient agar plates.

TABLE 1

| E. coli strains used | |
|---|---|
| 588 | |
| 108$_2$ (B+) | XL1-Blue |
| 320 | DH5αF' |
| 588 | JM83 |
| pGC9-8a | |
| 108$_2$ (B+) | XL1-Blue |
| 338 | DH5αF' |
| 331 | DH5αF' |
| pGC9-1 | XL1-Blue |
| pGC9-2 | JM83 |
| pGC9-6b | JM83 |
| pGC9-8a | JM83 |
| pGC9-27.1 | |
| 104 (B−) | XL1-Blue |
| 106 | DH5αF' |
| 501 | JM83 |
| pGC9-17 | XL1-Blue |
| pGC9-17NcoMuta | JM83 |
| pGC9-18 | JM83 |
| pGC9-24 | JM83 |
| pGC9-27.1 | JM83 |
| pVicA | JM83 |

Note: XL1-Blue is from Stratagene, Inc.; DH5αF' is described in Raleigh et al. (1989), Current Protocols in Molecular Biology (Ausubel et al., Eds.) Publishing Associates and Wiley Interscience, New York, Unit 1.4; JM83 is described, infra.

V. Plant Transformation

Genetically transformed pea plants described in the Examples were produced by Agrobacterium-mediated transformation. Binary T-DNA constructs were mobilized into Agrobacterium tumefaciens strain EHA101/ptiB0542 by triparental mating. EHA101 carries the Ti plasmid ptiB0542 which supplies vir functions in trans. Mobilization functions are supplied by the helper plasmid pRK2013 which is carried by the second parent, E. coli strain HB101 (Ditta et al. (1980) Proc. Natl. Acad. Sci. 77:7347–7351). The third parent, E. coli stain JM83 (Yanish-Perron et al. (1985), Gene 33:103–119), carries the binary vector to be mobilized. A mixture of the three parents was spotted onto LB plates (1% tryptone; 0.5% yeast extract; 0.5% NaCl; 0.1% glucose; 1.5% agar; pH 7), mating was allowed to occur overnight at 28° C., the cells were plated onto LB plates containing 100 µg/ml rifampicin (which selects for Agrobacterium) and 2 µg/ml tetracycline (which selects for the binary vector).

Transformation was according to the protocol presented in Example 9 of U.S. Pat. No. 5,286,635 ("Genetically transformed pea plants and methods for their production"), except that the anti-Agrobacterium antibiotic used in the selection and regeneration medium is cefotaxime (500 mg/l) and shoots were rooted by transfer to Sorbarod plugs (Baumgartnen Papiers SA, Switzerland) soaked in liquid YRM (Table 2).

TABLE 2

| YRM (Chu, C.C., et al., 1975, Scientia Sinica 18: 659–668). | |
|---|---|
| N6 salts and iron: | 1/2 X |
| Thiamine: | 1 mg/l |
| Sucrose: | 30 g/l |
| IAA*: | 2 mg/l |
| pH: | 5.7 |

*Add IAA after autoclaving

The shoots were analyzed by the rooting and recallusing assays on 50 µg/l chlorsulfuron and by PCR using 25 mer oligos designed to detect a 433bp fragment of the introduced SH2 transgene and a 880bp fragment of the endogenous SH2 gene. The sequences of the PCR oligos are as follows:

DEAGP1: 5'-GAGAA TGTAT TGATC TTGGC GGGAG-3' (Seq. I.D. #14)

DEAGP2: 5'-CCAAT ATCTT CCCAG TAGTC TCCGA-3' (Seq. I.D. #15)

VI. Assays for ADPG-PPase Protein and Gene Expression

A. Assays for ADPG-PPase subunit transcript levels

Assays for transcript level referred to in the Examples were carried out as follows:

i. Preparation of Embryo RNA

RNA was prepared from individual embryos as follows. Embryos frozen in liquid nitrogen were ground to a fine powder using a mortar and pestle. The pulverized embryos were then further ground in 0.5 mls NTES (100 mM NaCl, 10 mM Tris-Cl (pH 7.5), 1 mM EDTA, and 1% SDS) and 0.25 mls of buffered phenol. Denatured protein and cell debris were removed by two sequential extractions with SEVAG (24 parts chloroform: 1 part isoamyl alcohol) and RNA was precipitated by the addition of 1 volume of 4M lithium acetate. The RNA pellet was resuspended in 300 µl of 0.3M sodium acetate and re-extracted with SEVAG. The RNA was then precipitated by the addition of 2.5 volumes of ethanol, washed with 70% ethanol, and resuspended in TE (10 mM Tris-Cl (pH 8), 1 mM EDTA).

ii. Northern Hybridization

RNA was separated electrophoretically on a 1.1% agarose gel containing 6% formaldehyde and prepared in a buffer consisting of 20 mMMOPS (3-[N-morpholino]propanesulfonic acid), 5 mM sodium acetate, 1 mM EDTA, pH 8. This buffer was also used as the reservoir buffer except the pH was adjusted to pH 7. RNA (5 µg) was denatured at 55° C. in 65% formamide, 8% formaldehyde, 26 mM MOPS, 6.5 mM sodium acetate, 1.3 mM EDTA, pH 8 before being loaded on to the formaldehyde gel. Following electrophoresis at 4 V/cm, the RNA was transferred to a Duralon-UV membrane (Stratagene) and UV-cross-linked with a Stratagene Stratalinker. Uniform RNA loading and transfer were verified by UV shadowing.

For detection of SH2 RNA transcripts, Northern blots were hybridized with a 223 nt EcoRI-HindIII fragment (5'non-translated region plus transit sequence) labeled either by Klenow using random primers (Feinberg, A. P. et al. (1983) *Anal. Biochem.* 132: 6–13) or as a riboprobe using T3 RNA polymerase. BT2A RNA transcripts were detected using a 385 nt EcoRI-HincII riboprobe (from the 5' end of BT2A) radiolabeled with T3 RNA polymerase. Hybridizations were performed in 0.25M phosphate buffer (pH 7.4), 7% SDS, 1 mM EDTA, 1% bovine serum albumin at 65° C. (for random-primer labeled probes) or 70° C. (for riboprobes) in a Robbins hybridization incubator. Final washes were performed in 0.1xSSC at 65° C. (for random-primer labeled probes) or 75° C. (for riboprobes).

iii. Ribonuclease Protections

The same SH2 and BT2A riboprobes described above under "Northern hybridization" were also used in ribonuclease protection assays. RNA dissolved in 80% formamide, 40 mM PIPES (piperazine-N,N'-bis[2-ethanesulfonic acid]) (pH 6.7), 0.4M NaCl, 1 mM EDTA was mixed with one million cpm of radiolabeled probe, incubated for 5 min at 85° C. and then allowed to anneal at 45° C. overnight Unhybridized riboprobe sequences were removed by a 1 hour digestion at 30° C. with 12 µg of RNase A and 0.6 µg of RNase T1 in 300 µl of RNase digestion buffer (10 mM Tris-Cl (pH 7.5), 5 mM EDTA, 0.3M NaCl). Reactions were terminated by a 20 min incubation at 37° C. in the presence of 20 µl of 10% SDS and 50 µg of proteinase K. Samples were deproteinized by a phenol/SEVAG extraction and undigested RNA was recovered by ethanol precipitation in the presence of 15 µg of carrier tRNA. RNA pellets were resuspended in 6 µl of loading buffer (90% formamide, 0.3% xylene cyanol, 0.3% bromphenol blue), denatured at 85° C. for 5 min, and immediately loaded on to a 6% polyacrylamide/urea gel.

B. Assays for Sugar and Starch

Assays for sugar or starch referred to in the Examples below were carried out as follows. From a single sample it is possible to assay for both sugars and starch. The sample is dried to a stable weight in a Savant Speed-Vac Concentrator and then pulverized to a powder using a mortar and pestle. A pre-weighed amount of sample (5–50 mg) is washed several times in 80% ethanol at 70° C. The ethanol supernatants are pooled and used for sugar determinations. The pellet is used for starch determination.

i. Starch Assays

The pellet is brought up in 2 mls of water and autoclaved for 45 minutes. The gelatinized starch is first digested with α-amylase (30 U from porcine pancreas in 140 µl of 0.3M sodium acetate) for 30 minutes at 37° C. and then with amyloglucosidase (20 U from *Aspergillus niger* in 960 µl of 0.1M sodium acetate, pH 4.6) at 55° C. for 1 hour. The sample is deproteinized by boiling and the cleared supernatant is assayed for glucose using a dehydrogenase-coupled spectrophotometric assay (Jones, MGK, et al. (1977) *Plant Physiol.* 60: 379–383). Glucose levels are enzymatically linked in this assay to the reduction of NAD+, which can be monitored spectrophotometrically.

An aliquot of the hydrolyzed starch is incubated at room temperature in 0.1M Tris-Cl (pH 8), 1 mM ATP, 1 mM NAD+, 2 mM MgCl$_2$, 15 U/ml yeast hexokinase, and 15 U/ml *Leuconostoc mesenteroides* glucose-6-phosphate dehydrogenase. The reaction is allowed to go to completion and the absorbance is read at 340 nm and compared with a standard curve.

ii. Sucrose Assays

The pooled 80% ethanol supernatants are brought to 3 mls with 80% ethanol. Following the addition of 1.625 ml of water and 0.75 ml of chloroform, the sample is vortexed and spun in a table top centrifuge. The top phase is removed, evaporated to dryness on a Savant Speed-Vac Concentrator, and resuspended in 150 µl of water.

Glucose and fructose are first destroyed by incubating the sample in 0.02N NaOH for 30 min at 95° C. The sample is then neutralized by addition of one-fortieth volume of 1M sodium acetate, pH 4.6. Sucrose levels are then determined using a dehydrogenase-coupled spectrophotometric assay similar to the one described above, except that invertase is included to hydrolyze the sucrose to glucose plus fructose, and the pH is lowered to suit the more acidic requirements of invertase.

An aliquot of the alkali-treated sample is incubated at room temperature in 40 mM imidazole (pH 6.9), 1 mM ATP, 1 mM NAD+, 5 mM MgCl$_2$, 0.5 mM DTT, 0.02% BSA, 32 U/ml yeast invertase, 5 U/ml yeast hexokinase, and 5 U/ml *Leuconostoc mesenteroides* glucose-6-phosphate dehydrogenase. The reaction is allowed to go to completion and the absorbance is read at 340 nm and compared with a standard curve.

VII. Demonstration of Antisense Suppression

A. DB04-10B (35S-SH2 antisense suppressant)

Sugar Daddy pea was transformed with construct 588 (35S-ALS/35S-SH2, antisense). Sugar Daddy peas used here and elsewhere in the Examples were grown from seed obtained from W. Atlee Burpee & Co., 300 Park Avenue, Warminster, Pa. 18974. Twenty-three of the transformants were analyzed with Northerns for suppression of endogenous SH2 transcript. DB04-10B was identified as having suppressed levels of SH2 transcripts. This transformant was confirmed to have been transformed by PCR analysis, by recallusing on chlorsulfuron, and by Southern analysis.

The RNA analysis was done as follows. RNA was made from eight individual embryos (Ib; IId, e, f, g, h; III i, j) from three different pods. SH2 transcript levels were analyzed either on Northerns or using a ribonuclease protection assay. Six of the eight embryos showed suppressed levels of SH2 transcript (about 5–10% of normal); two had normal levels of SH2 RNA. Two other embryos (Ia and IIc) were not analyzed. See Table 3. As used here and elsewhere below in the Examples, normal or percent of normal is with reference to control plants. Control plants used in these Examples are either non-transformed plants or plants which have gone through the same transformation process without actually being transformed (i.e., escapes), as shown by negative results in both PCR assay and chlorsulfuron recallusing assay.

No significant difference in embryo size could be discerned between the suppressed embryos and the non-suppressed embryos. The 3:1 ratio observed for suppressed to non-suppressed embryos fits the Mendelian ratio expected for a single dominant trait segregating out of a self-cross.

An iodine starch stain assay was performed on seeds from DB04-10B and on seeds from control plants. Seeds from DB04-10B stained less intensely than seeds from the control plants, indicating that DB04-10B seeds accumulated less starch.

Out of six seeds planted from a self-cross of DB04-10B, three grew to plants (DB04-10BX1, X2, X4). Embryos of these three progeny plants were analyzed on Northerns to determine whether the suppression of SH2 RNA transcript levels was inherited. Two of the progeny plants (DB04-10BX1 and DB04-10BX4) showed no suppression (analysis was done on five embryos of DB04-10BX1 and seven embryos of DB04-10BX4). The third progeny plant (DB04-10BX2) showed suppression in sixteen of sixteen embryos analyzed, indicating inheritance with homozygosity for the introduced gene in this progeny plant. All sixteen of the embryos showed transcript levels less than 5% of normal (i.e., over 95% suppression). No obvious differences were seen between these three progeny plants in terms of their growth habits, node at which flowering initiates, seed set, seed size, or overall vigor.

Sucrose and starch levels were compared between embryos from two of the progeny plants: DB04-10BX2, the suppressed progeny plant, and DB04-10BX4, a non-suppressed progeny plant. Starch levels (% of dry weight) were lower in embryos from the suppressed pod than in embryos from the non-suppressed pod (8.0% vs 12.3%) and sucrose levels (% of dry weight) were higher in embryos from the suppressed pod than in embryos from the non-suppressed pod (32.0% vs 28.8%). The reduction in starch and increase in sucrose is consistent with the effects expected from an antisense-mediated suppression of ADP-glucose pyrophosphorylase.

TABLE 3

|  | Pod | Embryo | % Normal SH2 Transcript Level |
|---|---|---|---|
| DB04-10B | I | b | 10% |
|  | II | d | 10% |
|  |  | e | 100% |
|  |  | f | 10% |
|  |  | g | 10% |
|  |  | h | 10% |
|  | III | i | 100% |
|  |  | j | 5% |

B. DF35-17B, DF31-43B, DF31-72A, DF31-47(pVic-BT2A antisense suppressants)

Sugar Daddy pea was transformed with construct pGC9-27.1 (35S-ALS/pVic-BT2A, antisense). Fourteen of the transformants were analyzed with Northerns for suppression of endogenous BT2 transcript. Transformants DF35-17B, DF31-43B, DF31-72A and DF31-47A were identified as having suppressed levels of BT2 transcripts. They were confirmed as transformed by ability to recallus on chlorsulfuron.

For RNA analyses, RNA from the embryos was separated electrophoretically and transferred to a nylon filter. The filter was hybridized with a radioactively labeled BT2A cDNA riboprobe. The results were as follows:

i. DF31-17B: RNA was made from six embryos from two different pods. Normal levels of BT2A RNA were detected in the three embryos harvested from the first pod. However, all three embryos from the second pod showed 90% reduction in levels of BT2A RNA (i.e., 10% of normal). See Table 4.

ii. DF31-43B: Two pods were examined. From the first pod three embryos were analyzed; no suppression was seen. From the second pod three of the four embryos showed a 50% reduction in BT2A RNA and the fourth showed a 20% reduction. See Table 4.

iii. DF31-72A: Two pods were examined. From the first pod three of three embryos showed a 50% reduction in BT2A RNA. From the second pod two of three embryos showed a 50% reduction in BT2A RNA. See Table 4.

iv. DF31-47A: Two pods were examined. From the first pod four embryos were analyzed; none showed suppression. From the second pod three of four embryos showed 80%–90% reduction in BT2A RNA; the fourth showed no reduction. See Table 4.

TABLE 4

|  | Pod | Embryo | % Normal BT2A Transcript Level |
|---|---|---|---|
| DF35-17B | I | a | 100% |
|  |  | b | 100% |
|  |  | c | 100% |
|  | II | d | 10% |
|  |  | e | 10% |
|  |  | f | 10% |
| DF31-43B | I | a | 100% |
|  |  | b | 100% |
|  |  | c | 100% |
|  | II | d | 50% |
|  |  | e | 80% |
|  |  | f | 50% |
|  |  | g | 50% |
| DF31-72A | I | a | 50% |
|  |  | b | 50% |
|  |  | c | 50% |
|  | II | d | 100% |
|  |  | e | 50% |
|  |  | f | 50% |
| DF31-47A | I | a | 100% |
|  |  | b | 100% |
|  |  | c | 100% |
|  |  | d | 100% |
|  | II | e | 10% |
|  |  | f | 10% |
|  |  | g | 100% |
|  |  | h | 20% |

VIII. Demonstration of Sense Suppression

Embryos from 59 sense transformants were analyzed with Northerns for suppression of endogenous SH2 expression. Sense transformant DA12-002A was identified as having suppressed levels of SH2 transcript.

Sugar Daddy pea was transformed with construct pGC9-8a (35S-ALS/35S-SH2, sense) to give transformant DA12-002A. The transformant was confirmed to be transformed by PCR analysis and by recallusing on chlorosulfuron. Expression of the 35S-ALS transgene, which encodes chlorsulfuron resistance, was detected in leaves via ribonuclease protection.

RNA of DA12-002A was examined from a total of seven embryos from two pods. SH2 transcript levels in all the embryos were analyzed by both Northern and ribonuclease protection assays. Transcript was not detectable in the suppressants using Northern analysis. With ribonuclease protection assays, of the seven embryos, three showed levels of SH2 transcript suppressed to about 2.5–7.5% of normal; one showed a level suppressed to 40% of normal. No significant difference in embryo size was discerned between the suppressed embryos and the non-suppressed embryos. See Table 5.

TABLE 5

|  | POD | Embryo | % Normal SH2 Transcript Level |
|---|---|---|---|
| DA12-002A | I | a | 100% |
|  |  | b | 100% |
|  | II | c | 2.5% |
|  |  | d | 100% |
|  |  | e | 5% |
|  |  | f | 40% |
|  |  | g | 7.5% |

All publications and other references or patent documents herein are incorporated by reference. It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed:

1. An isolated polynucleotide having the sequence of Seq. I.D. No. 1, Seq. I.D. No. 3, Seq. I.D. No. 5, Seq. I.D. No. 7, Seq. I.D. No. 8, or Seq. I.D. No. 9.

2. The polynucleotide of claim 1, wherein the polynucleotide is operably linked to a promoter.

3. The polynucleotide of claim 2, wherein the promoter is a heterologous promoter.

4. The polynucleotide of claim 2, wherein the polynucleotide is transcribed in the sense orientation.

5. The polynucleotide of claim 4 wherein, the polynucleotide is full-length.

6. A plant of genus Pisum comprising the polynucleotide of claim 2, wherein said polynucleotide is less than full-length.

7. The plant of claim 6, wherein the polynucleotide is transcribed in at least one cell of the plant.

8. Seeds, fruit, and roots of the plant of claim 6.

9. A pea plant comprising the polynucleotide of claim 3.

10. The pea plant of claim 9, wherein ADPG-PPase expression is suppressed compared to a wild-type pea plant.

11. The pea plant of claim 9, wherein the sucrose content of at least one plant part is increased compared to the corresponding plant part of a wild-type pea plant.

12. Edible peas of the plant of claim 9.

13. A method for producing a plant of genus Pisum having increased sucrose content in at least one part of the plant, comprising the steps:

transforming plant cells of genus Pisum with the polynucleotide of claim 1 using Agrobacterium, wherein transformed plant cells are produced;

growing plants from the transformed plant cells, wherein transformed plants are produced; and, selecting a transformed plant having increased sucrose content in at least one plant part, when compared to similar untransformed plants.

14. The method of claim 13, wherein the plant is pea.

15. The method of claim 14, wherein the plant is garden pea.

16. The method of claim 13, wherein the plant is selected by screening for ADPG-PPase activity or for ADPG-PPase subunit mRNA levels.

17. The method of claim 13, wherein the plant is selected by screening for decreased starch levels in a plant part.

18. The method of claim 13, wherein the polynucleotide comprises a sequence of an SH2 subunit gene.

19. The method of claim 13, wherein the polynucleotide comprises a sequence of a BT2 subunit gene.

20. The method of claim 13, wherein the polynucleotide is transcribed to produce a sense transcript, whereby levels of mRNA encoding at least one ADPG-PPase subunit are reduced.

21. The method of claim 13, wherein the polynucleotide is transcribed to produce an antisense transcript, whereby the level of mRNA encoding at least one ADPG-PPase subunit is suppressed.

22. The polynucleotide of claim 4 wherein the promoter is heterologous.

23. The plant of claim 6, wherein the plant is of species *Pisum sarivum*.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 2032 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 137..1666

( x i ) SEQUENCE DESCRIPTION: SEQ ID NO:1:

```
GTCACATTCT  TCTCTTTGTT  TCTCTAGATT  CTATATTTTA  GTTGTGACCT  TTCACTACTA         60

GCATTGTTTC  TCTCTTATTC  TCTTGGTCTG  AGTTTGAACA  AACTCAAAAA  AAGCTTAGTT        120

TTTTGAGGTT  ACTACA ATG GCT TCT GGT TGT GTG AGC TTG AAA ACC AAC               169
              Met Ala Ser Gly Cys Val Ser Leu Lys Thr Asn
                1               5                   10

ACC CAT TTT CCA AAT TCT AAA AAA GGT TCT TTT TTT GGG GAA AGA ATC              217
Thr His Phe Pro Asn Ser Lys Lys Gly Ser Phe Phe Gly Glu Arg Ile
            15                  20                  25

AAA GGA AGC TTG AAA AAC AGT TCA TGG GTC ACT ACC CAG AAG AAG ATC              265
Lys Gly Ser Leu Lys Asn Ser Ser Trp Val Thr Thr Gln Lys Lys Ile
        30                  35                  40

AAA CCT GCT TCT TTT TCT GCT ATT CTT ACT TCA GAT GAC CCC AAA GGT              313
Lys Pro Ala Ser Phe Ser Ala Ile Leu Thr Ser Asp Asp Pro Lys Gly
    45                  50                  55

TCC CTG AAT TTG CAA GTG CCT TCA TTT CTG AGA CTA AGA GCT GAT CCA              361
Ser Leu Asn Leu Gln Val Pro Ser Phe Leu Arg Leu Arg Ala Asp Pro
60                  65                      70                  75

AAA AAT GTG ATT TCC ATT GTG TTG GGA GGA GGG CCT GGA ACA CAT CTC              409
Lys Asn Val Ile Ser Ile Val Leu Gly Gly Gly Pro Gly Thr His Leu
```

|  |  |  |  |  |  |  |  |  |  |  |  |  |  |  |  |  |
|---|---|---|---|---|---|---|---|---|---|---|---|---|---|---|---|---|
|  |  |  |  | 80 |  |  |  |  | 85 |  |  |  |  | 90 |  |  |
| TAT | CCT | CTT | ACC | AAA | CGA | GCT | GCA | ACA | CCT | GCG | GTT | CCT | GTT | GGA | GGA | 457 |
| Tyr | Pro | Leu | Thr | Lys | Arg | Ala | Ala | Thr | Pro | Ala | Val | Pro | Val | Gly | Gly |  |
|  |  |  | 95 |  |  |  |  | 100 |  |  |  |  | 105 |  |  |  |
| TGC | TAT | AGG | CTT | ATA | GAC | ATT | CCA | ATG | AGC | AAC | TGC | ATC | AAT | AGT | GGC | 505 |
| Cys | Tyr | Arg | Leu | Ile | Asp | Ile | Pro | Met | Ser | Asn | Cys | Ile | Asn | Ser | Gly |  |
|  |  | 110 |  |  |  | 115 |  |  |  |  | 120 |  |  |  |  |  |
| ATC | AAC | AAG | ATA | TTT | GTG | CTG | ACT | CAG | TTC | AAC | TCT | GCT | TCA | CTA | AAT | 553 |
| Ile | Asn | Lys | Ile | Phe | Val | Leu | Thr | Gln | Phe | Asn | Ser | Ala | Ser | Leu | Asn |  |
|  | 125 |  |  |  |  | 130 |  |  |  |  | 135 |  |  |  |  |  |
| CGT | CAC | ATC | GCT | CGC | ACC | TAT | TTC | GGA | AAT | GGT | GTC | AAC | TTT | GGA | GAT | 601 |
| Arg | His | Ile | Ala | Arg | Thr | Tyr | Phe | Gly | Asn | Gly | Val | Asn | Phe | Gly | Asp |  |
| 140 |  |  |  |  | 145 |  |  |  |  | 150 |  |  |  |  | 155 |  |
| GGA | TTT | GTG | GAG | GTT | CTG | GCG | GCG | ACT | CAA | ACA | CCA | GGA | GAA | GCT | GGG | 649 |
| Gly | Phe | Val | Glu | Val | Leu | Ala | Ala | Thr | Gln | Thr | Pro | Gly | Glu | Ala | Gly |  |
|  |  |  |  | 160 |  |  |  |  | 165 |  |  |  |  | 170 |  |  |
| AAG | AAG | TGG | TTT | CAA | GGA | ACT | GCA | GAT | GCT | GTG | AGA | CAA | TTT | ACC | TGG | 697 |
| Lys | Lys | Trp | Phe | Gln | Gly | Thr | Ala | Asp | Ala | Val | Arg | Gln | Phe | Thr | Trp |  |
|  |  |  | 175 |  |  |  |  | 180 |  |  |  |  | 185 |  |  |  |
| ATA | TTT | GAG | GAT | GCC | AAG | AAT | ATA | AAC | GTC | GAG | AAT | GTA | TTG | ATC | TTG | 745 |
| Ile | Phe | Glu | Asp | Ala | Lys | Asn | Ile | Asn | Val | Glu | Asn | Val | Leu | Ile | Leu |  |
|  |  | 190 |  |  |  | 195 |  |  |  |  | 200 |  |  |  |  |  |
| GCG | GGA | GAT | CAT | TTA | TAT | CGA | ATG | GAT | TAC | ATG | GAC | CTA | TTG | CAG | AGT | 793 |
| Ala | Gly | Asp | His | Leu | Tyr | Arg | Met | Asp | Tyr | Met | Asp | Leu | Leu | Gln | Ser |  |
|  | 205 |  |  |  |  | 210 |  |  |  |  | 215 |  |  |  |  |  |
| CAC | GTT | GAT | AGA | AAT | GCC | GAT | ATT | ACA | GTT | TCG | TGT | GCT | GCC | GTT | GGT | 841 |
| His | Val | Asp | Arg | Asn | Ala | Asp | Ile | Thr | Val | Ser | Cys | Ala | Ala | Val | Gly |  |
| 220 |  |  |  |  | 225 |  |  |  |  | 230 |  |  |  |  | 235 |  |
| GAC | AAC | CGC | GCA | TCT | GAT | TAT | GGA | TTG | GTC | AAG | GTA | GAC | GAC | AGA | GGC | 889 |
| Asp | Asn | Arg | Ala | Ser | Asp | Tyr | Gly | Leu | Val | Lys | Val | Asp | Asp | Arg | Gly |  |
|  |  |  |  | 240 |  |  |  |  | 245 |  |  |  |  | 250 |  |  |
| AAC | ATC | ATA | CAA | TTT | TCA | GAA | AAA | CCG | AAA | GGC | GCT | GAT | CTG | AAA | GCA | 937 |
| Asn | Ile | Ile | Gln | Phe | Ser | Glu | Lys | Pro | Lys | Gly | Ala | Asp | Leu | Lys | Ala |  |
|  |  |  | 255 |  |  |  |  | 260 |  |  |  |  | 265 |  |  |  |
| ATG | CAA | GTA | GAT | ACT | TCT | CGT | CTT | GGG | TTG | TCG | CCA | CAA | GAT | GCA | TTG | 985 |
| Met | Gln | Val | Asp | Thr | Ser | Arg | Leu | Gly | Leu | Ser | Pro | Gln | Asp | Ala | Leu |  |
|  |  | 270 |  |  |  |  | 275 |  |  |  |  | 280 |  |  |  |  |
| AAG | TCG | CCA | TAT | ATT | GCA | TCT | ATG | GGA | GTT | TAT | GTG | TTC | AAG | AAA | GAT | 1033 |
| Lys | Ser | Pro | Tyr | Ile | Ala | Ser | Met | Gly | Val | Tyr | Val | Phe | Lys | Lys | Asp |  |
|  | 285 |  |  |  |  | 290 |  |  |  |  | 295 |  |  |  |  |  |
| GTT | TTA | CTC | AAG | CTT | CTG | AAA | TGG | AGG | TAT | CCT | ACT | TCT | AAT | GAC | TTC | 1081 |
| Val | Leu | Leu | Lys | Leu | Leu | Lys | Trp | Arg | Tyr | Pro | Thr | Ser | Asn | Asp | Phe |  |
| 300 |  |  |  |  | 305 |  |  |  |  | 310 |  |  |  |  | 315 |  |
| GGA | TCC | GAA | ATC | ATT | CCT | TCC | GCT | ATA | AGA | GAA | CAC | AAT | GTC | CAA | GCA | 1129 |
| Gly | Ser | Glu | Ile | Ile | Pro | Ser | Ala | Ile | Arg | Glu | His | Asn | Val | Gln | Ala |  |
|  |  |  |  | 320 |  |  |  |  | 325 |  |  |  |  | 330 |  |  |
| TAC | TTT | TTC | GGA | GAC | TAC | TGG | GAA | GAT | ATT | GGA | ACG | ATA | AAA | TCC | TTC | 1177 |
| Tyr | Phe | Phe | Gly | Asp | Tyr | Trp | Glu | Asp | Ile | Gly | Thr | Ile | Lys | Ser | Phe |  |
|  |  |  | 335 |  |  |  |  | 340 |  |  |  |  | 345 |  |  |  |
| TAC | GAT | GCT | AAC | CTC | GCT | CTT | ACT | GAA | GAG | AGT | CCA | AAG | TTC | GAG | TTT | 1225 |
| Tyr | Asp | Ala | Asn | Leu | Ala | Leu | Thr | Glu | Glu | Ser | Pro | Lys | Phe | Glu | Phe |  |
|  |  | 350 |  |  |  | 355 |  |  |  |  | 360 |  |  |  |  |  |
| TAT | GAT | CCA | AAA | ACA | CCG | ATT | TTC | ACA | TCT | CCT | GGA | TTC | CTA | CCA | CCA | 1273 |
| Tyr | Asp | Pro | Lys | Thr | Pro | Ile | Phe | Thr | Ser | Pro | Gly | Phe | Leu | Pro | Pro |  |
| 365 |  |  |  |  |  | 370 |  |  |  |  | 375 |  |  |  |  |  |
| ACA | AAG | ATT | GAC | AAC | TCT | CGG | GTT | GTG | GAT | GCC | ATT | ATC | TCC | CAT | GGA | 1321 |
| Thr | Lys | Ile | Asp | Asn | Ser | Arg | Val | Val | Asp | Ala | Ile | Ile | Ser | His | Gly |  |
| 380 |  |  |  |  | 385 |  |  |  |  | 390 |  |  |  |  | 395 |  |
| TGT | TTC | CTG | AGA | GAT | TGT | ACA | ATC | CAA | CAC | TCC | ATT | GTA | GGT | GAA | AGG | 1369 |
| Cys | Phe | Leu | Arg | Asp | Cys | Thr | Ile | Gln | His | Ser | Ile | Val | Gly | Glu | Arg |  |

|   |   |   |   |   |   |   |   |   |   |   |   |   |   |   |   |
|---|---|---|---|---|---|---|---|---|---|---|---|---|---|---|---|
| TCG | CGT | TTA | GAT | TAT | GGC | GTT | GAG | CTT | CAG | GAC | ACT | GTA | ATG | ATG | GGA | 1417 |
| Ser | Arg | Leu | Asp | Tyr | Gly | Val | Glu | Leu | Gln | Asp | Thr | Val | Met | Met | Gly |
|   |   |   | 415 |   |   |   |   | 420 |   |   |   |   | 425 |   |   |
| GCT | GAC | TAT | TAC | CAA | ACT | GAA | TCC | GAA | ATC | GCT | TCC | CTA | CTT | GCA | GAA | 1465 |
| Ala | Asp | Tyr | Tyr | Gln | Thr | Glu | Ser | Glu | Ile | Ala | Ser | Leu | Leu | Ala | Glu |
|   |   | 430 |   |   |   |   | 435 |   |   |   |   | 440 |   |   |   |
| GGG | AAG | GTC | CCG | ATT | GGC | ATC | GGA | AGG | AAT | ACC | AAA | ATC | AAG | AAC | TGC | 1513 |
| Gly | Lys | Val | Pro | Ile | Gly | Ile | Gly | Arg | Asn | Thr | Lys | Ile | Lys | Asn | Cys |
|   | 445 |   |   |   |   | 450 |   |   |   |   | 455 |   |   |   |   |
| ATT | ATT | GAC | AAG | AAT | GCA | AAA | ATC | GGG | AAA | GAA | GTT | GTC | ATC | GCG | AAC | 1561 |
| Ile | Ile | Asp | Lys | Asn | Ala | Lys | Ile | Gly | Lys | Glu | Val | Val | Ile | Ala | Asn |
| 460 |   |   |   |   | 465 |   |   |   |   | 470 |   |   |   |   | 475 |
| AAA | GAA | GGC | GTT | CAA | GAA | GCA | GAT | AGA | TCG | GAA | GAT | GGT | TTC | TAC | ATC | 1609 |
| Lys | Glu | Gly | Val | Gln | Glu | Ala | Asp | Arg | Ser | Glu | Asp | Gly | Phe | Tyr | Ile |
|   |   |   |   | 480 |   |   |   |   | 485 |   |   |   |   | 490 |   |
| CGA | TCA | GGA | ATC | ACC | ATC | ATA | ATG | GAG | AAA | GCA | ACG | ATA | GAA | GAC | GGA | 1657 |
| Arg | Ser | Gly | Ile | Thr | Ile | Ile | Met | Glu | Lys | Ala | Thr | Ile | Glu | Asp | Gly |
|   |   |   | 495 |   |   |   |   | 500 |   |   |   |   | 505 |   |   |
| ACT | GTC | ATA | TAAACAATGG | TTAGTAGTTA | TTTCACGAGC | TGGTTTCCGT | A | 1707 |
| Thr | Val | Ile |
|   |   | 510 |

```
AAGCGCCGGA AGAAGCATTG CAAGGAACAC TCCCTCCCAT CTTTTGGGAT TGGTACAAAA    1767

TGTTATGTTG AATAGAGAAA GCTGCATGTG TAAAATAGGA GAGCTCTTTC ACTAGATGTA    1827

GAAATAGAAA TGAATAAATG ATGAAAGTGA AGATGCAGAA AAGTTAAATA AATGGAAGGG    1887

TTGAGTGTGT GAAGGTATCA AGTTTCTATA TCCTCTCCCT TGAAACTGCA AAGGACATGT    1947

TTTAAATTAT TGTATCACTT AATTATTGTT TTGAATGGTG GTAATAAGCA TTATAATCAC    2007

TTATTTGCTT CAAAAAAAAA AAAAA                                         2032
```

( 2 ) INFORMATION FOR SEQ ID NO:2:

( i ) SEQUENCE CHARACTERISTICS:
        ( A ) LENGTH: 510 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|   |   |   |   |   |   |   |   |   |   |   |   |   |   |   |
|---|---|---|---|---|---|---|---|---|---|---|---|---|---|---|
| Met | Ala | Ser | Gly | Cys | Val | Ser | Leu | Lys | Thr | Asn | Thr | His | Phe | Pro | Asn |
| 1 |   |   |   | 5 |   |   |   |   | 10 |   |   |   |   | 15 |
| Ser | Lys | Lys | Gly | Ser | Phe | Phe | Gly | Glu | Arg | Ile | Lys | Gly | Ser | Leu | Lys |
|   |   |   | 20 |   |   |   |   | 25 |   |   |   |   | 30 |   |
| Asn | Ser | Ser | Trp | Val | Thr | Thr | Gln | Lys | Lys | Ile | Lys | Pro | Ala | Ser | Phe |
|   |   | 35 |   |   |   |   | 40 |   |   |   |   | 45 |   |   |
| Ser | Ala | Ile | Leu | Thr | Ser | Asp | Asp | Pro | Lys | Gly | Ser | Leu | Asn | Leu | Gln |
|   | 50 |   |   |   |   | 55 |   |   |   |   | 60 |   |   |   |
| Val | Pro | Ser | Phe | Leu | Arg | Leu | Arg | Ala | Asp | Pro | Lys | Asn | Val | Ile | Ser |
| 65 |   |   |   |   | 70 |   |   |   |   | 75 |   |   |   |   | 80 |
| Ile | Val | Leu | Gly | Gly | Gly | Pro | Gly | Thr | His | Leu | Tyr | Pro | Leu | Thr | Lys |
|   |   |   |   | 85 |   |   |   |   | 90 |   |   |   |   | 95 |   |
| Arg | Ala | Ala | Thr | Pro | Ala | Val | Pro | Val | Gly | Gly | Cys | Tyr | Arg | Leu | Ile |
|   |   |   | 100 |   |   |   |   | 105 |   |   |   |   | 110 |   |
| Asp | Ile | Pro | Met | Ser | Asn | Cys | Ile | Asn | Ser | Gly | Ile | Asn | Lys | Ile | Phe |
|   |   | 115 |   |   |   |   | 120 |   |   |   |   | 125 |   |   |
| Val | Leu | Thr | Gln | Phe | Asn | Ser | Ala | Ser | Leu | Asn | Arg | His | Ile | Ala | Arg |
|   | 130 |   |   |   |   | 135 |   |   |   |   | 140 |   |   |   |

| | | | | | | | | | | | | | | |
|---|---|---|---|---|---|---|---|---|---|---|---|---|---|---|
| Thr | Tyr | Phe | Gly | Asn | Gly | Val | Asn | Phe | Gly | Asp | Gly | Phe | Val | Glu | Val |
| 145 | | | | 150 | | | | | 155 | | | | | 160 | |
| Leu | Ala | Ala | Thr | Gln | Thr | Pro | Gly | Glu | Ala | Gly | Lys | Lys | Trp | Phe | Gln |
| | | | | 165 | | | | | 170 | | | | | 175 | |
| Gly | Thr | Ala | Asp | Ala | Val | Arg | Gln | Phe | Thr | Trp | Ile | Phe | Glu | Asp | Ala |
| | | | 180 | | | | | 185 | | | | | 190 | | |
| Lys | Asn | Ile | Asn | Val | Glu | Asn | Val | Leu | Ile | Leu | Ala | Gly | Asp | His | Leu |
| | | 195 | | | | | 200 | | | | | 205 | | | |
| Tyr | Arg | Met | Asp | Tyr | Met | Asp | Leu | Leu | Gln | Ser | His | Val | Asp | Arg | Asn |
| | 210 | | | | | 215 | | | | | 220 | | | | |
| Ala | Asp | Ile | Thr | Val | Ser | Cys | Ala | Ala | Val | Gly | Asp | Asn | Arg | Ala | Ser |
| 225 | | | | | 230 | | | | | 235 | | | | | 240 |
| Asp | Tyr | Gly | Leu | Val | Lys | Val | Asp | Asp | Arg | Gly | Asn | Ile | Ile | Gln | Phe |
| | | | | 245 | | | | | 250 | | | | | 255 | |
| Ser | Glu | Lys | Pro | Lys | Gly | Ala | Asp | Leu | Lys | Ala | Met | Gln | Val | Asp | Thr |
| | | | 260 | | | | | 265 | | | | | 270 | | |
| Ser | Arg | Leu | Gly | Leu | Ser | Pro | Gln | Asp | Ala | Leu | Lys | Ser | Pro | Tyr | Ile |
| | | 275 | | | | | 280 | | | | | 285 | | | |
| Ala | Ser | Met | Gly | Val | Tyr | Val | Phe | Lys | Lys | Asp | Val | Leu | Leu | Lys | Leu |
| | 290 | | | | | 295 | | | | | 300 | | | | |
| Leu | Lys | Trp | Arg | Tyr | Pro | Thr | Ser | Asn | Asp | Phe | Gly | Ser | Glu | Ile | Ile |
| 305 | | | | | 310 | | | | | 315 | | | | | 320 |
| Pro | Ser | Ala | Ile | Arg | Glu | His | Asn | Val | Gln | Ala | Tyr | Phe | Phe | Gly | Asp |
| | | | | 325 | | | | | 330 | | | | | 335 | |
| Tyr | Trp | Glu | Asp | Ile | Gly | Thr | Ile | Lys | Ser | Phe | Tyr | Asp | Ala | Asn | Leu |
| | | | 340 | | | | | 345 | | | | | 350 | | |
| Ala | Leu | Thr | Glu | Glu | Ser | Pro | Lys | Phe | Glu | Phe | Tyr | Asp | Pro | Lys | Thr |
| | | 355 | | | | | 360 | | | | | 365 | | | |
| Pro | Ile | Phe | Thr | Ser | Pro | Gly | Phe | Leu | Pro | Pro | Thr | Lys | Ile | Asp | Asn |
| | 370 | | | | | 375 | | | | | 380 | | | | |
| Ser | Arg | Val | Val | Asp | Ala | Ile | Ile | Ser | His | Gly | Cys | Phe | Leu | Arg | Asp |
| 385 | | | | | 390 | | | | | 395 | | | | | 400 |
| Cys | Thr | Ile | Gln | His | Ser | Ile | Val | Gly | Glu | Arg | Ser | Arg | Leu | Asp | Tyr |
| | | | | 405 | | | | | 410 | | | | | 415 | |
| Gly | Val | Glu | Leu | Gln | Asp | Thr | Val | Met | Met | Gly | Ala | Asp | Tyr | Tyr | Gln |
| | | | 420 | | | | | 425 | | | | | 430 | | |
| Thr | Glu | Ser | Glu | Ile | Ala | Ser | Leu | Leu | Ala | Glu | Gly | Lys | Val | Pro | Ile |
| | | 435 | | | | | 440 | | | | | 445 | | | |
| Gly | Ile | Gly | Arg | Asn | Thr | Lys | Ile | Lys | Asn | Cys | Ile | Ile | Asp | Lys | Asn |
| | 450 | | | | | 455 | | | | | 460 | | | | |
| Ala | Lys | Ile | Gly | Lys | Glu | Val | Val | Ile | Ala | Asn | Lys | Glu | Gly | Val | Gln |
| 465 | | | | | 470 | | | | | 475 | | | | | 480 |
| Glu | Ala | Asp | Arg | Ser | Glu | Asp | Gly | Phe | Tyr | Ile | Arg | Ser | Gly | Ile | Thr |
| | | | | 485 | | | | | 490 | | | | | 495 | |
| Ile | Ile | Met | Glu | Lys | Ala | Thr | Ile | Glu | Asp | Gly | Thr | Val | Ile | | |
| | | | 500 | | | | | 505 | | | | | 510 | | |

( 2 ) INFORMATION FOR SEQ ID NO:3:

( i ) SEQUENCE CHARACTERISTICS:
        ( A ) LENGTH: 1954 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
  ( A ) NAME/KEY: CDS
  ( B ) LOCATION: 81..1628

( x i ) SEQUENCE DESCRIPTION: SEQ ID NO:3:

```
TTTTTTTTTT GTTTGTCTTT CATTGCAGCA GAGCTTGTCT TTGAGACCGG ACACTGTCAG        60

TTCATACCTC CAAAAGCCAT ATG GCG TCA ATG GCT GCG ATC GGT GTT CTC          110
                     Met Ala Ser Met Ala Ala Ile Gly Val Leu
                      1               5                  10

AAA GTG CCG CCT TCC TCC TCC TCC TCC TCT TCT TCA TCT TCT TCT TCA        158
Lys Val Pro Pro Ser Ser Ser Ser Ser Ser Ser Ser Ser Ser Ser Ser
             15                  20                  25

TCC AAA GCC ATT GCA CGC AAC CTC TCA TTC ACT TCA TCA CAG CTC TGT        206
Ser Lys Ala Ile Ala Arg Asn Leu Ser Phe Thr Ser Ser Gln Leu Cys
         30                  35                  40

GGT GAT AAG ATT TTC ACT GTT TCA GGA ACA AGA AGA AGT TCT GGT AGA        254
Gly Asp Lys Ile Phe Thr Val Ser Gly Thr Arg Arg Ser Ser Gly Arg
         45                  50                  55

AAC CCT TTC ATT GTT TCT CCC AAG GCT GTT TCT GAT TCC AAA AAC TCT        302
Asn Pro Phe Ile Val Ser Pro Lys Ala Val Ser Asp Ser Lys Asn Ser
     60                  65                  70

CAA ACT TGT CTT GAT CCA GAT GCT AGC CGA AGT GTT CTT GGC ATT ATA        350
Gln Thr Cys Leu Asp Pro Asp Ala Ser Arg Ser Val Leu Gly Ile Ile
 75                  80                  85                  90

CTT GGA GGT GGT GCT GGG ACG CGT CTT TAT CCG TTG ACA AAG AAG CGG        398
Leu Gly Gly Gly Ala Gly Thr Arg Leu Tyr Pro Leu Thr Lys Lys Arg
                 95                 100                 105

GCG AAA CCA GCT GTT CCT CTT GGA GCA AAC TAT AGA TTG ATT GAC ATC        446
Ala Lys Pro Ala Val Pro Leu Gly Ala Asn Tyr Arg Leu Ile Asp Ile
             110                 115                 120

CCT GTT AGC AAC TGC CTA AAT AGC AAC ATA TCA AAG ATC TAT GTC CTC        494
Pro Val Ser Asn Cys Leu Asn Ser Asn Ile Ser Lys Ile Tyr Val Leu
         125                 130                 135

ACA CAA TTC AAT TCG GCG TCC TTG AAT CGA CAC TTG TCC CGT GCG TAT        542
Thr Gln Phe Asn Ser Ala Ser Leu Asn Arg His Leu Ser Arg Ala Tyr
     140                 145                 150

GCG AGC AAC TTG GGT GGC TAC AAA AAT GAA GGT TTC GTT GAG GTT CTT        590
Ala Ser Asn Leu Gly Gly Tyr Lys Asn Glu Gly Phe Val Glu Val Leu
155                 160                 165                 170

GCC GCG CAG CAG AGT CCT GAG AAT CCA AAT TGG TTC CAG GGC ACT GCG        638
Ala Ala Gln Gln Ser Pro Glu Asn Pro Asn Trp Phe Gln Gly Thr Ala
                 175                 180                 185

GAT GCG GTG AGG CAA TAT TTA TGG CTT TTT GAA GAG CAC AAT GTT TTG        686
Asp Ala Val Arg Gln Tyr Leu Trp Leu Phe Glu Glu His Asn Val Leu
             190                 195                 200

GAA TAC TTG GTT CTG GCG GGT GAC CAT TTG TAT CGA ATG GAT TAT GAG        734
Glu Tyr Leu Val Leu Ala Gly Asp His Leu Tyr Arg Met Asp Tyr Glu
         205                 210                 215

AGA TTT ATA CAA GCA CAC AGG GAA AGT GAT GCT GAT ATC ACT GTT GCG        782
Arg Phe Ile Gln Ala His Arg Glu Ser Asp Ala Asp Ile Thr Val Ala
     220                 225                 230

TCA TTG CCA ATG GAT GAA GCG CGT GCC ACT GCA TTC GGT CTA ATG AAA        830
Ser Leu Pro Met Asp Glu Ala Arg Ala Thr Ala Phe Gly Leu Met Lys
235                 240                 245                 250

ATT GAT GAA GAG GGG CGT ATA GTT GAG TTT TCA GAG AAG CCG AAA GGA        878
Ile Asp Glu Glu Gly Arg Ile Val Glu Phe Ser Glu Lys Pro Lys Gly
                 255                 260                 265

GAA CAG TTG AAA GCT ATG AAG GTT GAT ACG ACT ATT TTG GGT CTC GAC        926
Glu Gln Leu Lys Ala Met Lys Val Asp Thr Thr Ile Leu Gly Leu Asp
             270                 275                 280
```

| | | | | | | | | | | | | | | | | |
|---|---|---|---|---|---|---|---|---|---|---|---|---|---|---|---|---|
| GAC | GAG | AGA | GCT | AAG | GAA | ATG | CCT | TAC | ATT | GCT | AGC | ATG | GGT | ATA | TAT | 974 |
| Asp | Glu | Arg | Ala | Lys | Glu | Met | Pro | Tyr | Ile | Ala | Ser | Met | Gly | Ile | Tyr | |
| | | 285 | | | | 290 | | | | | | 295 | | | | |
| GTT | GTC | AGC | AAA | CAT | GTG | ATG | CTA | GAT | CTG | CTC | CGC | GAC | AAG | TTT | CCT | 1022 |
| Val | Val | Ser | Lys | His | Val | Met | Leu | Asp | Leu | Leu | Arg | Asp | Lys | Phe | Pro | |
| | | 300 | | | | 305 | | | | | 310 | | | | | |
| GGT | GCA | AAC | GAC | TTT | GGT | AGC | GAA | GTT | ATT | CCT | GGT | GCG | ACC | GAG | CTT | 1070 |
| Gly | Ala | Asn | Asp | Phe | Gly | Ser | Glu | Val | Ile | Pro | Gly | Ala | Thr | Glu | Leu | |
| 315 | | | | | 320 | | | | | 325 | | | | | 330 | |
| GGA | TTG | AGA | GTG | CAA | GCT | TAT | TTA | TAC | GAT | GGA | TAC | TGG | GAA | GAC | ATT | 1118 |
| Gly | Leu | Arg | Val | Gln | Ala | Tyr | Leu | Tyr | Asp | Gly | Tyr | Trp | Glu | Asp | Ile | |
| | | | | 335 | | | | | 340 | | | | | 345 | | |
| GGT | ACG | ATT | GAG | GCT | TTC | TAT | AAT | GCA | AAT | CTG | GGA | ATC | ACC | AAA | AAG | 1166 |
| Gly | Thr | Ile | Glu | Ala | Phe | Tyr | Asn | Ala | Asn | Leu | Gly | Ile | Thr | Lys | Lys | |
| | | | 350 | | | | | 355 | | | | | 360 | | | |
| CCT | GTG | CCA | GAT | TTT | AGT | TTC | TAT | GAC | CGT | TCA | TCT | CCA | ATC | TAC | ACC | 1214 |
| Pro | Val | Pro | Asp | Phe | Ser | Phe | Tyr | Asp | Arg | Ser | Ser | Pro | Ile | Tyr | Thr | |
| | | 365 | | | | | 370 | | | | | 375 | | | | |
| CAA | CCT | CGA | TAT | TTG | CCT | CCC | TCT | AAG | ATG | CTT | GAT | GCT | GAT | ATC | ACC | 1262 |
| Gln | Pro | Arg | Tyr | Leu | Pro | Pro | Ser | Lys | Met | Leu | Asp | Ala | Asp | Ile | Thr | |
| | | 380 | | | | 385 | | | | | 390 | | | | | |
| GAT | AGT | GTT | ATT | GGT | GAA | GGA | TGT | GTA | ATT | AAG | AAT | TGC | AAA | ATT | CAC | 1310 |
| Asp | Ser | Val | Ile | Gly | Glu | Gly | Cys | Val | Ile | Lys | Asn | Cys | Lys | Ile | His | |
| 395 | | | | | 400 | | | | | 405 | | | | | 410 | |
| CAT | TCT | GTC | GTT | GGA | CTG | CGA | TCT | TGC | ATA | TCA | GAA | GGT | GCA | ATC | ATT | 1358 |
| His | Ser | Val | Val | Gly | Leu | Arg | Ser | Cys | Ile | Ser | Glu | Gly | Ala | Ile | Ile | |
| | | | | 415 | | | | | 420 | | | | | 425 | | |
| GAG | GAC | ACG | TTG | TTA | ATG | GGA | GCA | GAT | TAT | TAT | GAG | ACG | GAT | GCT | GAT | 1406 |
| Glu | Asp | Thr | Leu | Leu | Met | Gly | Ala | Asp | Tyr | Tyr | Glu | Thr | Asp | Ala | Asp | |
| | | | 430 | | | | | 435 | | | | | 440 | | | |
| AGG | AGG | TTT | TTG | GCT | GCT | AAA | GGC | GGT | GTT | CCA | ATC | GGT | ATT | GGC | AAG | 1454 |
| Arg | Arg | Phe | Leu | Ala | Ala | Lys | Gly | Gly | Val | Pro | Ile | Gly | Ile | Gly | Lys | |
| | | 445 | | | | 450 | | | | | 455 | | | | | |
| AAT | TCT | CAT | ATT | AAA | AGG | GCA | ATC | ATT | GAC | AAG | AAT | GCT | AGA | ATT | GGT | 1502 |
| Asn | Ser | His | Ile | Lys | Arg | Ala | Ile | Ile | Asp | Lys | Asn | Ala | Arg | Ile | Gly | |
| | 460 | | | | | 465 | | | | | 470 | | | | | |
| GAC | GAT | GTC | AAG | ATT | ATT | AAC | AGC | GAC | AAT | GTG | CAA | GAA | GCT | GCA | AGG | 1550 |
| Asp | Asp | Val | Lys | Ile | Ile | Asn | Ser | Asp | Asn | Val | Gln | Glu | Ala | Ala | Arg | |
| 475 | | | | | 480 | | | | | 485 | | | | | 490 | |
| GAA | ACG | GAA | GGT | TAT | TTC | ATA | AAA | AGT | GGT | ATT | GTC | ACA | GTA | ATC | AAG | 1598 |
| Glu | Thr | Glu | Gly | Tyr | Phe | Ile | Lys | Ser | Gly | Ile | Val | Thr | Val | Ile | Lys | |
| | | | | 495 | | | | | 500 | | | | | 505 | | |
| GAT | GCA | TTA | ATT | CCA | AGT | GGA | ACT | GTC | ATC | TAAGAGCACT | CTCTATTA | | | | | 1646 |
| Asp | Ala | Leu | Ile | Pro | Ser | Gly | Thr | Val | Ile | | | | | | | |
| | | | 510 | | | | | 515 | | | | | | | | |

| | | | | |
|---|---|---|---|---|
| CTGTTGCCTC | ATGCAGCTGT | GCAATGCAAC | AACCCATTTT | CACCGCTAGA AGGTGGTAAA | 1706 |
| AGAGCAGTTC | CGCTTCCTCG | TTGGTTTTCT | GGTGCAATGT | TATATTTGGT TCGCGAGTAT | 1766 |
| ATAGAGTAGA | GGACCCTTTC | TGAAGTCGCG | ATGTAAATTT | AATTTTATTC AGTCAAATAA | 1826 |
| ATGCTTCTTT | GGTCTGCAGT | GTCTGTGATG | CATGTTCTTT | TGCAGTTTAT CAAAGGTGTG | 1886 |
| GAATGATATC | CACAGAAAAC | AATGAAAAGT | GATACAATAA | AAGCCAGACA CTTAGCTTCT | 1946 |
| ATTGACGC | | | | | 1954 |

( 2 ) INFORMATION FOR SEQ ID NO:4:

( i ) SEQUENCE CHARACTERISTICS:
        ( A ) LENGTH: 516 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ala | Ser | Met | Ala | Ala | Ile | Gly | Val | Leu | Lys | Val | Pro | Pro | Ser | Ser |
|---|---|---|---|---|---|---|---|---|---|---|---|---|---|---|---|
| 1 | | | | 5 | | | | | 10 | | | | | 15 | |
| Ser | Ser | Ser | Ser | Ser | Ser | Ser | Ser | Ser | Ser | Lys | Ala | Ile | Ala | Arg | |
| | | | 20 | | | | | 25 | | | | | 30 | | |
| Asn | Leu | Ser | Phe | Thr | Ser | Ser | Gln | Leu | Cys | Gly | Asp | Lys | Ile | Phe | Thr |
| | | | 35 | | | | 40 | | | | | 45 | | | |
| Val | Ser | Gly | Thr | Arg | Arg | Ser | Ser | Gly | Arg | Asn | Pro | Phe | Ile | Val | Ser |
| | 50 | | | | | 55 | | | | | 60 | | | | |
| Pro | Lys | Ala | Val | Ser | Asp | Ser | Lys | Asn | Ser | Gln | Thr | Cys | Leu | Asp | Pro |
| 65 | | | | | 70 | | | | | 75 | | | | | 80 |
| Asp | Ala | Ser | Arg | Ser | Val | Leu | Gly | Ile | Ile | Leu | Gly | Gly | Gly | Ala | Gly |
| | | | | 85 | | | | | 90 | | | | | 95 | |
| Thr | Arg | Leu | Tyr | Pro | Leu | Thr | Lys | Lys | Arg | Ala | Lys | Pro | Ala | Val | Pro |
| | | | | 100 | | | | | 105 | | | | | 110 | |
| Leu | Gly | Ala | Asn | Tyr | Arg | Leu | Ile | Asp | Ile | Pro | Val | Ser | Asn | Cys | Leu |
| | | | 115 | | | | | 120 | | | | | 125 | | |
| Asn | Ser | Asn | Ile | Ser | Lys | Ile | Tyr | Val | Leu | Thr | Gln | Phe | Asn | Ser | Ala |
| | 130 | | | | | 135 | | | | | 140 | | | | |
| Ser | Leu | Asn | Arg | His | Leu | Ser | Arg | Ala | Tyr | Ala | Ser | Asn | Leu | Gly | Gly |
| 145 | | | | | 150 | | | | | 155 | | | | | 160 |
| Tyr | Lys | Asn | Glu | Gly | Phe | Val | Glu | Val | Leu | Ala | Ala | Gln | Gln | Ser | Pro |
| | | | | 165 | | | | | 170 | | | | | 175 | |
| Glu | Asn | Pro | Asn | Trp | Phe | Gln | Gly | Thr | Ala | Asp | Ala | Val | Arg | Gln | Tyr |
| | | | 180 | | | | | 185 | | | | | 190 | | |
| Leu | Trp | Leu | Phe | Glu | Glu | His | Asn | Val | Leu | Glu | Tyr | Leu | Val | Leu | Ala |
| | | | 195 | | | | | 200 | | | | | 205 | | |
| Gly | Asp | His | Leu | Tyr | Arg | Met | Asp | Tyr | Glu | Arg | Phe | Ile | Gln | Ala | His |
| | 210 | | | | | 215 | | | | | 220 | | | | |
| Arg | Glu | Ser | Asp | Ala | Asp | Ile | Thr | Val | Ala | Ser | Leu | Pro | Met | Asp | Glu |
| 225 | | | | | 230 | | | | | 235 | | | | | 240 |
| Ala | Arg | Ala | Thr | Ala | Phe | Gly | Leu | Met | Lys | Ile | Asp | Glu | Glu | Gly | Arg |
| | | | | 245 | | | | | 250 | | | | | 255 | |
| Ile | Val | Glu | Phe | Ser | Glu | Lys | Pro | Lys | Gly | Glu | Gln | Leu | Lys | Ala | Met |
| | | | 260 | | | | | 265 | | | | | 270 | | |
| Lys | Val | Asp | Thr | Thr | Ile | Leu | Gly | Leu | Asp | Asp | Glu | Arg | Ala | Lys | Glu |
| | | | 275 | | | | | 280 | | | | | 285 | | |
| Met | Pro | Tyr | Ile | Ala | Ser | Met | Gly | Ile | Tyr | Val | Val | Ser | Lys | His | Val |
| | 290 | | | | | 295 | | | | | 300 | | | | |
| Met | Leu | Asp | Leu | Leu | Arg | Asp | Lys | Phe | Pro | Gly | Ala | Asn | Asp | Phe | Gly |
| 305 | | | | | 310 | | | | | 315 | | | | | 320 |
| Ser | Glu | Val | Ile | Pro | Gly | Ala | Thr | Glu | Leu | Gly | Leu | Arg | Val | Gln | Ala |
| | | | | 325 | | | | | 330 | | | | | 335 | |
| Tyr | Leu | Tyr | Asp | Gly | Tyr | Trp | Glu | Asp | Ile | Gly | Thr | Ile | Glu | Ala | Phe |
| | | | 340 | | | | | 345 | | | | | 350 | | |
| Tyr | Asn | Ala | Asn | Leu | Gly | Ile | Thr | Lys | Lys | Pro | Val | Pro | Asp | Phe | Ser |
| | | | 355 | | | | | 360 | | | | | 365 | | |
| Phe | Tyr | Asp | Arg | Ser | Ser | Pro | Ile | Tyr | Thr | Gln | Pro | Arg | Tyr | Leu | Pro |
| | | 370 | | | | | 375 | | | | | 380 | | | |
| Pro | Ser | Lys | Met | Leu | Asp | Ala | Asp | Ile | Thr | Asp | Ser | Val | Ile | Gly | Glu |
| 385 | | | | | 390 | | | | | 395 | | | | | 400 |

| Gly | Cys | Val | Ile | Lys | Asn | Cys | Lys | Ile | His | His | Ser | Val | Val | Gly | Leu |
|---|---|---|---|---|---|---|---|---|---|---|---|---|---|---|---|
| | | | | 405 | | | | | 410 | | | | | 415 | |

| Arg | Ser | Cys | Ile | Ser | Glu | Gly | Ala | Ile | Ile | Glu | Asp | Thr | Leu | Leu | Met |
|---|---|---|---|---|---|---|---|---|---|---|---|---|---|---|---|
| | | | 420 | | | | | 425 | | | | | 430 | | |

| Gly | Ala | Asp | Tyr | Tyr | Glu | Thr | Asp | Ala | Asp | Arg | Arg | Phe | Leu | Ala | Ala |
|---|---|---|---|---|---|---|---|---|---|---|---|---|---|---|---|
| | | 435 | | | | | 440 | | | | | 445 | | | |

| Lys | Gly | Gly | Val | Pro | Ile | Gly | Ile | Gly | Lys | Asn | Ser | His | Ile | Lys | Arg |
|---|---|---|---|---|---|---|---|---|---|---|---|---|---|---|---|
| | 450 | | | | | 455 | | | | | 460 | | | | |

| Ala | Ile | Ile | Asp | Lys | Asn | Ala | Arg | Ile | Gly | Asp | Asp | Val | Lys | Ile | Ile |
|---|---|---|---|---|---|---|---|---|---|---|---|---|---|---|---|
| 465 | | | | | 470 | | | | | 475 | | | | | 480 |

| Asn | Ser | Asp | Asn | Val | Gln | Glu | Ala | Ala | Arg | Glu | Thr | Glu | Gly | Tyr | Phe |
|---|---|---|---|---|---|---|---|---|---|---|---|---|---|---|---|
| | | | | 485 | | | | | 490 | | | | | 495 | |

| Ile | Lys | Ser | Gly | Ile | Val | Thr | Val | Ile | Lys | Asp | Ala | Leu | Ile | Pro | Ser |
|---|---|---|---|---|---|---|---|---|---|---|---|---|---|---|---|
| | | | 500 | | | | | 505 | | | | | 510 | | |

| Gly | Thr | Val | Ile |
|---|---|---|---|
| | | | 515 |

( 2 ) INFORMATION FOR SEQ ID NO:5:

( i ) SEQUENCE CHARACTERISTICS:
        ( A ) LENGTH: 1814 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 82..1602

( x i ) SEQUENCE DESCRIPTION: SEQ ID NO:5:

```
CATTCACACA CTCTTTGTTC TAAACCACAC AAGAACAAAC ATAGTAACAT AAACACATAA      60

AAACAAACAA CAGTTTCTTC A ATG TCT TCT ATT GTT ACT TCA AGT GTT ATC       111
                         Met Ser Ser Ile Val Thr Ser Ser Val Ile
                          1                5                   10
```

| AAC | GTT | CCA | CGT | TCT | TCT | TCT | TCA | TCA | AAG | AAC | CTC | TCA | TTC | TCA | TCA | 159 |
|---|---|---|---|---|---|---|---|---|---|---|---|---|---|---|---|---|
| Asn | Val | Pro | Arg | Ser | Ser | Ser | Ser | Ser | Lys | Asn | Leu | Ser | Phe | Ser | Ser | |
| | | | | 15 | | | | | 20 | | | | | 25 | | |

| TCA | CAA | CTC | TCC | GGT | GAC | AAG | ATT | CTT | ACA | GTT | TCA | GGT | AAG | GGT | GCA | 207 |
|---|---|---|---|---|---|---|---|---|---|---|---|---|---|---|---|---|
| Ser | Gln | Leu | Ser | Gly | Asp | Lys | Ile | Leu | Thr | Val | Ser | Gly | Lys | Gly | Ala | |
| | | | 30 | | | | | 35 | | | | | 40 | | | |

| CCA | AGA | GGA | AGA | TGC | ACC | CGC | AAG | CAT | GTG | ATT | GTT | ACT | CCT | AAA | GCT | 255 |
|---|---|---|---|---|---|---|---|---|---|---|---|---|---|---|---|---|
| Pro | Arg | Gly | Arg | Cys | Thr | Arg | Lys | His | Val | Ile | Val | Thr | Pro | Lys | Ala | |
| | | 45 | | | | | 50 | | | | | 55 | | | | |

| GTT | TCT | GAT | TCA | CAG | AAC | TCT | CAA | ACT | TGC | CTT | GAT | CCT | GAT | GCT | AGC | 303 |
|---|---|---|---|---|---|---|---|---|---|---|---|---|---|---|---|---|
| Val | Ser | Asp | Ser | Gln | Asn | Ser | Gln | Thr | Cys | Leu | Asp | Pro | Asp | Ala | Ser | |
| | | 60 | | | | | 65 | | | | | 70 | | | | |

| AGA | AGT | GTG | CTT | GGA | ATT | ATA | CTT | GGA | GGT | GGT | GCT | GGT | ACT | CGT | CTT | 351 |
|---|---|---|---|---|---|---|---|---|---|---|---|---|---|---|---|---|
| Arg | Ser | Val | Leu | Gly | Ile | Ile | Leu | Gly | Gly | Gly | Ala | Gly | Thr | Arg | Leu | |
| 75 | | | | | 80 | | | | | 85 | | | | | 90 | |

| TAT | CCA | CTC | ACC | AAG | AAG | AGA | GCA | AAA | CCT | GCT | GTT | CCT | CTT | GGA | GCT | 399 |
|---|---|---|---|---|---|---|---|---|---|---|---|---|---|---|---|---|
| Tyr | Pro | Leu | Thr | Lys | Lys | Arg | Ala | Lys | Pro | Ala | Val | Pro | Leu | Gly | Ala | |
| | | | | 95 | | | | | 100 | | | | | 105 | | |

| AAC | TAT | AGA | CTC | ATT | GAT | ATT | CCT | GTT | AGC | AAT | TGC | TTG | AAT | AGC | AAC | 447 |
|---|---|---|---|---|---|---|---|---|---|---|---|---|---|---|---|---|
| Asn | Tyr | Arg | Leu | Ile | Asp | Ile | Pro | Val | Ser | Asn | Cys | Leu | Asn | Ser | Asn | |
| | | | 110 | | | | | 115 | | | | | 120 | | | |

| ATT | TCT | AAG | ATC | TAT | GTT | CTT | ACT | CAA | TTC | AAT | TCC | GCC | TCA | CTC | AAT | 495 |
|---|---|---|---|---|---|---|---|---|---|---|---|---|---|---|---|---|
| Ile | Ser | Lys | Ile | Tyr | Val | Leu | Thr | Gln | Phe | Asn | Ser | Ala | Ser | Leu | Asn | |
| | | 125 | | | | | 130 | | | | | 135 | | | | |

| CGA | CAT | CTT | TCT | CGC | GCT | TAT | GCG | AGT | AAT | TTG | GGT | GGT | TAC | AAA | AAT | 543 |

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Arg | His | Leu | Ser | Arg | Ala | Tyr | Ala | Ser | Asn | Leu | Gly | Gly | Tyr | Lys | Asn | |
| 140 |     |     |     | 145 |     |     |     |     | 150 |     |     |     |     |     |     | |

| GAG | GGT | TTT | GTT | GAA | GTT | CTT | GCT | GCT | CAG | CAA | AGT | CCT | GAG | AAT | CCT | 591 |
|-----|-----|-----|-----|-----|-----|-----|-----|-----|-----|-----|-----|-----|-----|-----|-----|-----|
| Glu | Gly | Phe | Val | Glu | Val | Leu | Ala | Ala | Gln | Gln | Ser | Pro | Glu | Asn | Pro |     |
| 155 |     |     |     |     | 160 |     |     |     |     | 165 |     |     |     |     | 170 |     |

| AAT | TGG | TTT | CAG | GGT | ACT | GCA | GAT | GCT | GTG | AGG | CAA | TAT | TTA | TGG | CTT | 639 |
|-----|-----|-----|-----|-----|-----|-----|-----|-----|-----|-----|-----|-----|-----|-----|-----|-----|
| Asn | Trp | Phe | Gln | Gly | Thr | Ala | Asp | Ala | Val | Arg | Gln | Tyr | Leu | Trp | Leu |     |
|     |     |     |     | 175 |     |     |     |     | 180 |     |     |     |     | 185 |     |     |

| TTT | GAA | GAG | CAT | AAT | GTT | TTG | GAG | TAC | TTA | ATT | CTG | GCG | GGT | GAC | CAT | 687 |
|-----|-----|-----|-----|-----|-----|-----|-----|-----|-----|-----|-----|-----|-----|-----|-----|-----|
| Phe | Glu | Glu | His | Asn | Val | Leu | Glu | Tyr | Leu | Ile | Leu | Ala | Gly | Asp | His |     |
|     |     |     |     | 190 |     |     |     |     | 195 |     |     |     |     | 200 |     |     |

| TTG | TAT | CGA | ATG | GAT | TAT | GAG | AAA | TTT | ATC | CAA | GCA | CAT | AGG | GAA | TCT | 735 |
|-----|-----|-----|-----|-----|-----|-----|-----|-----|-----|-----|-----|-----|-----|-----|-----|-----|
| Leu | Tyr | Arg | Met | Asp | Tyr | Glu | Lys | Phe | Ile | Gln | Ala | His | Arg | Glu | Ser |     |
|     |     | 205 |     |     |     |     | 210 |     |     |     |     | 215 |     |     |     |     |

| GAT | GCT | GAT | ATC | ACC | GTG | GCT | GCG | TTG | CCA | ATG | GAT | GAA | AAG | CGT | GCA | 783 |
|-----|-----|-----|-----|-----|-----|-----|-----|-----|-----|-----|-----|-----|-----|-----|-----|-----|
| Asp | Ala | Asp | Ile | Thr | Val | Ala | Ala | Leu | Pro | Met | Asp | Glu | Lys | Arg | Ala |     |
| 220 |     |     |     |     | 225 |     |     |     |     | 230 |     |     |     |     |     |     |

| ACT | GCT | TTC | GGT | TTG | ATG | AAG | ATC | GAT | GAA | GAG | GGG | CGT | ATA | ATT | GAG | 831 |
|-----|-----|-----|-----|-----|-----|-----|-----|-----|-----|-----|-----|-----|-----|-----|-----|-----|
| Thr | Ala | Phe | Gly | Leu | Met | Lys | Ile | Asp | Glu | Glu | Gly | Arg | Ile | Ile | Glu |     |
| 235 |     |     |     |     | 240 |     |     |     |     | 245 |     |     |     |     | 250 |     |

| TTT | GCA | GAA | AAG | CCG | AAA | GGA | GAA | CAG | TTG | AAA | GCT | ATG | AAG | GTT | GAT | 879 |
|-----|-----|-----|-----|-----|-----|-----|-----|-----|-----|-----|-----|-----|-----|-----|-----|-----|
| Phe | Ala | Glu | Lys | Pro | Lys | Gly | Glu | Gln | Leu | Lys | Ala | Met | Lys | Val | Asp |     |
|     |     |     |     | 255 |     |     |     |     | 260 |     |     |     |     | 265 |     |     |

| ACT | ACG | ATT | TTA | GGT | CTT | GAC | GAT | GAA | AGA | GCG | AAA | GAA | ATG | CCT | TTT | 927 |
|-----|-----|-----|-----|-----|-----|-----|-----|-----|-----|-----|-----|-----|-----|-----|-----|-----|
| Thr | Thr | Ile | Leu | Gly | Leu | Asp | Asp | Glu | Arg | Ala | Lys | Glu | Met | Pro | Phe |     |
|     |     |     | 270 |     |     |     |     | 275 |     |     |     |     | 280 |     |     |     |

| ATT | GCT | AGC | ATG | GGT | ATA | TAT | GTT | ATC | AGC | AAA | AAT | GTG | ATG | CTA | GAC | 975 |
|-----|-----|-----|-----|-----|-----|-----|-----|-----|-----|-----|-----|-----|-----|-----|-----|-----|
| Ile | Ala | Ser | Met | Gly | Ile | Tyr | Val | Ile | Ser | Lys | Asn | Val | Met | Leu | Asp |     |
|     |     | 285 |     |     |     |     | 290 |     |     |     |     | 295 |     |     |     |     |

| CTT | CTC | CGC | GAC | AAG | TTT | CCC | GGT | GCA | AAT | GAC | TTT | GGG | AGT | GAA | GTG | 1023 |
|-----|-----|-----|-----|-----|-----|-----|-----|-----|-----|-----|-----|-----|-----|-----|-----|------|
| Leu | Leu | Arg | Asp | Lys | Phe | Pro | Gly | Ala | Asn | Asp | Phe | Gly | Ser | Glu | Val |      |
| 300 |     |     |     |     | 305 |     |     |     |     | 310 |     |     |     |     |     |      |

| ATT | CCT | GGT | GCT | ACT | TCT | GTT | GGA | ATG | AGA | GTG | CAA | GCT | TAC | TTA | TAT | 1071 |
|-----|-----|-----|-----|-----|-----|-----|-----|-----|-----|-----|-----|-----|-----|-----|-----|------|
| Ile | Pro | Gly | Ala | Thr | Ser | Val | Gly | Met | Arg | Val | Gln | Ala | Tyr | Leu | Tyr |      |
| 315 |     |     |     |     | 320 |     |     |     |     | 325 |     |     |     |     | 330 |      |

| GAT | GGC | TAC | TGG | GAA | GAC | ATT | GGT | ACC | ATT | GAG | GCT | TTC | TAT | AAT | GCA | 1119 |
|-----|-----|-----|-----|-----|-----|-----|-----|-----|-----|-----|-----|-----|-----|-----|-----|------|
| Asp | Gly | Tyr | Trp | Glu | Asp | Ile | Gly | Thr | Ile | Glu | Ala | Phe | Tyr | Asn | Ala |      |
|     |     |     |     | 335 |     |     |     |     | 340 |     |     |     |     | 345 |     |      |

| AAT | CTT | GGA | ATC | ACC | AAA | AAG | CCT | GTG | CCT | GAT | TTC | AGT | TTC | TAT | GAT | 1167 |
|-----|-----|-----|-----|-----|-----|-----|-----|-----|-----|-----|-----|-----|-----|-----|-----|------|
| Asn | Leu | Gly | Ile | Thr | Lys | Lys | Pro | Val | Pro | Asp | Phe | Ser | Phe | Tyr | Asp |      |
|     |     |     | 350 |     |     |     |     | 355 |     |     |     |     | 360 |     |     |      |

| CGT | TCA | TCT | CCG | ATT | TAC | ACC | CAA | CCG | CGA | TAC | TTG | CCT | CCA | TCT | AAG | 1215 |
|-----|-----|-----|-----|-----|-----|-----|-----|-----|-----|-----|-----|-----|-----|-----|-----|------|
| Arg | Ser | Ser | Pro | Ile | Tyr | Thr | Gln | Pro | Arg | Tyr | Leu | Pro | Pro | Ser | Lys |      |
|     |     | 365 |     |     |     |     | 370 |     |     |     |     | 375 |     |     |     |      |

| ATG | CTT | GAT | GCT | GAT | ATT | ACT | GAT | AGT | GTT | ATC | GGA | GAA | GGA | TGT | GTG | 1263 |
|-----|-----|-----|-----|-----|-----|-----|-----|-----|-----|-----|-----|-----|-----|-----|-----|------|
| Met | Leu | Asp | Ala | Asp | Ile | Thr | Asp | Ser | Val | Ile | Gly | Glu | Gly | Cys | Val |      |
|     |     | 380 |     |     |     |     | 385 |     |     |     |     | 390 |     |     |     |      |

| ATT | AAG | AAC | TGC | AAG | ATT | TTC | CAC | TCT | GTG | GTC | GGG | CTG | CGA | TCT | TGC | 1311 |
|-----|-----|-----|-----|-----|-----|-----|-----|-----|-----|-----|-----|-----|-----|-----|-----|------|
| Ile | Lys | Asn | Cys | Lys | Ile | Phe | His | Ser | Val | Val | Gly | Leu | Arg | Ser | Cys |      |
| 395 |     |     |     |     | 400 |     |     |     |     | 405 |     |     |     |     | 410 |      |

| ATA | TCA | GAA | GGT | GCA | ATT | ATT | GAA | GAC | ACT | TTG | TTA | ATG | GGG | GCA | GAT | 1359 |
|-----|-----|-----|-----|-----|-----|-----|-----|-----|-----|-----|-----|-----|-----|-----|-----|------|
| Ile | Ser | Glu | Gly | Ala | Ile | Ile | Glu | Asp | Thr | Leu | Leu | Met | Gly | Ala | Asp |      |
|     |     |     |     | 415 |     |     |     |     | 420 |     |     |     |     | 425 |     |      |

| TAT | TAC | GAG | ACA | GAA | GCT | GAT | AAA | AGG | TTT | TTG | GCT | GCT | AAA | GGC | AGT | 1407 |
|-----|-----|-----|-----|-----|-----|-----|-----|-----|-----|-----|-----|-----|-----|-----|-----|------|
| Tyr | Tyr | Glu | Thr | Glu | Ala | Asp | Lys | Arg | Phe | Leu | Ala | Ala | Lys | Gly | Ser |      |
|     |     |     | 430 |     |     |     |     | 435 |     |     |     |     | 440 |     |     |      |

| GTT | CCA | ATT | GGT | ATC | GGC | AAA | AAC | TCG | CAT | ATC | AAA | AGA | GCA | ATT | GTT | 1455 |
|-----|-----|-----|-----|-----|-----|-----|-----|-----|-----|-----|-----|-----|-----|-----|-----|------|
| Val | Pro | Ile | Gly | Ile | Gly | Lys | Asn | Ser | His | Ile | Lys | Arg | Ala | Ile | Val |      |
|     |     |     | 445 |     |     |     |     | 450 |     |     |     |     | 455 |     |     |      |

| GAC | AAG | AAC | GCG | AGA | ATC | GGA | GAA | AAC | GTC | AAG | ATA | ATT | AAC | AGT | GAC | 1503 |
|-----|-----|-----|-----|-----|-----|-----|-----|-----|-----|-----|-----|-----|-----|-----|-----|------|

```
Asp  Lys  Asn  Ala  Arg  Ile  Gly  Glu  Asn  Val  Lys  Ile  Ile  Asn  Ser  Asp
     460                 465                      470

AAT  GTT  CAA  GAA  GCT  GCT  AGG  GAA  ACA  GAA  GGC  TAT  TTC  ATC  AAA  AGC       1551
Asn  Val  Gln  Glu  Ala  Ala  Arg  Glu  Thr  Glu  Gly  Tyr  Phe  Ile  Lys  Ser
475                      480                      485                      490

GGG  ATC  GTC  ACA  ATA  ATC  AAG  GAT  GCC  TTG  ATT  CCT  AGT  GGA  ACT  GTC       1599
Gly  Ile  Val  Thr  Ile  Ile  Lys  Asp  Ala  Leu  Ile  Pro  Ser  Gly  Thr  Val
               495                      500                      505

ATA  TAGAAGACTG  AAACTCATCT  TTTGTTTCAT  AATGGTGAGT  GAGACTTGA                       1652
Ile

AGTTCATGTT  GCATGATATA  TTTATTTTTC  GATAAAGGCT  TGTAAATAAT  AGCTGAAGAG               1712

AGAACCTTCT  TGTGTTTTGG  AAACTAGTAC  TGGTAAAGTT  TGTTGATCAA  TTGAATAAAA               1772

GTCGTTTTAT  TTTCCACCTC  TAAAAAAAAA  AAAAAAAAA  AA                                    1814
```

( 2 ) INFORMATION FOR SEQ ID NO:6:

( i ) SEQUENCE CHARACTERISTICS:
        ( A ) LENGTH: 507 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ser  Ser  Ile  Val  Thr  Ser  Ser  Val  Ile  Asn  Val  Pro  Arg  Ser  Ser
1                   5                        10                      15

Ser  Ser  Ser  Lys  Asn  Leu  Ser  Phe  Ser  Ser  Ser  Gln  Leu  Ser  Gly  Asp
               20                       25                      30

Lys  Ile  Leu  Thr  Val  Ser  Gly  Lys  Gly  Ala  Pro  Arg  Gly  Arg  Cys  Thr
               35                       40                      45

Arg  Lys  His  Val  Ile  Val  Thr  Pro  Lys  Ala  Val  Ser  Asp  Ser  Gln  Asn
     50                       55                      60

Ser  Gln  Thr  Cys  Leu  Asp  Pro  Asp  Ala  Ser  Arg  Ser  Val  Leu  Gly  Ile
65                       70                      75                       80

Ile  Leu  Gly  Gly  Gly  Ala  Gly  Thr  Arg  Leu  Tyr  Pro  Leu  Thr  Lys  Lys
                    85                       90                      95

Arg  Ala  Lys  Pro  Ala  Val  Pro  Leu  Gly  Ala  Asn  Tyr  Arg  Leu  Ile  Asp
               100                      105                     110

Ile  Pro  Val  Ser  Asn  Cys  Leu  Asn  Ser  Asn  Ile  Ser  Lys  Ile  Tyr  Val
               115                      120                     125

Leu  Thr  Gln  Phe  Asn  Ser  Ala  Ser  Leu  Asn  Arg  His  Leu  Ser  Arg  Ala
     130                      135                     140

Tyr  Ala  Ser  Asn  Leu  Gly  Gly  Tyr  Lys  Asn  Glu  Gly  Phe  Val  Glu  Val
145                      150                     155                     160

Leu  Ala  Ala  Gln  Gln  Ser  Pro  Glu  Asn  Pro  Asn  Trp  Phe  Gln  Gly  Thr
                    165                     170                     175

Ala  Asp  Ala  Val  Arg  Gln  Tyr  Leu  Trp  Leu  Phe  Glu  Glu  His  Asn  Val
               180                     185                     190

Leu  Glu  Tyr  Leu  Ile  Leu  Ala  Gly  Asp  His  Leu  Tyr  Arg  Met  Asp  Tyr
     195                     200                     205

Glu  Lys  Phe  Ile  Gln  Ala  His  Arg  Glu  Ser  Asp  Ala  Asp  Ile  Thr  Val
     210                     215                     220

Ala  Ala  Leu  Pro  Met  Asp  Glu  Lys  Arg  Ala  Thr  Ala  Phe  Gly  Leu  Met
225                      230                     235                     240

Lys  Ile  Asp  Glu  Glu  Gly  Arg  Ile  Ile  Glu  Phe  Ala  Glu  Lys  Pro  Lys
                    245                     250                     255
```

| | | | | | | | | | | | | | | |
|---|---|---|---|---|---|---|---|---|---|---|---|---|---|---|
| Gly | Glu | Gln | Leu<br>260 | Lys | Ala | Met | Lys | Val<br>265 | Asp | Thr | Thr | Ile | Leu<br>270 | Gly | Leu |
| Asp | Asp | Glu | Arg<br>275 | Ala | Lys | Glu | Met<br>280 | Pro | Phe | Ile | Ala | Ser<br>285 | Met | Gly | Ile |
| Tyr | Val | Ile<br>290 | Ser | Lys | Asn | Val<br>295 | Met | Leu | Asp | Leu | Leu<br>300 | Arg | Asp | Lys | Phe |
| Pro<br>305 | Gly | Ala | Asn | Asp | Phe<br>310 | Gly | Ser | Glu | Val | Ile<br>315 | Pro | Gly | Ala | Thr | Ser<br>320 |
| Val | Gly | Met | Arg | Val<br>325 | Gln | Ala | Tyr | Leu | Tyr<br>330 | Asp | Gly | Tyr | Trp | Glu<br>335 | Asp |
| Ile | Gly | Thr | Ile<br>340 | Glu | Ala | Phe | Tyr | Asn<br>345 | Ala | Asn | Leu | Gly | Ile<br>350 | Thr | Lys |
| Lys | Pro | Val<br>355 | Pro | Asp | Phe | Ser | Phe<br>360 | Tyr | Asp | Arg | Ser | Ser<br>365 | Pro | Ile | Tyr |
| Thr | Gln<br>370 | Pro | Arg | Tyr | Leu | Pro<br>375 | Pro | Ser | Lys | Met | Leu<br>380 | Asp | Ala | Asp | Ile |
| Thr<br>385 | Asp | Ser | Val | Ile | Gly<br>390 | Glu | Gly | Cys | Val | Ile<br>395 | Lys | Asn | Cys | Lys | Ile<br>400 |
| Phe | His | Ser | Val | Val<br>405 | Gly | Leu | Arg | Ser | Cys<br>410 | Ile | Ser | Glu | Gly | Ala<br>415 | Ile |
| Ile | Glu | Asp | Thr<br>420 | Leu | Leu | Met | Gly | Ala<br>425 | Asp | Tyr | Tyr | Glu | Thr<br>430 | Glu | Ala |
| Asp | Lys | Arg<br>435 | Phe | Leu | Ala | Ala | Lys<br>440 | Gly | Ser | Val | Pro | Ile<br>445 | Gly | Ile | Gly |
| Lys | Asn<br>450 | Ser | His | Ile | Lys | Arg<br>455 | Ala | Ile | Val | Asp | Lys<br>460 | Asn | Ala | Arg | Ile |
| Gly<br>465 | Glu | Asn | Val | Lys | Ile<br>470 | Ile | Asn | Ser | Asp | Asn<br>475 | Val | Gln | Glu | Ala | Ala<br>480 |
| Arg | Glu | Thr | Glu | Gly<br>485 | Tyr | Phe | Ile | Lys | Ser<br>490 | Gly | Ile | Val | Thr | Ile<br>495 | Ile |
| Lys | Asp | Ala | Leu<br>500 | Ile | Pro | Ser | Gly | Thr<br>505 | Val | Ile | | | | | |

( 2 ) INFORMATION FOR SEQ ID NO:7:

( i ) SEQUENCE CHARACTERISTICS:
        ( A ) LENGTH: 292 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
GATCAAACCT GCTTCTTTTT CTGCTATTCT TACTTCAGAT GACCCCAAAG GTTCCCTGGT      60
AAACTCAGTT TCATTCTGGG TTTCACTTTT TGCTTCCAAT TCTGAAAAAA AGAAAGACTT     120
TTTTTTCCTC CCATTATATG ACATAACTTT TTATGTTAA TTATTTTGCT ACATTTGTTT      180
GGTATATGAT TATGATTATG ATTATGATTT TGAGTGTATG TTTTGAAATT CAGAATTTGC     240
AAGTGCCTTC ATTTCTGAGA CTAAGAGCTG ATCCAAAAAA TGTGATTTCC AT             292
```

( 2 ) INFORMATION FOR SEQ ID NO:8:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| CTGCAGATGC | TGTGAGACAA | TTTACCTGGA | TATTTGAGGT | AGACAAACGA | TTTTCGTTGT | 60 |
| TGTTGTTGTA | TATACATTTT | GATAAATAAT | AGATTCGTTT | GTTCTCATTT | TTGAGCTTGT | 120 |
| CAATAAGTAA | TAGATTGTTT | GTGGTAGGAT | GCCAAGAATA | TAAACGTCGA | GAATGTATTG | 180 |
| ATCTTGGCGG | GAGATCATTT | ATATCGAATG | GATTACATGG | ACCTATTGCA | GGTATACTGT | 240 |
| GAATGTTTTG | TAGAGTAGAT | TGTTTTTCAT | TTCATGTTCT | AGAGTTTTCT | GATTCATCTA | 300 |
| TATAACAAAT | TAACAGAGTC | ACGTTGATAG | AAA | | | 333 |

( 2 ) INFORMATION FOR SEQ ID NO:9:

( i ) SEQUENCE CHARACTERISTICS:
        ( A ) LENGTH: 319 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

| GGATCCGAAA | TCATTCCTTC | CGCTATAAGA | GAACACAATG | TCCAAGTAAG | AGGAATTCTG | 60 |
| ATAAATATAT | CTGCTTACAA | ATGTTTTTTT | TCATTTCACA | AGATTTTTAT | CTGCCATCTA | 120 |
| TNTTTTTTGC | AGGCATACTT | TTTCGGAGAC | TACTGGGAAG | ATATTGGAAC | GATAAAATCC | 180 |
| TTCTACGATG | CTAACCTCGC | TCTTACTGAA | GAGGTAGGTT | CAAGAATTTT | TCTAGTGTTC | 240 |
| TTGTTCAGTT | TTAGTTGATT | GAAACTAAAT | CTGCTATATG | TTACTCTCTC | GCAGAGTCCA | 300 |
| AAGTTCGAGT | TTTATGATC | | | | | 319 |

( 2 ) INFORMATION FOR SEQ ID NO:10:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i i ) MOLECULE TYPE: DNA (primer)

( x i ) SEQUENCE DESCRIPTION: SEQ ID NO:10:

AGAAGCCATG GTAGTAACC                                                                                                                                                  19

( 2 ) INFORMATION FOR SEQ ID NO:11:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) MOLECULE TYPE: DNA (linker)

( x i ) SEQUENCE DESCRIPTION: SEQ ID NO:11:

CGGAATTCCG       10

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear (  i  i  ) MOLECULE TYPE: DNA (oligonucleotide)

(  x  i  ) SEQUENCE DESCRIPTION: SEQ ID NO:12:

TTTRATNGTN CCRAYRTCYT CCCARTANCC  30

( 2 ) INFORMATION FOR SEQ ID NO:13:

(  i  ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear (  i  i  ) MOLECULE TYPE: DNA (primer)

(  x  i  ) SEQUENCE DESCRIPTION: SEQ ID NO:13:

CGCAGCCATG GACGCCATA  19

( 2 ) INFORMATION FOR SEQ ID NO:14:

(  i  ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear (  i  i  ) MOLECULE TYPE: DNA (primer)

(  x  i  ) SEQUENCE DESCRIPTION: SEQ ID NO:14:

GAGAATGTAT TGATCTTGGC GGGAG  25

( 2 ) INFORMATION FOR SEQ ID NO:15:

(  i  ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear (  i  i  ) MOLECULE TYPE: DNA (primer)

(  x  i  ) SEQUENCE DESCRIPTION: SEQ ID NO:15:

CCAATATCTT CCCAGTAGTC TCCGA  25